(12) United States Patent
Feng et al.

(10) Patent No.: US 7,592,342 B2
(45) Date of Patent: Sep. 22, 2009

(54) QUINOXALINE DERIVATIVES AS PI3 KINASE INHIBITORS

(75) Inventors: Yanhong Feng, Collegeville, PA (US); Cynthia A. Parrish, Collegeville, PA (US); Martha A Sarpong, Collegeville, PA (US); Domingos J Silva, Collegeville, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 12/117,127

(22) Filed: May 8, 2008

(65) Prior Publication Data

US 2008/0293706 A1    Nov. 27, 2008

Related U.S. Application Data

(60) Provisional application No. 60/917,120, filed on May 10, 2007.

(51) Int. Cl.
A61K 31/498    (2006.01)

(52) U.S. Cl. ...................................... 514/249; 544/353
(58) Field of Classification Search ................. 544/353
See application file for complete search history.

(56) References Cited

U.S. PATENT DOCUMENTS

| | | | |
|---|---|---|---|
| 4,734,407 | A | 3/1988 | Schmidt et al. |
| 5,925,656 | A | 7/1999 | Kallam et al. |
| 5,965,589 | A | 10/1999 | Sohda et al. |
| 6,180,632 | B1 | 1/2001 | Myers |
| 6,452,014 | B1 | 9/2002 | Akama et al. |
| 7,153,875 | B2 | 12/2006 | Pfahl et al. |
| 7,348,348 | B2 | 3/2008 | Kuo et al. |
| 2002/0120144 | A1 | 8/2002 | Akama et al. |
| 2002/0143182 | A1 | 10/2002 | Pfahl et al. |
| 2003/0003396 | A1 | 1/2003 | Berneth et al. |
| 2004/0009527 | A1 | 1/2004 | Dong et al. |
| 2004/0092561 | A1 | 5/2004 | Ruckle et al. |
| 2005/0019825 | A9 | 1/2005 | Dong et al. |
| 2005/0042213 | A1 | 2/2005 | Gelder et al. |
| 2005/0165072 | A1 | 7/2005 | Ayer et al. |
| 2005/0176717 | A1 | 8/2005 | Kim |
| 2005/0222155 | A1 | 10/2005 | Biloeau |
| 2005/0222225 | A1 | 10/2005 | DeLuca |
| 2006/0004046 | A1 | 1/2006 | Chen et al. |
| 2006/0106077 | A1 | 5/2006 | Suto et al. |
| 2006/0122176 | A1 | 6/2006 | Rueckle et al. |
| 2006/0276520 | A1 | 12/2006 | Singh et al. |
| 2007/0021447 | A1 | 1/2007 | Rueckle et al. |
| 2007/0078129 | A1 | 4/2007 | Lagu et al. |

FOREIGN PATENT DOCUMENTS

| | | |
|---|---|---|
| EP | 801063 A1 | 10/1997 |
| EP | 801063 B1 | 1/2003 |
| JP | 11130756 | 5/1999 |
| WO | WO98/54157 | 12/1998 |
| WO | WO98/54158 | 12/1998 |
| WO | WO99/59586 | 11/1999 |
| WO | WO03/001049 | 1/2003 |
| WO | WO03/001051 | 1/2003 |
| WO | WO2004/045611 A1 | 6/2004 |
| WO | WO2006/120573 | 11/2006 |

OTHER PUBLICATIONS

Abid, et al., *Arteriosclerosis Thrombrosis and Vascular Biology*, 24:294-300 (2004).
Drees, et al., *Combinational Chemistry and High Throughput Screening*, 6(4):321 (2003).
Foster, et al., *Journal of Cell Science*, 116:3037-3040 (2003).
Fraser, et al., *Science*, 251(4991):313-316 (1991).
Fruman, et al., *Annual Review of Biochemistry*, 67:481-507 (1998).
Gerard, et al., *Nature Immunology*, 2(2):108-115 (2001).
Harari, et al., *Oncogene*, 19:6102-6114 (2000).
Hirsch, et al., *Science*, 287(5455):1049-1053 (2003).
Hirsch, et al., *Faseb Journal*, 15(11):2019-2021 (2001).
Janusz, et al., *Journal of Medicinal Chemistry*, 41(18):3515-3529 (1998).
Katso, et al., *Annual Review of Cell and Developmental Biology*, 17:615-675 (2001).
Kauffmann-Zeh, et al., *Nature*, 385:544-548 (1997).
Laffargue, et al., *Immunity*, 16(3):441-451 (2002).
Lawlor, et al., *Journal of Cell Science*, 114(16):2903-2910 (2001).
Leslie, et al., *Chemical Reviews*, 101(8):2365-2380 (2001).
Lopez-Ilasaca, et al., *Journal of Biological Chemistry*, 273(5):2505-2508 (1998).
Ma, et al., *Oncogene*, 19:2739-2744 (2000).
Meier, et al., *Protein Expression and Purification*, 35(2):218.
Nicholson, et al., *Cellular Signaling*, 14:381-395 (2002).
Nolte, et al., *Nature Structural Biology*, 3:364-374 (1996).
Pages, et al., *Nature*, 369:327-329 (1994).
Panayotou, et al., *Trends in Cell Biology*, 2:358-360 (1992).
Parker, et al., *Current Biology*, 5:577-579 (1995).
Philp, et al., *Cancer Research*, 61:7426-7429 (2001).
Rudd, *Immunity*, 4:527-534 (1996).
Samuels, et al., *Science*, 304: 554 (2004).
Sawyer, *Expert Opinion on Investigational Drugs*, 13:1-19 (2004).
Shayesteh, et al., *Nature Genetics*, 21:99-102 (1999).
Simpson, et al., *Experimental Cell Research*, 264:29-41 (2001).
Stein, et al., *Molecular Medicine Today*, 6(9):347-357 (2000).

(Continued)

*Primary Examiner*—James O Wilson
*Assistant Examiner*—Brian McDowell
(74) *Attorney, Agent, or Firm*—Tony W. Peng; Wayne J. Dustman; Edward R. Gimmi

(57) ABSTRACT

Invented is a method of inhibiting the activity/function of PI3 kinases using quinoxaline derivatives. Also invented is a method of treating one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries by the administration of quinoxaline derivatives.

14 Claims, No Drawings

OTHER PUBLICATIONS

Stephens, et al., *Current Opinion in Cell Biology*, 14(2):203-213 (2002).
Thelen, et al., *Proceedings of the National Academy of Sciences*, 91:4960-4964 (1994).
Toker, et al., *Cellular and Molecular Life Sciences*, 59(5):761-779 (2002).
Vanhaesebroeck, et al., *Trends in Biochemical Sciences*, 22(7): 267-272 (1997).
Vanhaesebroeck, et al., *Experimental Cell Research*, 25(1):239-254 (1999).
Vara, et al., *Cancer Treatment Reviews*, 30:193-204 (2004).
Vivanco, et al., *Nature Reviews Cancer*, 2:489-501 (2002).
Wyman, et al., *Immunology Today*, 21(6):260-264 (2000).

QUINOXALINE DERIVATIVES AS PI3 KINASE INHIBITORS

This application claims the benefit of U.S. provisional Application No. 60/917,120 filed May 10, 2007.

FIELD OF THE INVENTION

This invention relates to the use of quinoxaline derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ. Suitably, the present invention relates to the use of quinoxalines in the treatment of one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

BACKGROUND OF THE INVENTION

Cellular membranes represent a large store of second messengers that can be enlisted in a variety of signal transduction pathways. In regards function and regulation of effector enzymes in phospholipids signaling pathways, these enzymes generate second messengers from the membrane phospholipid pools (class I PI3 kinases (e.g. PI3Kalpha)) are dual-specificity kinase enzymes, meaning they display both: lipid kinase (phosphorylation of phosphoinositides) as well as protein kinase activity, shown to be capable of phosphorylation of protein as substrate, including auto-phosphorylation as intramolecular regulatory mechanism. These enzymes of phospholipids signaling are activated in response to a variety of extra-cellular signals such as growth factors, mitogens, integrins (cell-cell interactions) hormones, cytokines, viruses and neurotransmitters such as described in Scheme A hereinafter and also by intracellular regulation by other signaling molecules (cross-talk, where the original signal can activate some parallel pathways that in a second step transmit signals to PI3Ks by intra-cellular signaling events), such as small GTPases, kinases or phosphatases for example. Intracellular regulation can also occur as a result of aberrant expression or lack of expression of cellular oncogenes or tumor suppressors. The inositol phospholipid (phosphoinositides) intracellular signaling pathways begin with activation of a signaling molecules (extra cellular ligands, stimuli, receptor dimerization, transactivation by heterologous receptor (e.g. receptor tyrosine kinase)) the recruitment and activation of PI3K including the involvement of G-protein linked transmembrane receptor integrated into the plasma membrane.

PI3K converts the membrane phospholipids PI(4,5)P$_2$ into PI(3,4,5)P$_3$ that functions as a second messenger. PI and PI(4)P are also substrates of PI3K and can be phosphorylated and converted into PI3P and PI(3,4)P$_2$, respectively. In addition, these phosphoinositides can be converted into other phosphoinositides by 5'-specific and 3'-specific phosphatases, thus PI3K enzymatic activity results either directly or indirectly in the generation of two 3'-phosphoinositide subtypes that function as $2^{nd}$ messengers in intra-cellular signal transduction pathways (Trends Biochem. Sci. 22(7) p. 267-72 (1997) by Vanhaesebroeck et al.: Chem. Rev. 101(8) p. 2365-80 (2001) by Leslie et al (2001); Annu. Rev. Cell. Dev. Biol. 17p, 615-75 (2001) by Katso et al. and Cell. Mol. Life Sci. 59(5) p. 761-79 (2002) by Toker et al.). Multiple PI3K isoforms categorized by their catalytic subunits, their regulation by corresponding regulatory subunits, expression patterns and signaling-specific functions (p110α, β, δ and γ) perform this enzymatic reaction (Exp. Cell. Res. 25 (1) p. 239-54 (1999) by Vanhaesebroeck and Katso et al., 2001, above).

The closely related isoforms p110α and β are ubiquitously expressed, while δ and γ are more specifically expressed in the haematopoietic cell system, smooth muscle cells, myocytes and endothelial cells (Trends Biochem. Sci. 22(7) p. 267-72 (1997) by Vanhaesebroeck et al.). Their expression might also be regulated in an inducible manner depending on the cellular, tissue type and stimuli as well as disease context. Inducibility of protein expression includes synthesis of protein as well as protein stabilization that is in part regulated by association with regulatory subunits.

To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate (PI(4,5)P$_2$) to produce phosphatidylinositol-3-phosphate (PI3P), phosphatidylinositol-3,4-bisphosphate (PI(3,4)P$_2$, and phosphatidylinositol-3,4,5-trisphosphate (PI(3,4,5)P$_3$, respectively. Class II PI3Ks phosphorylate PI and phosphatidylinositol-4-phosphate. Class III PI3Ks can only phosphorylate PI (Vanhaesebrokeck et al., 1997, above; Vanhaesebroeck et al., 1999, above and Leslie et al, 2001, above)

Scheme A: Conversion of PI(4,5)P2 to PIP3

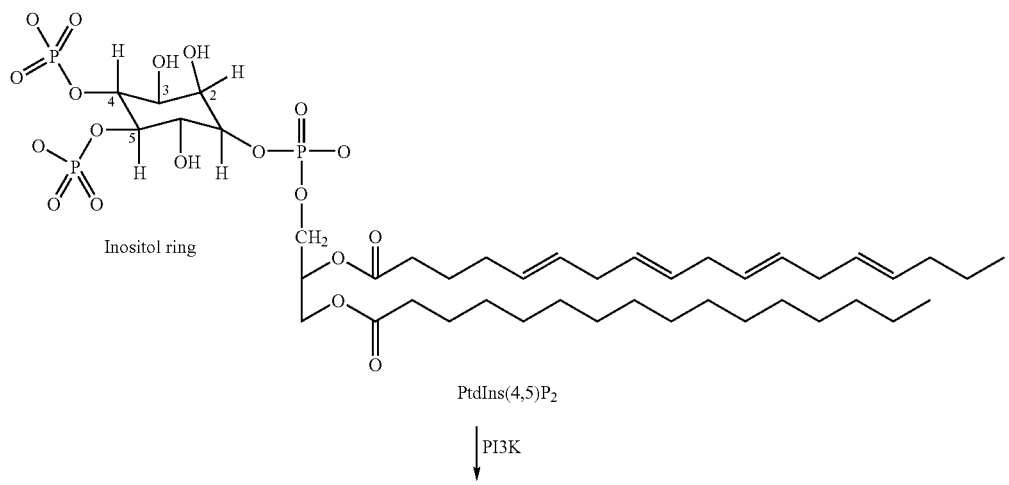

Inositol ring

PtdIns(4,5)P2

PI3K

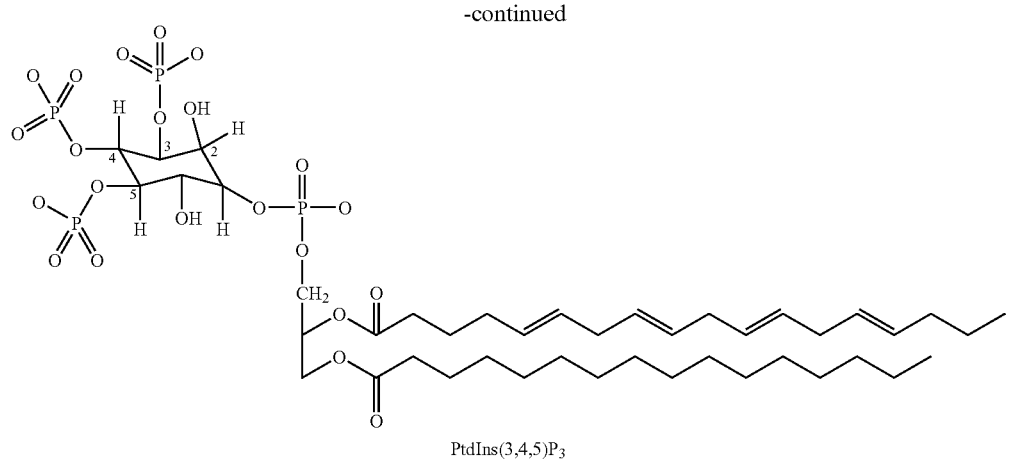

PtdIns(3,4,5)P$_3$

As illustrated in Scheme A above, phosphoinositide 3-kinases (PI3Ks) phosphorylate the hydroxyl of the third carbon of the inositol ring. The phosphorylation of phosphoinositides that generate PtdIns to 3,4,5-trisphosphate (PtdIns(3,4,5) P$_3$), PtdIns(3,4)P$_2$ and PtdIns(3)P produce second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al., 2001, above and Mol. Med. Today 6(9) p. 347-57 (2000) by Stein). G-protein coupled receptors mediated phosphoinositide 3'OH-kinase activation via small GTPases such as Gβγ and Ras, and consequently PI3K signaling plays a central role in establishing and coordinating cell polarity and dynamic organization of the cytoskeleton—which together provides the driving force of cells to move.

Chemotaxis—the directed movement of cells toward a concentration gradient of chemical attractants, also called chemokines is involved in many important diseases such as inflammation/auto-immunity, neurodegeneration, antiogenesis, invasion/metastasis and wound healing (Immunol. Today 21(6) p. 260-4 (2000) by Wyman et al.; Science 287 (5455) p. 1049-53 (2000) by Hirsch et al.; FASEB J. 15(11) p. 2019-21 (2001) by Hirsch et al. and Nat. Immunol. 2(2) p. 108-15 (2001) by Gerard et al.).

Recent advances using genetic approaches and pharmacological tools have provided insights into signalling and molecular pathways that mediate chemotaxis in response to chemoattractant activated G-protein coupled receptors PI3-Kinase, responsible for generating these phosphorylated signalling products, was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol. 2 p. 358-60 (1992)). However, more recent biochemical studies revealed that, class I PI3 kinases (e.g. class IB isoform PI3Kγ) are dual-specific kinase enzymes, means they display both: lipid kinase (phosphorylation of phospho-inosoitides) as well as protein kinase activity, shown to be capable of phosphorylation of other protein as substrates, including auto-phosphorylation as intra-molecular regulatory mechanism.

PI3-kinase activation, is therefore believe to be involved in a range of cellular responses including cell growth, differentiation, and apoptosis (Parker et al., Current Biology, 5 p. 577-99 (1995); Yao et al., Science, 267 p. 2003-05 (1995)). PI3-kinase appears to be involved in a number of aspects of leukocyte activation. A p85-associated PI3-kinase activity has been shown to physically associate with the cytoplasmic domain of CD28, which is an important costimulatory molecule for the activation of T-cells in response to antigen (Pages et al., Nature, 369 p. 327-29 (1994); Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science 251 p. 313-16 (1991)). Mutation of CD28 such that it can longer interact with PI3-kinase leads to a failure to initiate IL2 production, suggesting a critical role for PI3-kinase in T cell activation. PI3Kγ has been identified as a mediator of G beta-gamma-dependent regulation of JNK activity, and G beta-gamma are subunits of heterotrimeric G proteins (Lopez-Ilasaca et al., J. Biol. Chem. 273(5) p. 2505-8 (1998)). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

Recently, (Laffargue et al., Immunity 16(3) p. 441-51 (2002)) it has been described that PI3Kγ relays inflammatory signals through various G(i)-coupled receptors and its central to mast cell function, stimuli in context of leukocytes, immunology includes cytokines, chemokines, adenosines, antibodies, integrins, aggregation factors, growth factors, viruses or hormones for example (J. Cell. Sci. 114(Pt 16) p. 2903-10 (2001) by Lawlor et al.; Laffargue et al., 2002, above and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (cf. hereinafter), have been widely used as PI3-kinase inhibitors. These compounds are non-specific PI3K inhibitors, as they do not distinguish among the four members of Class I PI3-kinases. For example, the IC$_{50}$ values of wortmannin against each of the various Class I PI3-kinases are in the range of 1-10 nM. Similarly, the IC$_{50}$ values for LY294002 against each of these PI3-kinases is about 15-20 µM (Fruman et al., Ann. Rev. Biochem., 67, p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)$P_3$. This synthesis correlates with activation of the respirators burst involved in neutrophil destruction of invading microorganisms. Treatment of neutrophils with wortmannin prevents the fMLP-induced respiratory burst response (Thelen et al., Proc. Natl. Acad. Sci. USA, 91, p. 4960-64 (1994)). Indeed, these experiments with wortmannin, as well as other experimental evidence, shows that PI3K activity in cells of hematopoietic lineage, particularly neutrophils, monocytes, and other types of leukocytes, is involved in many of the non-memory immune response associated with acute and chronic inflammation.

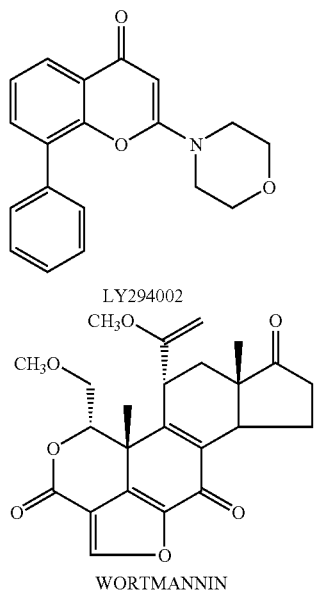

Based on studies using wortmannin, there is evidence that PI3-kinase function is also required for some aspects of leukocyte signaling through G-protein coupled receptors (Thelen et al., 1994, above). Moreover, it has been shown that wortmannin and LY294002 block neutrophil migration and superoxide release. Cyclooxygenase inhibiting benzofuran derivatives are disclosed by John M. Janusz et al., in J. Med. Chem. 1998; Vol. 41, No. 18.

It is now well understood that deregulation of onocogenes and tumour-suppressor genes contributes to the formation fo malignant tumours, for example by way of increase cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (Katso et al., Annual Rev. Cell Dev. Biol., 2001, 17: 615-617 and Foster et al., J. Cell Science, 2003, 116: 3037-3040).

Class I PI3K is a heterodimer consisting of a p110 catalytic subunit and a regulatory subunit, and the family is further divided into class Ia and Class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

There is now considerable evidence indicating that Class Ia PI3K enzymes contribute to tumourigenesis in a wide variety of human cancers, either directly or indirectly (Vivanco and Sawyers, Nature Reviews Cancer, 2002, 2, 489-501). For example, the p110α subunit is amplified in some tumours such as those of the ovary (Shayesteh, et al., Nature Genetics, 1999, 21: 99-102) and cervix (Ma et al., Oncogene, 2000, 19: 2739-2744). More recently, activating mutations within p110α (PIK3CA gene) have been associated with various other tumors such as those of the colon and of the breast and lung (Samuels, et al., Science, 2004, 304, 554). Tumor-related mutations in p85α have also been identified in cancers such as those of the ovary and colon (Philp et al., Cancer Research, 2001, 61, 7426-7429). In addition to direct effects, it is believed that activation of Class Ia PI3K contributes to tumourigenic events that occur upstream in signaling pathways, for example by way of ligand-dependent or ligand-independent activation of receptor tyrosine kinases, GPCR systems or integrins (Vara et al., Cancer Treatment Reviews, 2004, 30, 193-204). Examples of such upstream signaling pathways include over-expression of the receptor tyrosine kinase Erb2 in a variety of tumors leading to activation of PI3K-mediated pathways (Harari et al., Oncogene, 2000, 19, 6102-6114) and over-expression of the oncogene Ras (Kauffmann-Zeh et al., Nature, 1997, 385, 544-548). In addition, Class Ia PI3Ks may contribute indirectly to tumourigenesis caused by various downstream signaling events. For example, loss of function of the PTEN tumor-suppressor phosphatase that catalyses conversion of PI(3,4,5)P3 back to PI(4,5)P2 is associated with a very broad range of tumors via deregulation of PI3K-mediated production of PI(3,4,5)P3 (Simpson and Parsons, Exp. Cell Res., 2001, 264, 29-41). Furthermore, augmentation of the effects of other PI3K-mediated signaling events is believed to contribute to a variety of cancers, for example by activation of AKT (Nicholson and Andeson, Cellular Signaling, 2002, 14, 381-395).

In addition to a role in mediating proliferative and survival signaling in tumor cells, there is also good evidence that class Ia PI3K enzymes also contributes to tumourigenesis via its function in tumor-associated stromal cells. For examples, PI3K signaling is known to play an important role in mediating angiogenic events in endothelial cells in response to pro-angiogenic factors such as VEGF (abid et al., Arterioscler, Thromb. Vasc. Biol., 2004, 24, 294-300). As Class I PI3K enzymes are also involved in motility and migration (Sawyer, Expert Opinion investing. Drugs, 2004, 13, 1-19), PI3K inhibitors are anticipated to provide therapeutic benefit via inhibition of tumor cell invasion and metastasis.

SUMMARY OF THE INVENTION

This invention relates to novel compounds of Formula (I):

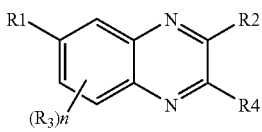
(I)

in which

R1 is an optionally substituted ring system selected from a group consisting of: formula (II), (III), (IV), (V), (VI), (VII) and (VIII):

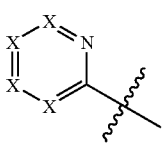
(II)

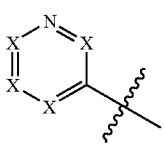
(III)

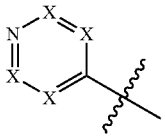
(IV)

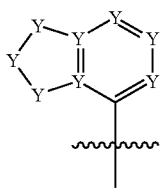
(V)

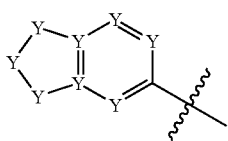
(VI)

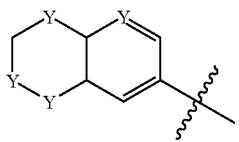
(VII)

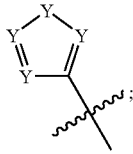
(VIII);

each R2, R3 and R4 is independently selected from: hydrogen, halogen, acyl, amino, substituted amino, arylamino, acylamino, heterocycloalkylamino, C1-6alkyl, substituted C1-6alkyl, C3-7cycloalkyl, substituted C3-7cycloalkyl, C3-7heterocycloalkyl, substituted C3-7heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, acyloxy, and aryloxy;

n is 0-2;

X is C or N; Y is C, O, N or S;

and/or a pharmaceutically acceptable salt, hydrate, solvate or pro-drug thereof;

provided that in each of formula (V) to (VIII) at least one Y is not carbon;

further provided that formula (VIII) is substituted with at least one oxo group;

further provided that when R1 is imidazolidinedione or 4-pyridinyl R2 is not substituted aryl, thienyl or substituted thienyl.

Suitably, the invention relates to a compound of formula (I) or a pharmaceutically acceptable salt thereof.

This invention also relates to a method of treating cancer, which comprises administering to a subject in need thereof an effective amount of a compound of Formula (I).

This invention also relates to a method of treating one or more disease states selected from: autoimmune disorders, inflammatory diseases, cardiovascular diseases, neurodegenerative diseases, allergy, asthma, pancreatitis, multiorgan failure, kidney diseases, platelet aggregation, sperm motility, transplantation rejection, graft rejection and lung injuries, which comprises administering to a subject in need thereof an effective amount of a compound of Formula (I).

Included in the present invention are methods of co-administering the present PI3 kinase inhibiting compounds with further active ingredients.

DETAILED DESCRIPTION OF THE INVENTION

This invention relates to novel compounds of Formula (I) as described above.

Suitably, this invention relates to novel compounds of Formula (I)(A):

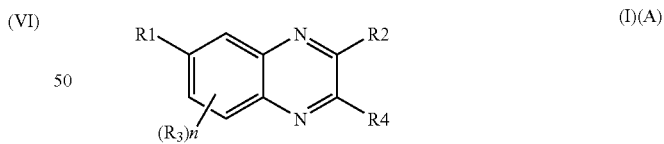
(I)(A)

in which

R1 is an optionally substituted ring system selected from a group consisting of: formula (II), (III), (IV), (V), (VI), (VII) and (VIII):

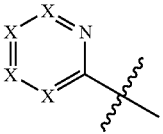
(II)

-continued

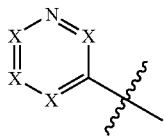
(III)

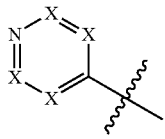
(IV)

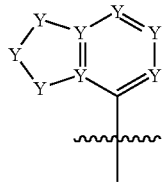
(V)

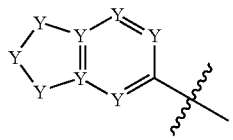
(VI)

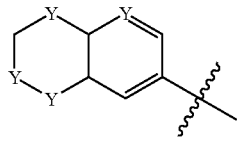
(VII)

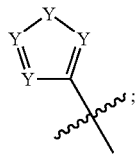
(VIII)

;

each R3 and R4 is independently selected from a group consisting of: hydrogen, halogen, acyl, amino, substituted amino, C1-6alkyl, substituted C1-6alkyl, C3-7cycloalkyl, substituted C3-7cycloalkyl, C3-7heterocycloalkyl, substituted C3-7heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, acyloxy, and aryloxy;

R2 is selected from a group consisting of: aryl, heteroaryl, substituted heteroaryl, substituted aryl, heterocycloalkyl, substituted heterocycloalkyl, amino, substituted amino, arylamino, acylamino, heterocycloalkylamino, hydroxyl, alkoxy;

n is 0-2;

X is C or N; Y is C, O, N or S;

and/or a pharmaceutically acceptable salt, hydrate, solvate or pro-drug thereof;

provided that in each of formula (V) to (VIII) at least one Y is not carbon;

further provided that formula (VIII) is substituted with at least one oxo group;

further provided that R1 is not imidazolidinedione, and when R1 is 4-pyridinyl R2 is not aryl, substituted aryl, thienyl or substituted thienyl.

Suitably, this invention relates to novel compounds of Formula (I)(B):

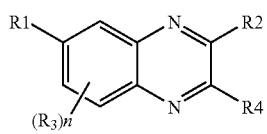
(I)(B)

in which

R1 is an optionally substituted ring system selected from a group consisting of: formula (II), (III), (IV), (V), (VI), (VII) and (VIII):

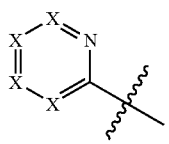
(II)

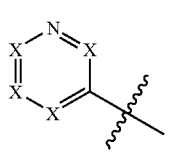
(III)

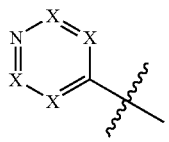
(IV)

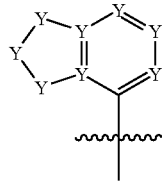
(V)

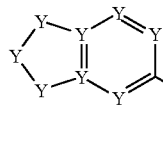
(VI)

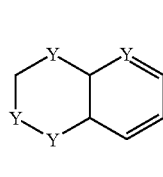
(VII)

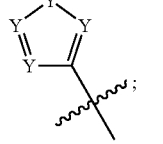
(VIII)

;

each R3 and R4 is independently selected from a group consisting of: hydrogen, halogen, acyl, amino, substituted amino, C1-6alkyl, substituted C1-6alkyl, C3-7cycloalkyl, substituted C3-7cycloalkyl, C3-7heterocycloalkyl, substituted C3-7heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, acyloxy, and aryloxy;

R2 is selected from a group consisting of: heteroaryl, substituted heteroaryl, heterocycloalkyl, substituted heterocycloalkyl, amino, substituted amino, arylamino, acylamino, heterocycloalkylamino, hydroxyl, alkyl, substituted alkyl;

n is 0-2;

X is C or N; Y is C, O, N or S;

and/or a pharmaceutically acceptable salt, hydrate, solvate or pro-drug thereof;

provided that in each of formula (V) to (VIII) at least one Y is not carbon;

further provided that formula (VIII) is substituted with at least one oxo group;

further provided that R1 is not imidazolidinedione, R2 is not thienyl or substituted thienyl.

Suitably, this invention relates to novel compounds of Formula (I)(C):

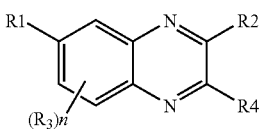

in which

R1 is an optionally substituted ring system selected from a group consisting of: formula (II), (III), and (IV) as defined above;

R3 and R4 are hydrogens;

R2 is selected from a group consisting of: aryl, substituted aryl, heteroaryl, substituted heteroaryl, heterocycloalkyl, substituted heterocycloalkyl, amino, substituted amino, arylamino, acylamino, heterocycloalkylamino, hydroxyl, alkoxy;

n is 0-2;

X is C or N; Y is C, O, N or S;

and/or a pharmaceutically acceptable salt, hydrate, solvate or pro-drug thereof;

provided that R1 is not imidazolidinedione and when R1 is 4-pyridine R2 is not aryl, substituted aryl, thienyl or substituted thienyl.

Suitably, this invention relates to novel compounds of Formula (I)(D):

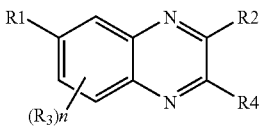

in which

R1 is an optionally substituted ring system selected from a group consisting of: formula (II), (III), and (IV) as defined above;

R3 and R4 are hydrogens;

R2 is selected from a group consisting of: heteroaryl, substituted heteroaryl, heterocycloalkyl, substituted heterocycloalkyl, amino, substituted amino, arylamino, acylamino, heterocycloalkylamino, hydroxyl;

n is 0-2;

X is C or N; Y is C, O, N or S;

and/or a pharmaceutically acceptable salt, hydrate, solvate or pro-drug thereof;

provided that R1 is not imidazolidinedione and R2 is not thienyl or substituted thienyl.

Suitably, this invention relates to compounds of formula (I)(A), wherein R1 is an optionally substituted six-membered heteroaryl ring containing at least one nitrogen.

Suitably, this invention relates to novel compounds of Formula (I)(E):

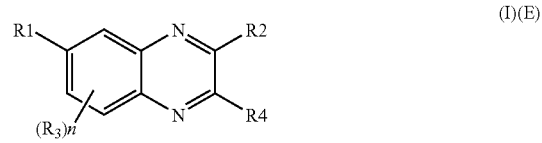

in which

R1 is an optionally substituted ring system selected from a group consisting of: formula (II), (III), and (IV) as defined above;

R4 is hydrogen;

R2 is selected from a group consisting of: heteroaryl, substituted heteroaryl, heterocycloalkyl, substituted heterocycloalkyl, amino, arylamino, acylamino, heterocycloalkylamino, substituted amino, alkoxy, C1-6alkyl and substituted C1-6alkyl;

n is 0;

X is C or N;

or a pharmaceutically acceptable salt thereof;

provided that R2 is not thienyl or substituted thienyl.

Suitably, this invention relates to novel compounds of Formula (I)(F):

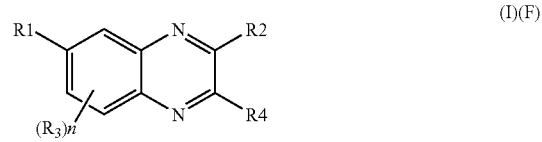

in which

R1 is an optionally substituted pyridinyl ring;

R4 is hydrogen;

R2 is selected from a group consisting of: heteroaryl, substituted heteroaryl, heterocycloalkyl, substituted heterocycloalkyl, amino, substituted amino, arylamino, acylamino, heterocycloalkylamino, alkoxy, C1-6alkyl and substituted C1-6alkyl;

n is 0;

or a pharmaceutically acceptable salt thereof;

provided that R2 is not thienyl or substituted thienyl.

Suitably, this invention relates to novel compounds of Formula (I)(G):

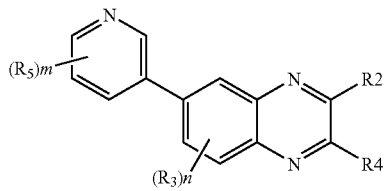

in which each R2, R3, R4 and R5 is independently selected from: hydrogen, halogen, acyl, amino, substituted amino, arylamino, acylamino, heterocycloalkylamino, C1-6alkyl, substituted C1-6alkyl, C3-7cycloalkyl, substituted C3-7cycloalkyl, C3-7heterocycloalkyl, substituted C3-7heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, acyloxy, and aryloxy;

or R5 is R6, wherein R6 is —SO2NR80 or —NSO$_2$R80, in which R80 is selected from a group consisting of: C1-C6alkyl, C1-C6cycloalkyl, C1-C6heterocycloalkyl, substituted C1-C6alkyl, substituted C1-C6cycloalkyl, substituted C1-C6heterocycloalkyl, aryl optionally fused with a five-membered ring or substituted with one to five groups selected from a group consisting of: C1-C6alkyl, C1-C6cycloalkyl, halogen, amino, substituted amino, trifluoromethyl, cyano, hydroxyl, alkoxy, oxo or —(CH$_2$)$_n$COOH, or heteroaryl optionally fused with a five-membered ring or substituted with one to five groups selected from a group consisting of: C1-C6alkyl, C1-C6cycloalkyl, halogen, amino, trifluoromethyl, cyano, hydroxyl, alkoxy, oxo, or —(CH$_2$)$_n$COOH, n is 0-2, m is 0-3;

or a pharmaceutically acceptable salt thereof;

provided that R2 is not thienyl or substituted thienyl.

Suitably, this invention relates to novel compounds of Formula (I)(H):

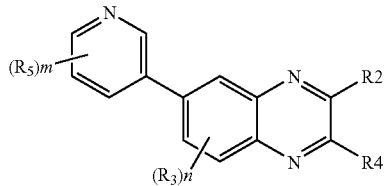

in which

R2 is selected from a group consisting of: heteroaryl, substituted heteroaryl, heterocycloalkyl, substituted heterocycloalkyl, amino, substituted amino, arylamino, acylamino, heterocycloalkylamino, alkoxy, C1-6alkyl and substituted C1-6alkyl;

each R3 and R4 is independently selected from: hydrogen, halogen, acyl, amino, substituted amino, C1-6alkyl, substituted C1-6alkyl, C3-7cycloalkyl, substituted C3-7cycloalkyl, C3-7heterocycloalkyl, substituted C3-7heterocycloalkyl, cyano, hydroxyl and alkoxy;

each R5 is independently selected from: hydrogen, halogen, acyl, amino, substituted amino, C1-6alkyl, substituted C1-6alkyl, C3-7cycloalkyl, substituted C3-7cycloalkyl, C3-7heterocycloalkyl, substituted C3-7heterocycloalkyl, cyano, hydroxyl and alkoxy; or R5 is R6, wherein R6 is —SO2NR80 or —NSO$_2$R80, in which R80 is selected from a group consisting of: C1-C6alkyl, C1-C6cycloalkyl, C1-C6heterocycloalkyl, substituted C1-C6alkyl, substituted C1-C6cycloalkyl, substituted C1-C6heterocycloalkyl, aryl optionally fused with a five-membered ring or substituted with one to five groups selected from a group consisting of: C1-C6alkyl, C1-C6cycloalkyl, halogen, amino, substituted amino, trifluoromethyl, cyano, hydroxyl, alkoxy, oxo or —(CH$_2$)$_n$COOH, or heteroaryl optionally fused with a five-membered ring or substituted with one to five groups selected from a group consisting of: C1-C6alkyl, C1-C6cycloalkyl, halogen, amino, trifluoromethyl, cyano, hydroxyl, alkoxy, oxo, or —(CH$_2$)$_n$COOH;

n is 0-2, m is 0-2;

or a pharmaceutically acceptable salt thereof;

provided that R2 is not thienyl or substituted thienyl.

Suitably, this invention relates to novel compounds of Formula (I)(J):

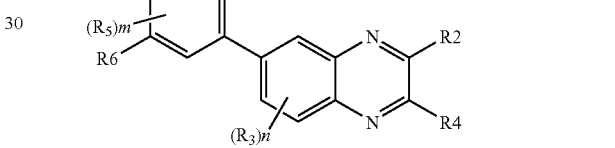

in which

R2 is selected from a group consisting of: heteroaryl, substituted heteroaryl, heterocycloalkyl, substituted heterocycloalkyl, amino, substituted amino, arylamino, acylamino, heterocycloalkylamino, alkoxy, C1-6alkyl and substituted C1-6alkyl;

each R3 and R4 is independently selected from: hydrogen, halogen, acyl, amino, substituted amino, C1-6alkyl, substituted C1-6alkyl, C3-7cycloalkyl, substituted C3-7cycloalkyl, C3-7heterocycloalkyl, substituted C3-7heterocycloalkyl, cyano, hydroxyl and alkoxy;

each R5 is independently selected from: hydrogen, halogen, acyl, amino, substituted amino, C1-6alkyl, substituted C1-6alkyl, C3-7cycloalkyl, substituted C3-7cycloalkyl, C3-7heterocycloalkyl, substituted C3-7heterocycloalkyl, cyano, hydroxyl, alkoxy, nitro;

R6 is —SO$_2$NR80 or —NSO$_2$R80, in which R80 is selected from a group consisting of: C1-C6alkyl, C1-C6cycloalkyl, C1-C6heterocycloalkyl, substituted C1-C6alkyl, substituted C1-C6cycloalkyl, substituted C1-C6heterocycloalkyl, aryl optionally fused with a five-membered ring or substituted with one to five groups selected from a group consisting of: C1-C6alkyl, C1-C6cycloalkyl, halogen, amino, substituted amino, trifluoromethyl, cyano, hydroxyl, alkoxy, oxo or —(CH$_2$)$_n$COOH, or heteroaryl optionally fused with a five-membered ring or substituted with one to five groups selected from a group consisting of: C1-C6alkyl, C1-C6cycloalkyl, halogen, amino, trifluoromethyl, cyano, hydroxyl, alkoxy, oxo, or —(CH$_2$)$_n$COOH;

n is 0-2, m is 0-2;
or a pharmaceutically acceptable salt thereof.

Suitably, this invention relates to novel compounds of Formula (I)(K):

(I)(K)

in which
R2 is selected from a group consisting of: heteroaryl, substituted heteroaryl, heterocycloalkyl, substituted heterocycloalkyl, amino, substituted amino, arylamino, acylamino, heterocycloalkylamino, alkoxy, C1-6alkyl and substituted C1-6alkyl;
R4 is hydrogen;
each R5 is independently selected from: hydrogen, halogen, acyl, amino, substituted amino, C1-6alkyl, substituted C1-6alkyl, cyano, hydroxyl, alkoxy;
n is 0, m is 0-1;
R6 is —SO$_2$NR80 or —NSO$_2$R80, in which R80 is selected from a group consisting of: C1-C6alkyl, C1-C6cycloalkyl, C1-C6heterocycloalkyl, substituted C1-C6alkyl, substituted C1-C6cycloalkyl, substituted C1-C6heterocycloalkyl, aryl optionally fused with a five-membered ring or substituted with one to five groups selected from a group consisting of: C1-C6alkyl, C1-C6cycloalkyl, halogen, amino, substituted amino, trifluoromethyl, cyano, hydroxyl, alkoxy, oxo or —(CH$_2$)$_n$COOH, or heteroaryl optionally fused with a five-membered ring or substituted with one to five groups selected from a group consisting of: C1-C6alkyl, C1-C6cycloalkyl, halogen, amino, trifluoromethyl, cyano, hydroxyl, alkoxy, oxo, or —(CH$_2$)$_n$COOH, wherein n is 0-2;
or a pharmaceutically acceptable salt thereof.

Suitably, this invention relates to novel compounds of Formula (I)(L):

(I)(L)

in which
R2 is selected from a group consisting of: heteroaryl, substituted heteroaryl, heterocycloalkyl, substituted heterocycloalkyl, amino, substituted amino, arylamino, acylamino, heterocycloalkylamino, alkoxy, C1-6alkyl and substituted C1-6alkyl;
each R5 is independently selected from: hydrogen, halogen, acyl, amino, substituted amino, C1-6alkyl, substituted C1-6alkyl, cyano, hydroxyl, alkoxy;
m is 0-1;
R6 is —SO$_2$NR80 or —NSO$_2$R80, wherein R80 is selected from a group consisting of: C1-C6alkyl, C1-C6cycloalkyl, C1-C6heterocycloalkyl, substituted C1-C6alkyl, substituted C1-C6cycloalkyl, substituted C1-C6heterocycloalkyl, aryl optionally fused with a five-membered ring or substituted with one to five groups selected from a group consisting of: C1-C6alkyl, C1-C6cycloalkyl, halogen, amino, substituted amino, trifluoromethyl, cyano, hydroxyl, alkoxy, oxo or —(CH$_2$)$_n$COOH, or heteroaryl optionally fused with a five-membered ring or substituted with one to five groups selected from a group consisting of: C1-C6alkyl, C1-C6cycloalkyl, halogen, amino, trifluoromethyl, cyano, hydroxyl, alkoxy, oxo, or —(CH$_2$)$_n$COOH;
or a pharmaceutically acceptable salt thereof.

Suitably, this invention relates to novel compounds of Formula (I)(M):

(I)(M)

in which
R2 is selected from a group consisting of: heteroaryl, substituted heteroaryl, heterocycloalkyl, substituted heterocycloalkyl, amino, substituted amino, arylamino, acylamino, heterocycloalkylamino, alkoxy, C1-6alkyl and substituted C1-6alkyl;
each R5 is independently selected from: hydrogen, halogen, acyl, amino, substituted amino, C1-6alkyl, substituted C1-6alkyl, cyano, hydroxyl, alkoxy;
m is 0-1;
R6 is —NSO$_2$R80, wherein R80 is selected from a group consisting of: C1-C6alkyl, C1-C6cycloalkyl, C1-C6heterocycloalkyl, substituted C1-C6alkyl, substituted C1-C6cycloalkyl, substituted C1-C6heterocycloalkyl, aryl optionally fused with a five-membered ring or substituted with one to five groups selected from a group consisting of: C1-C6alkyl, C1-C6cycloalkyl, halogen, amino, substituted amino, trifluoromethyl, cyano, hydroxyl, alkoxy, oxo or —(CH$_2$)$_n$COOH, or heteroaryl optionally fused with a five-membered ring or substituted with one to five groups selected from a group consisting of: C1-C6alkyl, C1-C6cycloalkyl, halogen, amino, trifluoromethyl, cyano, hydroxyl, alkoxy, oxo, or —(CH$_2$)$_n$COOH, wherein n is 0-2;
or a pharmaceutically acceptable salt thereof.

Suitably, this invention relates to novel compounds of Formula (I)(N):

(I)(N)

in which
R2 is selected from a group consisting of: heteroaryl, substituted heteroaryl, heterocycloalkyl, substituted heterocycloalkyl, amino, substituted amino, arylamino, acylamino, heterocycloalkylamino, alkoxy, C1-6alkyl and substituted C1-6alkyl;

each R5 is independently selected from: hydrogen, halogen, acyl, amino, substituted amino, C1-6alkyl, substituted C1-6alkyl, cyano, hydroxyl, alkoxy;

m is 0-1;

R6 is —SO$_2$NR80, wherein R80 is selected from a group consisting of: C1-C6alkyl, C1-C6cycloalkyl, C1-C6heterocycloalkyl, substituted C1-C6alkyl, substituted C1-C6cycloalkyl, substituted C1-C6heterocycloalkyl, aryl optionally fused with a five-membered ring or substituted with one to five groups selected from a group consisting of: C1-C6alkyl, C1-C6cycloalkyl, halogen, amino, substituted amino, trifluoromethyl, cyano, hydroxyl, alkoxy, oxo or —(CH$_2$)$_n$COOH, or heteroaryl optionally fused with a five-membered ring or substituted with one to five groups selected from a group consisting of: C1-C6alkyl, C1-C6cycloalkyl, halogen, amino, trifluoromethyl, cyano, hydroxyl, alkoxy, oxo, or —(CH$_2$)$_n$COOH, wherein n is 0-2;

or a pharmaceutically acceptable salt thereof.

Suitably, this invention relates to compounds of Formulas (I)M and (I)(N), wherein R2 is selected from the group consisting of: optionally substituted piperazine, optionally substituted pyrazole, substituted amino and optionally substituted piperidine;

R80 is selected from a group consisting of: C1-C6alkyl, C1-C6cycloalkyl, C1-C6heterocycloalkyl, substituted C1-C6alkyl, substituted C1-C6cycloalkyl, substituted C1-C6heterocycloalkyl, aryl and substituted aryl.

Suitably, this invention relates to compounds of Formulas (I)M and (I)(N), wherein R2 is selected from the group consisting of: optionally substituted piperazine, optionally substituted pyrazole, substituted amino and optionally substituted piperidine;

R80 is selected from a group consisting of: aryl optionally substituted with one to five groups selected from a group consisting of: C1-C6alkyl, C1-C6cycloalkyl, halogen, amino, substituted amino, trifluoromethyl, cyano, hydroxyl, alkoxy, oxo or —(CH$_2$)$_n$COOH, or heteroaryl optionally substituted with one to five groups selected from a group consisting of: C1-C6alkyl, C1-C6cycloalkyl, halogen, amino, trifluoromethyl, cyano, hydroxyl, alkoxy, oxo, or —(CH$_2$)$_n$COOH, wherein n is 0-2.

Suitably, this invention relates to the following compounds:

5-[3-(4-pyridinyl)-6-quinoxalinyl]-3-pyridinesulfonamide;
2-amino-N,N-dimethyl-5-[3-(4-pyridinyl)-6-quinoxalinyl]-3-pyridinesulfonamide;
5-[3-(3-pyridinyl)-6-quinoxalinyl]-3-pyridinesulfonamide;
5-(3-phenyl-6-quinoxalinyl)-3-pyridinesulfonamide;
7-[6-(methyloxy)-3-pyridinyl]-2-(4-morpholinyl)quinoxaline;
2-(4-morpholinyl)-7-[4-(4-pyridinyl)-6-quinolinyl]quinoxaline;
2-(4-morpholinyl)-7-(1H-pyrrolo[2,3-b]pyridin-5-yl)quinoxaline;
7-(1H-indazol-5-yl)-2-(4-morpholinyl)quinoxaline;
2-(4-morpholinyl)-7-(4-pyridinyl)quinoxaline;
2-(4-morpholinyl)-7-(3-pyridinyl)quinoxaline;
7-[2-(methyloxy)-3-pyridinyl]-2-(4-morpholinyl)quinoxaline;
7-(1H-pyrrolo[2,3-b]pyridin-5-yl)-2(1H)-quinoxalinone;
ethyl 1-[7-(1H-pyrrolo[2,3-b]pyridin-5-yl)-2-quinoxalinyl]-3-piperidinecarboxylate;
2-(4-morpholinyl)-7-(1H-pyrazolo[3,4-b]pyridin-5-yl)quinoxaline;
2-(4-pyridinyl)-7-(1H-pyrrolo[2,3-b]pyridin-5-yl)quinoxaline;
2-amino-N,N-dimethyl-5-[3-(4-morpholinyl)-6-quinoxalinyl]-3-pyridinesulfonamide;
2-(4-morpholinyl)-7-[5-(4-morpholinylsulfonyl)-3-pyridinyl]quinoxaline;
5-[3-(4-morpholinyl)-6-quinoxalinyl]-3-pyridinesulfonamide;
2-amino-N,N-dimethyl-5-(3-oxo-3,4-dihydro-6-quinoxalinyl)-3-pyridinesulfonamide;
2-amino-N,N-dimethyl-5-(3-{[2-(4-morpholinyl)ethyl]amino}-6-quinoxalinyl)-3-pyridinesulfonamide;
2-amino-5-{3-[[2-(dimethylamino)ethyl](methyl)amino]-6-quinoxalinyl}-N,N-dimethyl-3-pyridinesulfonamide;
2-amino-N,N-dimethyl-5-(3-{[2-(methyloxy)ethyl]amino}-6-quinoxalinyl)-3-pyridinesulfonamide;
2-amino-5-{7-[6-(methyloxy)-3-pyridinyl]-2-quinoxalinyl}-3-pyridinesulfonamide;
2-amino-5-{3-[(2-hydroxyethyl)(methyl)amino]-6-quinoxalinyl}-N,N-dimethyl-3-pyridinesulfonamide;
2-amino-5-[3-(ethylamino)-6-quinoxalinyl]-N,N-dimethyl-3-pyridinesulfonamide;
2-amino-N,N-dimethyl-5-[3-(4-methyl-1-piperazinyl)-6-quinoxalinyl]-3-pyridinesulfonamide;
5-(3-{[2-(2-pyridinyl)ethyl]amino}-6-quinoxalinyl)-3-pyridinesulfonamide;
5-{3-[4-(methylsulfonyl)-1-piperazinyl]-6-quinoxalinyl}-3-pyridinesulfonamide;
5-[3-(1-piperidinyl)-6-quinoxalinyl]-3-pyridinesulfonamide;
5-[3-(4-hydroxy-1-piperidinyl)-6-quinoxalinyl]-3-pyridinesulfonamide;
5-[3-(2,6-dimethyl-4-morpholinyl)-6-quinoxalinyl]-3-pyridinesulfonamide;
1,1-dimethylethyl 4-{7-[5-(aminosulfonyl)-3-pyridinyl]-2-quinoxalinyl}-1-piperazinecarboxylate;
5-{3-[(2,2-dimethylpropyl)amino]-6-quinoxalinyl}-3-pyridinesulfonamide;
5-[3-(1-piperazinyl)-6-quinoxalinyl]-3-pyridinesulfonamide;
1,1-dimethylethyl {2-[{7-[5-(aminosulfonyl)-3-pyridinyl]-2-quinoxalinyl}(methyl)amino]ethyl}carbamate;
5-[3-(4-acetyl-1-piperazinyl)-6-quinoxalinyl]-3-pyridinesulfonamide;
5-{3-[4-(2-hydroxyethyl)-1-piperazinyl]-6-quinoxalinyl}-3-pyridinesulfonamide;
5-{3-[4-(2-furanylcarbonyl)-1-piperazinyl]-6-quinoxalinyl}-3-pyridinesulfonamide;
5-(3-{4-[2-(4-morpholinyl)ethyl]-1-piperazinyl}-6-quinoxalinyl)-3-pyridinesulfonamide;
5-{3-[4-(2-methylpropanoyl)-1-piperazinyl]-6-quinoxalinyl}-3-pyridinesulfonamide;
5-{3-[(1,1-dimethylethyl)amino]-6-quinoxalinyl}-3-pyridinesulfonamide;
N-(2,4-difluorophenyl)-5-{3-[4-(dimethylamino)-1-piperidinyl]-6-quinoxalinyl}-3-pyridinesulfonamide;
N-{2-chloro-5-[3-(4-methyl-1-piperazinyl)-6-quinoxalinyl]-3-pyridinyl}benzenesulfonamide;
N-(5-{3-[4-(methylsulfonyl)-1-piperazinyl]-6-quinoxalinyl}-3-pyridinyl)methanesulfonamide;
N-{5-[3-(4-morpholinyl)-6-quinoxalinyl]-3-pyridinyl}cyclopropanesulfonamide;
2-methyl-N-(5-{3-[4-(methylsulfonyl)-1-piperazinyl]-6-quinoxalinyl}-3-pyridinyl)benzenesulfonamide;

N-(2,4-difluorophenyl)-5-[3-(4-morpholinyl)-6-quinoxalinyl]-3-pyridinesulfonamide;
3-{7-[5-(aminosulfonyl)-3-pyridinyl]-2-quinoxalinyl}-N-methylbenzamide;
5-(3-{3-[(methylamino)sulfonyl]phenyl}-6-quinoxalinyl)-3-pyridinesulfonamide;
5-[3-(1H-pyrazol-4-yl)-6-quinoxalinyl]-3-pyridinesulfonamide;
5-[3-(1H-pyrazol-3-yl)-6-quinoxalinyl]-3-pyridinesulfonamide;
N-{2-chloro-5-[3-(4-methyl-1-piperazinyl)-6-quinoxalinyl]-3-pyridinyl}benzenesulfonamide;
N-{5-[3-(4-methyl-1-piperazinyl)-6-quinoxalinyl]-3-pyridinyl}benzenesulfonamide;
N-(2,4-difluorophenyl)-5-[3-(4-methyl-1-piperazinyl)-6-quinoxalinyl]-3-pyridinesulfonamide;
5-[3-(4-methyl-1-piperazinyl)-6-quinoxalinyl]-3-pyridinamine;
N-{2-methyl-5-[3-(4-methyl-1-piperazinyl)-6-quinoxalinyl]-3-pyridinyl}benzenesulfonamide;
N-(2,4-difluorophenyl)-5-(3-{1-[2-(dimethylamino)ethyl]-1H-pyrazol-4-yl}-6-quinoxalinyl)-3-pyridinesulfonamide;
2,4-difluoro-N-{5-[3-(4-methyl-1-piperazinyl)-6-quinoxalinyl]-3-pyridinyl}benzenesulfonamide;
N-{5-[3-(1-methyl-1H-pyrazol-4-yl)-6-quinoxalinyl]-3-pyridinyl}benzenesulfonamide;
N-{5-[3-(3-furanyl)-6-quinoxalinyl]-3-pyridinyl}benzenesulfonamide;
N-{2-chloro-5-[3-(4-methyl-1-piperazinyl)-6-quinoxalinyl]-3-pyridinyl}-2,4-difluorobenzenesulfonamide;
2,4-difluoro-N-{2-methyl-5-[3-(4-methyl-1-piperazinyl)-6-quinoxalinyl]-3-pyridinyl}benzenesulfonamide;
N-[5-(3-{1-[2-(dimethylamino)ethyl]-1H-pyrazol-4-yl}-6-quinoxalinyl)-3-pyridinyl]benzenesulfonamide;
N-{5-[3-(1-ethyl-1H-pyrazol-4-yl)-6-quinoxalinyl]-3-pyridinyl}benzenesulfonamide;
N-(5-{3-[1-(2-hydroxyethyl)-1H-pyrazol-4-yl]-6-quinoxalinyl}-3-pyridinyl)benzenesulfonamide;
N-{5-[3-(1-methyl-1H-pyrazol-5-yl)-6-quinoxalinyl]-3-pyridinyl}benzenesulfonamide;
N-{5-[3-(1,3,5-trimethyl-1H-pyrazol-4-yl)-6-quinoxalinyl]-3-pyridinyl}benzenesulfonamide;
N-{5-[3-(3,5-dimethyl-4-isoxazolyl)-6-quinoxalinyl]-3-pyridinyl}benzenesulfonamide;
N-(5-{3-[1-(2-methylpropyl)-1H-pyrazol-4-yl]-6-quinoxalinyl}-3-pyridinyl)benzenesulfonamide;
N-[5-(3-{1-[2-(4-morpholinyl)ethyl]-1H-pyrazol-4-yl}-6-quinoxalinyl)-3-pyridinyl]benzenesulfonamide;
N-(5-{3-[1-(phenylsulfonyl)-1H-pyrazol-4-yl]-6-quinoxalinyl}-3-pyridinyl)benzenesulfonamide;
N-{5-[3-(1H-pyrazol-4-yl)-6-quinoxalinyl]-3-pyridinyl}benzenesulfonamide;
[4-(7-{5-[(phenylsulfonyl)amino]-3-pyridinyl}-2-quinoxalinyl)-1H-pyrazol-1-yl]aceti acid;
N-{5-[3-(1-methyl-1H-pyrazol-3-yl)-6-quinoxalinyl]-3-pyridinyl}benzenesulfonamide;
N,N-dimethyl-2-[4-(7-{5-[(phenylsulfonyl)amino]-3-pyridinyl}-2-quinoxalinyl)-1H-pyrazol-1-yl]acetamide;
N-[5-(3-imidazo[1,2-a]pyridin-3-yl-6-quinoxalinyl)-3-pyridinyl]benzenesulfonamide;
2-[4-(7-{5-[(phenylsulfonyl)amino]-3-pyridinyl}-2-quinoxalinyl)-1H-pyrazol-1-yl]acetamide;
N-methyl-1-(7-{5-[(phenylsulfonyl)amino]-3-pyridinyl}-2-quinoxalinyl)-4-piperidinecarboxamide;
N,N-dimethyl-1-(7-{5-[(phenylsulfonyl)amino]-3-pyridinyl}-2-quinoxalinyl)-4-piperidinecarboxamide;
N-(7-{5-[(phenylsulfonyl)amino]-3-pyridinyl}-2-quinoxalinyl)benzamide;
2-phenyl-N-(7-{5-[(phenylsulfonyl)amino]-3-pyridinyl}-2-quinoxalinyl)acetamide;
N-(7-{5-[(phenylsulfonyl)amino]-3-pyridinyl}-2-quinoxalinyl)benzenesulfonamide;
5-[3-(1-methyl-1H-pyrazol-4-yl)-6-quinoxalinyl]-3-pyridinamine;
2-methyl-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}-1-phenylmethanesulfonamide;
N-{2-chloro-5-[3-(1-methyl-1H-pyrazol-4-yl)-6-quinoxalinyl]-3-pyridinyl}cyclopropanesulfonamide;
N-{2-chloro-5-[3-(1-methyl-1H-pyrazol-4-yl)-6-quinoxalinyl]-3-pyridinyl}benzenesulfonamide;
2,4-difluoro-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}-2-propanesulfonamide;
1-methyl-N-{5-[3-(1-methyl-1H-pyrazol-4-yl)-6-quinoxalinyl]-3-pyridinyl}-1H-imidazole-4-sulfonamide;
3-fluoro-N-{5-[3-(1-methyl-1H-pyrazol-4-yl)-6-quinoxalinyl]-3-pyridinyl}benzenesulfonamide;
methyl 4-(methyloxy)-3-[({5-[3-(1-methyl-1H-pyrazol-4-yl)-6-quinoxalinyl]-3-pyridinyl}amino)sulfonyl]benzoate;
4-cyano-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}methanesulfonamide;
1-ethyl-N-{5-[3-(1-methyl-1H-pyrazol-4-yl)-6-quinoxalinyl]-3-pyridinyl}-1H-pyrazole-4-sulfonamide;
1,3-dimethyl-N-{5-[3-(1-methyl-1H-pyrazol-4-yl)-6-quinoxalinyl]-3-pyridinyl}-1H-pyrazole-4-sulfonamide;
N-{5-[3-(1-methyl-1H-pyrazol-4-yl)-6-quinoxalinyl]-3-pyridinyl}cyclopropanesulfonamide;
1-methyl-N-{5-[3-(1-methyl-1H-pyrazol-4-yl)-6-quinoxalinyl]-3-pyridinyl}-1H-pyrazole-3-sulfonamide;
N-{5-[3-(1-methyl-1H-pyrazol-4-yl)-6-quinoxalinyl]-3-pyridinyl}-1-propanesulfonamide;
1-cyclohexyl-N-{5-[3-(1-methyl-1H-pyrazol-4-yl)-6-quinoxalinyl]-3-pyridinyl}methanesulfonamide;
4-fluoro-N-{5-[3-(1-methyl-1H-pyrazol-4-yl)-6-quinoxalinyl]-3-pyridinyl}-3-(trifluoromethyl)benzenesulfonamide;
2,2,2-trifluoro-N-{5-[3-(1-methyl-1H-pyrazol-4-yl)-6-quinoxalinyl]-3-pyridinyl}ethanesulfonamide;
3,5-dimethyl-N-{5-[3-(1-methyl-1H-pyrazol-4-yl)-6-quinoxalinyl]-3-pyridinyl}-4-isoxazolesulfonamide;
1,3,5-trimethyl-N-{5-[3-(1-methyl-1H-pyrazol-4-yl)-6-quinoxalinyl]-3-pyridinyl}-1H-pyrazole-4-sulfonamide;
N-{5-[3-(1-methyl-1H-pyrazol-4-yl)-6-quinoxalinyl]-3-pyridinyl}ethanesulfonamide;
N-{5-[3-(1-methyl-1H-pyrazol-4-yl)-6-quinoxalinyl]-3-pyridinyl}-1-butanesulfonamide;
4-fluoro-N-{5-[3-(1-methyl-1H-pyrazol-4-yl)-6-quinoxalinyl]-3-pyridinyl}benzenesulfonamide;
4-(methyloxy)-3-[({5-[3-(1-methyl-1H-pyrazol-4-yl)-6-quinoxalinyl]-3-pyridinyl}amino)sulfonyl]benzoic acid;
2-methyl-N-{5-[3-(1-methyl-1H-pyrazol-4-yl)-6-quinoxalinyl]-3-pyridinyl}-1-propanesulfonamide;
N-{5-[3-(1-methyl-1H-pyrazol-4-yl)-6-quinoxalinyl]-3-pyridinyl}-2-thiophenesulfonamide;
2-(methyloxy)-N-{5-[3-(1-methyl-1H-pyrazol-4-yl)-6-quinoxalinyl]-3-pyridinyl}benzenesulfonamide;

2-fluoro-N-{5-[3-(1-methyl-1H-pyrazol-4-yl)-6-quinoxalinyl]-3-pyridinyl}benzenesulfonamide;
4-methyl-N-{5-[3-(1-methyl-1H-pyrazol-4-yl)-6-quinoxalinyl]-3-pyridinyl}benzenesulfonamide;
3,4-bis(methyloxy)-N-{5-[3-(1-methyl-1H-pyrazol-4-yl)-6-quinoxalinyl]-3-pyridinyl}benzenesulfonamide;
2,5-dimethyl-N-{5-[3-(1-methyl-1H-pyrazol-4-yl)-6-quinoxalinyl]-3-pyridinyl}benzenesulfonamide;
4-(1-methylethyl)-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}-4-propylbenzenesulfonamide;
4-(methyloxy)-N-{5-[3-(1-methyl-1H-pyrazol-4-yl)-6-quinoxalinyl]-3-pyridinyl}benzenesulfonamide;
2,5-bis(methyloxy)-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}-3-(trifluoromethyl)benzenesulfonamide;
1-cyclopentyl-N-{5-[3-(1-methyl-1H-pyrazol-4-yl)-6-quinoxalinyl]-3-pyridinyl}methanesulfonamide;
3-fluoro-4-(methyloxy)-N-{5-[3-(1-methyl-1H-pyrazol-4-yl)-6-quinoxalinyl]-3-pyridinyl}benzenesulfonamide;
4-fluoro-2-methyl-N-{5-[3-(1-methyl-1H-pyrazol-4-yl)-6-quinoxalinyl]-3-pyridinyl}benzenesulfonamide;
2-fluoro-4-methyl-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}-2-(trifluoromethyl)benzenesulfonamide;
N-{5-[3-(1-methyl-1H-pyrazol-4-yl)-6-quinoxalinyl]-3-pyridinyl}-4-(trifluoromethyl)benzenesulfonamide;
2-chloro-4-fluoro-N-{5-[3-(1-methyl-1H-pyrazol-4-yl)-6-quinoxalinyl]-3-pyridinyl}benzenesulfonamide;
2,5-dichloro-N-{5-[3-(1-methyl-1H-pyrazol-4-yl)-6-quinoxalinyl]-3-pyridinyl}benzenesulfonamide;
2,3-dichloro-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}-3-thiophenesulfonamide;
3-chloro-N-{5-[3-(1-methyl-1H-pyrazol-4-yl)-6-quinoxalinyl]-3-pyridinyl}benzenesulfonamide;
3-(methyloxy)-N-{5-[3-(1-methyl-1H-pyrazol-4-yl)-6-quinoxalinyl]-3-pyridinyl}benzenesulfonamide;
5-chloro-1,3-dimethyl-N-{5-[3-(1-methyl-1H-pyrazol-4-yl)-6-quinoxalinyl]-3-pyridinyl}-1H-pyrazole-4-sulfonamide;
4-[(4-fluorophenyl)oxy]-N-{5-[3-(1-methyl-1H-pyrazol-4-yl)-6-quinoxalinyl]-3-pyridinyl}benzenesulfonamide;
2-chloro-N-{5-[3-(1-methyl-1H-pyrazol-4-yl)-6-quinoxalinyl]-3-pyridinyl}-5-(trifluoromethyl)benzenesulfonamide;
N-{5-[3-(1-methyl-1H-pyrazol-4-yl)-6-quinoxalinyl]-3-pyridinyl}-4-(4-pyridinyloxy)benzenesulfonamide;
N-{5-[3-(1-methyl-1H-pyrazol-4-yl)-6-quinoxalinyl]-3-pyridinyl}-4-(3-pyridinyloxy)benzenesulfonamide;
N-{5-[3-(1-methyl-1H-pyrazol-4-yl)-6-quinoxalinyl]-3-pyridinyl}-4-[(phenylmethyl)oxy]benzenesulfonamide;
N-{5-[3-(1-methyl-1H-pyrazol-4-yl)-6-quinoxalinyl]-3-pyridinyl}-4-(1,3-oxazol-5-yl)benzenesulfonamide;
N-{5-[3-(1-methyl-1H-pyrazol-4-yl)-6-quinoxalinyl]-3-pyridinyl}-4-(methylsulfonyl)benzenesulfonamide;
N-{5-[3-(1-methyl-1H-pyrazol-4-yl)-6-quinoxalinyl]-3-pyridinyl}-4-(phenyloxy)benzenesulfonamide;
4'-chloro-N-{5-[3-(1-methyl-1H-pyrazol-4-yl)-6-quinoxalinyl]-3-pyridinyl}-4-biphenylsulfonamide;
4-{[(2-chloro-1,3-thiazol-5-yl)methyl]oxy}-N-{5-[3-(1-methyl-1H-pyrazol-4-yl)-6-quinoxalinyl]-3-pyridinyl}benzenesulfonamide;
4-{[2-(methyloxy)phenyl]oxy}-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}-4-(2-oxo-1-pyrrolidinyl)benzenesulfonamide;
N-{5-[3-(1-methyl-1H-pyrazol-4-yl)-6-quinoxalinyl]-3-pyridinyl}-4-(2-methyl-1,3-thiazol-4-yl)benzenesulfonamide;
N-{2-(ethyloxy)-5-[({5-[3-(1-methyl-1H-pyrazol-4-yl)-6-quinoxalinyl]-3-pyridinyl}amino)sulfonyl]phenyl}-4-morpholinecarboxamide;
N-{2-(ethyloxy)-5-[({5-[3-(1-methyl-1H-pyrazol-4-yl)-6-quinoxalinyl]-3-pyridinyl}amino)sulfonyl]phenyl}-1-pyrrolidinecarboxamide;
N-{5-[3-(1-methyl-1H-pyrazol-4-yl)-6-quinoxalinyl]-3-pyridinyl}-2,3-dihydro-1,4-benzodioxin-6-sulfonamide;
N-{3-methyl-4-[({5-[3-(1-methyl-1H-pyrazol-4-yl)-6-quinoxalinyl]-3-pyridinyl}amino)sulfonyl]phenyl}-4-morpholinecarboxamide;
4-chloro-N-{4-(ethyloxy)-3-[({5-[3-(1-methyl-1H-pyrazol-4-yl)-6-quinoxalinyl]-3-pyridinyl}amino)sulfonyl]phenyl}benzamide;
2,6-difluoro-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}-2-butanesulfonamide;
2-chloro-6-methyl-N-{5-[3-(1-methyl-1H-pyrazol-4-yl)-6-quinoxalinyl]-3-pyridinyl}benzenesulfonamide;
2-chloro-N-{5-[3-(1-methyl-1H-pyrazol-4-yl)-6-quinoxalinyl]-3-pyridinyl}benzenesulfonamide;
4-chloro-N-{5-[3-(1-methyl-1H-pyrazol-4-yl)-6-quinoxalinyl]-3-pyridinyl}benzenesulfonamide;
N-{5-[3-(1-methyl-1H-pyrazol-4-yl)-6-quinoxalinyl]-3-pyridinyl}-2,1,3-benzoxadiazole-4-sulfonamide;
N-{2-(methyloxy)-5-[3-(1-methyl-1H-pyrazol-4-yl)-6-quinoxalinyl]-3-pyridinyl}benzenesulfonamide;
4-methyl-N-{5-[3-(1-methyl-1H-pyrazol-4-yl)-6-quinoxalinyl]-3-pyridinyl}-3,4-dihydro-2H-1,4-benzoxazine-7-sulfonamide;
2-amino-N,N-dimethyl-5-[3-(4-pyridinyl)-6-quinoxalinyl]-3-pyridinesulfonamide;
3,3'-di-4-morpholinyl-6,6'-biquinoxaline;
N,N-dimethyl-N'-{5-[3-(1-methyl-1H-pyrazol-4-yl)-6-quinoxalinyl]-3-pyridinyl}sulfamide;
N-{2-(methyloxy)-5-[3-(1-methyl-1H-pyrazol-4-yl)-6-quinoxalinyl]-3-pyridinyl}cyclopropanesulfonamide;
2,4-difluoro-N-{2-(methyloxy)-5-[3-(1-methyl-1H-pyrazol-4-yl)-6-quinoxalinyl]-3-pyridinyl}benzenesulfonamide;
N-{2-(methyloxy)-5-[3-(1-methyl-1H-pyrazol-4-yl)-6-quinoxalinyl]-3-pyridinyl}methanesulfonamide;
2,4-difluoro-N-{2-methyl-5-[3-(1-methyl-1H-pyrazol-4-yl)-6-quinoxalinyl]-3-pyridinyl}benzenesulfonamide;
N-{2-methyl-5-[3-(1-methyl-1H-pyrazol-4-yl)-6-quinoxalinyl]-3-pyridinyl}cyclopropanesulfonamide;
1-ethyl-N-{2-(methyloxy)-5-[3-(1-methyl-1H-pyrazol-4-yl)-6-quinoxalinyl]-3-pyridinyl}-1H-pyrazole-4-sulfonamide;
N-{5-[3-(1-methyl-1H-pyrazol-4-yl)-6-quinoxalinyl]-3-pyridinyl}-4-morpholinesulfonamide;
1,1-dimethylethyl [2-(4-{7-[5-(aminosulfonyl)-3-pyridinyl]-2-quinoxalinyl}-1-piperazinyl)ethyl]carbamate;
5-(3-{[2-(dimethylamino)ethyl]oxy}-6-quinoxalinyl)-3-pyridinesulfonamide;
5-{3-[[3-(dimethylamino)propyl](methyl)amino]-6-quinoxalinyl}-3-pyridinesulfonamide;
5-(3-{4-[3-(methyloxy)phenyl]-1-piperazinyl}-6-quinoxalinyl)-3-pyridinesulfonamide;

5-{3-[4-(4-acetylphenyl)-1-piperazinyl]-6-quinoxalinyl}-3-pyridinesulfonamide;
5-[3-(4-phenyl-1-piperazinyl)-6-quinoxalinyl]-3-pyridinesulfonamide;
5-(3-{4-[4-(methyloxy)phenyl]-1-piperazinyl}-6-quinoxalinyl)-3-pyridinesulfonamide;
5-(3-{4-[2-(methyloxy)phenyl]-1-piperazinyl}-6-quinoxalinyl)-3-pyridinesulfonamide;
N-(2,4-difluorophenyl)-5-(3-{4-[3-(4-morpholinyl)-4-nitrophenyl]-1-piperazinyl}-6-quinoxalinyl)-3-pyridinesulfonamide;
N-(2,4-difluorophenyl)-5-{3-[4-(dimethylamino)-1-piperidinyl]-6-quinoxalinyl}-3-pyridinesulfonamide;
N-(2,4-difluorophenyl)-5-[3-(dimethylamino)-6-quinoxalinyl]-3-pyridinesulfonamide;
N-(2,4-difluorophenyl)-5-{3-[methyl(phenyl)amino]-6-quinoxalinyl}-3-pyridinesulfonamide;
N-(2,4-difluorophenyl)-5-[3-(phenyloxy)-6-quinoxalinyl]-3-pyridinesulfonamide;
N-(2,4-difluorophenyl)-5-(3-{4-[(1-methyl-1H-pyrazol-4-yl)methyl]-1-piperazinyl}-6-quinoxalinyl)-3-pyridinesulfonamide;
N-(2,4-difluorophenyl)-5-{3-[4-(3-pyridinylmethyl)-1-piperazinyl]-6-quinoxalinyl}-3-pyridinesulfonamide;
N-(2,4-difluorophenyl)-5-{3-[4-(4-pyridinylmethyl)-1-piperazinyl]-6-quinoxalinyl}-3-pyridinesulfonamide;
N-{2-chloro-5-[3-(phenylamino)-6-quinoxalinyl]-3-pyridinyl}benzenesulfonamide;
N-(2-chloro-5-{3-[3-(dimethylamino)-1-piperidinyl]-6-quinoxalinyl}-3-pyridinyl)benzenesulfonamide;
N-(2-chloro-5-{3-[3-(hydroxymethyl)-1-pyrrolidinyl]-6-quinoxalinyl}-3-pyridinyl)benzenesulfonamide;
N-(2-chloro-5-{3-[4-(dimethylamino)-1-piperidinyl]-6-quinoxalinyl}-3-pyridinyl)benzenesulfonamide;
N-[2-chloro-5-(3-{4-[(dimethylamino)methyl]-1-piperidinyl}-6-quinoxalinyl)-3-pyridinyl]benzenesulfonamide;
N-(2-chloro-5-{3-[3-(dimethylamino)-1-pyrrolidinyl]-6-quinoxalinyl}-3-pyridinyl)benzenesulfonamide;
N-(5-{3-[4-(dimethylamino)-1-piperidinyl]-6-quinoxalinyl}-3-pyridinyl)benzenesulfonamide;
N-{2-chloro-5-[3-(4-oxo-1-piperidinyl)-6-quinoxalinyl]-3-pyridinyl}benzenesulfonamide;
N-[2-chloro-5-(3-{4-[[2-(dimethylamino)ethyl](methyl)amino]-1-piperidinyl}-6-quinoxalinyl)-3-pyridinyl]benzenesulfonamide;
N-{2-chloro-5-[3-(4-phenyl-1-piperazinyl)-6-quinoxalinyl]-3-pyridinyl}benzenesulfonamide;
N-(5-{3-[4-(4-acetylphenyl)-1-piperazinyl]-6-quinoxalinyl}-2-chloro-3-pyridinyl)benzenesulfonamide;
N-[2-chloro-5-(3-{4-[4-(methyloxy)phenyl]-1-piperazinyl}-6-quinoxalinyl)-3-pyridinyl]benzenesulfonamide;
N-{5-[3-(4-acetyl-1-piperazinyl)-6-quinoxalinyl]-2-chloro-3-pyridinyl}benzenesulfonamide;
N-{2-chloro-5-[3-(3-oxo-1-piperazinyl)-6-quinoxalinyl]-3-pyridinyl}benzenesulfonamide;
1,1-dimethylethyl 4-(7-{6-chloro-5-[(phenylsulfonyl)amino]-3-pyridinyl}-2-quinoxalinyl)-1-piperazinecarboxylate;
N-{2-chloro-5-[3-(1-piperazinyl)-6-quinoxalinyl]-3-pyridinyl}benzenesulfonamide;
N-{5-[3-(4-morpholinyl)-6-quinoxalinyl]-3-pyridinyl}benzenesulfonamide;
N-(2-chloro-5-{3-[4-(methylsulfonyl)-1-piperazinyl]-6-quinoxalinyl}-3-pyridinyl)benzenesulfonamide;
N-[5-(3-{4-[2-(methyloxy)phenyl]-1-piperazinyl}-6-quinoxalinyl)-3-pyridinyl]benzenesulfonamide;
N-[5-(3-{3-[4-(methyloxy)phenyl]-1-pyrrolidinyl}-6-quinoxalinyl)-3-pyridinyl]benzenesulfonamide;
N-[5-(3-{4-[3-(methyloxy)phenyl]-1-piperazinyl}-6-quinoxalinyl)-3-pyridinyl]benzenesulfonamide;
N-[5-(3-{3-[3-(methyloxy)phenyl]-1-pyrrolidinyl}-6-quinoxalinyl)-3-pyridinyl]benzenesulfonamide;
N-{5-[3-(4-oxo-1-piperidinyl)-6-quinoxalinyl]-3-pyridinyl}benzenesulfonamide;
N-[5-(3-{4-[4-(methyloxy)phenyl]-1-piperazinyl}-6-quinoxalinyl)-3-pyridinyl]benzenesulfonamide;
N-{5-[3-(4-{[4-(methyloxy)phenyl]sulfonyl}-1-piperazinyl)-6-quinoxalinyl]-3-pyridinyl}benzenesulfonamide;
N-{5-[3-(4-{[4-(methyloxy)phenyl]carbonyl}-1-piperazinyl)-6-quinoxalinyl]-3-pyridinyl}benzenesulfonamide;
N-(5-{3-[4-(4-methyl-1-piperazinyl)-1-piperidinyl]-6-quinoxalinyl}-3-pyridinyl)benzenesulfonamide;
N-(2-chloro-5-{3-[3-(hydroxymethyl)-1-pyrrolidinyl]-6-quinoxalinyl}-3-pyridinyl)benzenesulfonamide;
N-(2-chloro-5-{3-[3-(hydroxymethyl)-1-pyrrolidinyl]-6-quinoxalinyl}-3-pyridinyl)benzenesulfonamide;
(3Z)-N-(5-{3-[(1-methyl-1H-pyrazol-3-yl)amino]-6-quinoxalinyl}-3-pyridinyl)-1,3-pentadiene-2-sulfonamide;
N-(5-{3-[(1-methyl-1H-pyrazol-5-yl)amino]-6-quinoxalinyl}-3-pyridinyl)benzenesulfonamide;
N-[5-(3-{[(1-methyl-1H-pyrazol-4-yl)methyl]amino}-6-quinoxalinyl)-3-pyridinyl]benzenesulfonamide;
N-(5-{3-[4-(methylsulfonyl)-1-piperazinyl]-6-quinoxalinyl}-3-pyridinyl)benzenesulfonamide;
N-{5-[3-(4-{[2-(methylsulfonyl)ethyl]amino}-1-piperidinyl)-6-quinoxalinyl]-3-pyridinyl}benzenesulfonamide;
1,1-dimethylethyl 4-(7-{5-[(phenylsulfonyl)amino]-3-pyridinyl}-2-quinoxalinyl)-1-piperazinecarboxylate;
N-{5-[3-(1-piperazinyl)-6-quinoxalinyl]-3-pyridinyl}benzenesulfonamide;
N-[5-(3-{3-[3-(methyloxy)phenyl]-1-pyrrolidinyl}-6-quinoxalinyl)-3-pyridinyl]benzenesulfonamide;
N-[5-(3-{3-[3-(methyloxy)phenyl]-1-pyrrolidinyl}-6-quinoxalinyl)-3-pyridinyl]benzenesulfonamide;
N-[5-(3-{3-[4-(methyloxy)phenyl]-1-pyrrolidinyl}-6-quinoxalinyl)-3-pyridinyl]benzenesulfonamide;
N-[5-(3-{3-[4-(methyloxy)phenyl]-1-pyrrolidinyl}-6-quinoxalinyl)-3-pyridinyl]benzenesulfonamide;
N-[5-(3-{4-[(2-methylpropyl)sulfonyl]-1-piperazinyl}-6-quinoxalinyl)-3-pyridinyl]benzenesulfonamide;
N-{5-[3-(2-furanyl)-6-quinoxalinyl]-3-pyridinyl}benzenesulfonamide;
N-{5-[3-(2-thienyl)-6-quinoxalinyl]-3-pyridinyl}benzenesulfonamide;
N-{5-[3-(1-methyl-1H-imidazol-5-yl)-6-quinoxalinyl]-3-pyridinyl}benzenesulfonamide;
N-{5-[3-(1,3-oxazol-2-yl)-6-quinoxalinyl]-3-pyridinyl}benzenesulfonamide;
N-{2-chloro-5-[3-(4-{[4-(methyloxy)phenyl]sulfonyl}-1-piperazinyl)-6-quinoxalinyl]-3-pyridinyl}benzenesulfonamide;
N-{5-[3-(4-{[4-(methylsulfonyl)phenyl]sulfonyl}-1-piperazinyl)-6-quinoxalinyl]-3-pyridinyl}benzenesulfonamide;
4-{[4-(7-{5-[(phenylsulfonyl)amino]-3-pyridinyl}-2-quinoxalinyl)-1-piperazinyl]sulfonyl}benzenesulfonamide;
N,N-dimethyl-4-{[4-(7-{5-[(phenylsulfonyl)amino]-3-pyridinyl}-2-quinoxalinyl)-1-piperazinyl]sulfonyl}benzenesulfonamide;
N-[5-(3-{4-[(4-hydroxyphenyl)sulfonyl]-1-piperazinyl}-6-quinoxalinyl)-3-pyridinyl]benzenesulfonamide;
N-(5-{3-[4-(4-morpholinylsulfonyl)-1-piperazinyl]-6-quinoxalinyl}-3-pyridinyl)benzenesulfonamide;

N-[5-(3-{4-[(4-acetylphenyl)sulfonyl]-1-piperazinyl}-6-quinoxalinyl)-3-pyridinyl]benzenesulfonamide;
N-[5-(3-{4-[(4-aminophenyl)sulfonyl]-1-piperazinyl}-6-quinoxalinyl)-3-pyridinyl]benzenesulfonamide;
N-[5-(3-{4-[(4-{[(dimethylamino)carbonyl]amino}phenyl)sulfonyl]-1-piperazinyl}-6-quinoxalinyl)-3-pyridinyl]benzenesulfonamide;
4-{[4-(7-{5-[(phenylsulfonyl)amino]-3-pyridinyl}-2-quinoxalinyl)-1-piperazinyl]sulfonyl}benzoic acid;
3-[(7-{5-[(phenylsulfonyl)amino]-3-pyridinyl}-2-quinoxalinyl)amino]benzoic acid;
N-[5-(3-{[3-(methyloxy)phenyl]amino}-6-quinoxalinyl)-3-pyridinyl]benzenesulfonamide;
N-[5-(3-phenyl-6-quinoxalinyl)-3-pyridinyl]benzenesulfonamide;
N-{5-[3-(1,3-thiazol-5-yl)-6-quinoxalinyl]-3-pyridinyl}benzenesulfonamide;
N-(5-{3-[1-(phenylmethyl)-1H-pyrazol-4-yl]-6-quinoxalinyl}-3-pyridinyl)benzenesulfonamide;
N-[5-(3-{4-[(1-methyl-1H-pyrazol-4-yl)sulfonyl]-1-piperazinyl}-6-quinoxalinyl)-3-pyridinyl]benzenesulfonamide;
N-(5-{3-[4-(cyclohexylsulfonyl)-1-piperazinyl]-6-quinoxalinyl}-3-pyridinyl)benzenesulfonamide;
N,N-dimethyl-4-{7-[5-({methylidene[(2Z)-1-methylidene-2,4-pentadien-1-yl]oxido-$\lambda^4$-sulfanyl}amino)-3-pyridinyl]-2-quinoxalinyl}-1-piperazinesulfonamide;
(2E,4Z)-N-(5-{3-[4-(4-morpholinyl)-1-piperidinyl]-6-quinoxalinyl}-3-pyridinyl)-2,4-hexadiene-3-sulfonamide;
(3Z)-N-[5-(3-{4-[[2-(dimethylamino)ethyl](methyl)amino]-1-piperidinyl}-6-quinoxalinyl)-3-pyridinyl]-1,3-pentadiene-2-sulfonamide;
N-(5-{3-[4-(cyclopropylsulfonyl)-1-piperazinyl]-6-quinoxalinyl}-3-pyridinyl)benzenesulfonamide;
N-{5-[3-(4-{[4-(methyloxy)phenyl]sulfonyl}-1-piperazinyl)-6-quinoxalinyl]-3-pyridinyl}cyclopropanesulfonamide;
N-{5-[3-(4-{[4-(methyloxy)phenyl]sulfonyl}-1-piperazinyl)-6-quinoxalinyl]-2-oxo-1,2-dihydro-3-pyridinyl}benzenesulfonamide;
3-(methyloxy)-5-[(7-{5-[(phenylsulfonyl)amino]-3-pyridinyl}-2-quinoxalinyl)amino]benzoic acid;
N-{5-[3-(4-{[3-(methyloxy)phenyl]sulfonyl}-1-piperazinyl)-6-quinoxalinyl]-3-pyridinyl}benzenesulfonamide;
N-{5-[3-(4-{[4-(1H-tetrazol-5-yl)phenyl]sulfonyl}-1-piperazinyl)-6-quinoxalinyl]-3-pyridinyl}benzenesulfonamide;
N-{5-[3-(4-{[2-(methyloxy)phenyl]sulfonyl}-1-piperazinyl)-6-quinoxalinyl]-3-pyridinyl}benzenesulfonamide;
phenylmethyl 4-[(4-{7-[(1E,2E)-1-ethylidene-3-({[(2Z)-1-methylidene-2,4-pentadien-1-yl]thio}amino)-2-buten-1-yl]-2-quinoxalinyl}-1-piperazinyl)sulfonyl]-1-piperidinecarboxylate;
1,1-dimethylethyl 4-[7-(5-{[methylidene(oxido)phenyl-$\lambda^4$-sulfanyl]amino}-3-pyridinyl)-2-quinoxalinyl]-3-oxo-1-piperazinecarboxylate;
N-{5-[3-(2-oxo-1-piperazinyl)-6-quinoxalinyl]-3-pyridinyl}benzenesulfonamide;
N-methyl-1-(7-{5-[(phenylsulfonyl)amino]-3-pyridinyl}-2-quinoxalinyl)-4-piperidinesulfonamide;
1-{7-[5-({[(1E,3Z)-1-ethenyl-1,3-pentadien-1-yl]sulfonyl}amino)-3-pyridinyl]-2-quinoxalinyl}-4-piperidinesulfonamide;
1-[7-(5-{[(2Z)-2-buten-1-yl(methylidene)oxido-$\lambda^4$-sulfanyl]amino}-3-pyridinyl)-2-quinoxalinyl]-N,N-dimethyl-4-piperidinesulfonamide;
(2E,4Z)-N-(5-{3-[4-(methylsulfonyl)-2-oxo-1-piperazinyl]-6-quinoxalinyl}-3-pyridinyl)-2,4,6-heptatriene-3-sulfonamide;
N-{5-[3-(4-{[4-(methyloxy)phenyl]sulfonyl}-2-oxo-1-piperazinyl)-6-quinoxalinyl]-3-pyridinyl}benzenesulfonamide;
N,N'-(2,7-quinoxalinediyldi-5,3-pyridinediyl)dibenzenesulfonamide;
7-(5-{[(2Z)-2-buten-1-yl(methylidene)-$\lambda^4$-sulfanyl]amino}-3-pyridinyl)-N-phenyl-2-quinoxalinamine;
N-{5-[3-(4-{[5-{[(dimethylamino)carbonyl]amino}-2-(ethyloxy)phenyl]sulfonyl}-1-piperazinyl)-6-quinoxalinyl]-3-pyridinyl}benzenesulfonamide;
1-(7-{5-[(phenylsulfonyl)amino]-3-pyridinyl}-2-quinoxalinyl)-4-piperidinecarboxamide;
N-(2-hydroxyethyl)-1-(7-{5-[(phenylsulfonyl)amino]-3-pyridinyl}-2-quinoxalinyl)-4-piperidinecarboxamide;
N-(2-hydroxyethyl)-1-{7-[5-(methylamino)-3-pyridinyl]-2-quinoxalinyl}-4-piperidinesulfonamide-1-propene (1:1);
N-{5-[3-(4-{[2-(methyloxy)phenyl]sulfonyl}-1-piperazinyl)-6-quinoxalinyl]-3-pyridinyl}cyclopropanesulfonamide;
7-(5-{[cyclopropyl(methylidene)oxido-$\lambda^4$-sulfanyl]amino}-6-methyl-3-pyridinyl)-2-(4-{[2-(methyloxy)phenyl]sulfonyl}-1-piperazinyl)quinoxaline;
N-{2-(methyloxy)-5-[3-(4-{[2-(methyloxy)phenyl]sulfonyl}-1-piperazinyl)-6-quinoxalinyl]-3-pyridinyl}methanesulfonamide;
N,N-dimethyl-N'-{5-[3-(4-{[2-(methyloxy)phenyl]sulfonyl}-1-piperazinyl)-6-quinoxalinyl]-3-pyridinyl}sulfamide;
N-[2-(methyloxy)ethyl]-1-(7-{5-[(phenylsulfonyl)amino]-3-pyridinyl}-2-quinoxalinyl)-4-piperidinecarboxamide;
N-[4-(aminosulfonyl)phenyl]-1-(7-{5-[(phenylsulfonyl)amino]-3-pyridinyl}-2-quinoxalinyl)-4-piperidinecarboxamide;
N-[2-(dimethylamino)ethyl]-1-(7-{5-[(phenylsulfonyl)amino]-3-pyridinyl}-2-quinoxalinyl)-4-piperidinecarboxamide;
N-{5-[3-(4-{[4-(methyloxy)phenyl]oxy}-1-piperidinyl)-6-quinoxalinyl]-3-pyridinyl}benzenesulfonamide;
methyl 2-(methyloxy)-4-[(7-{5-[(phenylsulfonyl)amino]-3-pyridinyl}-2-quinoxalinyl)amino]benzoate;
1,1-dimethylethyl 4-{[1-(7-{5-[(phenylsulfonyl)amino]-3-pyridinyl}-2-quinoxalinyl)-4-piperidinyl]carbonyl}-1-piperazinecarboxylate;
2-amino-N,N-dimethyl-5-{3-[(phenylmethyl)oxy]-6-quinoxalinyl}-3-pyridinesulfonamide;
5-[3-(4-methyl-1-piperazinyl)-6-quinoxalinyl]-2-pyridinamine;
N-{5-[3-(4-methyl-1-piperazinyl)-6-quinoxalinyl]-2-pyridinyl}acetamide;
5-[3-(4-methyl-1-piperazinyl)-6-quinoxalinyl]-2-pyridinecarbonitrile;
N-{5-[3-(4-methyl-1-piperazinyl)-6-quinoxalinyl]-2-pyridinyl}benzenesulfonamide;
N-{5-[3-(4-methyl-1-piperazinyl)-6-quinoxalinyl]-2-pyridinyl}methanesulfonamide;
N-{5-[3-(4-methyl-1-piperazinyl)-6-quinoxalinyl]-2-pyridinyl}-N-(methylsulfonyl)methanesulfonamide;
2-(4-methyl-1-piperazinyl)-7-[6-(4-morpholinyl)-3-pyridinyl]quinoxaline;
2-(4-methyl-1-piperazinyl)-7-[6-(1-piperazinyl)-3-pyridinyl]quinoxaline;
N-{5-[3-(1,1-dioxido-4-thiomorpholinyl)-6-quinoxalinyl]-3-pyridinyl}benzenesulfonamide;

N-{5-[3-(4-thiomorpholinyl)-6-quinoxalinyl]-3-pyridinyl}benzenesulfonamide;
N-{5-[3-(4-pyridinyl)-6-quinoxalinyl]-3-pyridinyl}benzenesulfonamide;
N-{5-[3-(3-pyridinyl)-6-quinoxalinyl]-3-pyridinyl}benzenesulfonamide;
N-(5-{3-[methyl(1-methyl-4-piperidinyl)amino]-6-quinoxalinyl}-3-pyridinyl)benzenesulfonamide;
N-{5-[3-(4-piperidinylamino)-6-quinoxalinyl]-3-pyridinyl}benzenesulfonamide;
N-[5-(3-{[(1-methyl-4-piperidinyl)methyl]amino}-6-quinoxalinyl)-3-pyridinyl]benzenesulfonamide;
N-{5-[3-(methyl{2-[methyl(methylsulfonyl)amino]ethyl}amino)-6-quinoxalinyl]-3-pyridinyl}benzenesulfonamide;
N-[5-(3-{methyl[2-(methylamino)ethyl]amino}-6-quinoxalinyl)-3-pyridinyl]benzenesulfonamide;
N-{5-[3-(methyl{2-[(methylsulfonyl)amino]ethyl}amino)-6-quinoxalinyl]-3-pyridinyl}benzenesulfonamide;
N-(5-{3-[(2-aminoethyl)(methyl)amino]-6-quinoxalinyl}-3-pyridinyl)benzenesulfonamide;
N-{5-[3-({2-[(methylsulfonyl)amino]ethyl}amino)-6-quinoxalinyl]-3-pyridinyl}benzenesulfonamide;
N-[5-(3-{[1-(methylsulfonyl)-4-piperidinyl]amino}-6-quinoxalinyl)-3-pyridinyl]benzenesulfonamide;
N-{5-[3-(4-pyridazinyl)-6-quinoxalinyl]-3-pyridinyl}benzenesulfonamide;
N-(5-{3-[(1-methyl-4-piperidinyl)amino]-6-quinoxalinyl}-3-pyridinyl)benzenesulfonamide;
N,N-dimethyl-4-[(7-{5-[(phenylsulfonyl)amino]-3-pyridinyl}-2-quinoxalinyl)amino]-1-piperidinesulfonamide;
N-(5-{3-[(1-{[4-(methyloxy)phenyl]sulfonyl}-4-piperidinyl)amino]-6-quinoxalinyl}-3-pyridinyl)benzenesulfonamide;
N-[3-(methyloxy)phenyl]-7-(3-pyridinyl)-2-quinoxalinamine;
N-[2-(methyloxy)-5-(3-{[3-(methyloxy)phenyl]amino}-6-quinoxalinyl)-3-pyridinyl]benzenesulfonamide and
N-[2-chloro-5-(3-{[3-(methyloxy)phenyl]amino}-6-quinoxalinyl)-3-pyridinyl]benzenesulfonamide.

This invention also relates to a method of treating cancer, which comprises co-administering to a subject in need thereof an effective amount of a compound of Formula (I), and/or a pharmaceutically acceptable salt thereof; and at least one anti-neoplastic agent such as one selected from the group consisting of: anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

This invention also relates to a method of treating cancer, which comprises co-administering to a subject in need thereof an effective amount of a compound of Formula (I), and/or a pharmaceutically acceptable salt thereof; and at least one signal transduction pathway inhibitor such as one selected from the group consisting of: receptor tyrosine kinase inhibitor, non-receptor tyrosine kinase inhibitor, SH2/SH3 domain blocker, serine/threonine kinase inhibitor, phosphotidyl inositol-3 kinase inhibitor, myo-inositol signaling inhibitor, and Ras oncogene inhibitor.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Compounds of Formula (I) are included in the pharmaceutical compositions of the invention.

DEFINITIONS

By the term "substituted amino" as used herein, is meant —NR30R40 wherein each R30 and R40 is independently selected from a group including hydrogen, C1-6alkyl, acyl, C3-C7cycloalkyl, wherein at least one of R30 and R40 is not hydrogen.

By the term "acyl" as used herein, unless otherwise defined, is meant —C(O)(alkyl), —C(O)(cycloalkyl), —C(O)(aryl) or —C(O)(heteroaryl), wherein heteroaryl and aryl are optionally substituted.

By the term "aryl" as used herein, unless otherwise defined, is meant aromatic, hydrocarbon, ring system. The ring system may be monocyclic or fused polycyclic (e.g. bicyclic, tricyclic, etc.). In various embodiments, the monocyclic aryl ring is C5-C10, or C5-C7, or C5-C6, where these carbon numbers refer to the number of carbon atoms that form the ring system. A C6 ring system, i.e. a phenyl ring is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group.

By the term "heteroaryl" as used herein, unless otherwise defined, is meant an aromatic ring system containing carbon(s) and at least one heteroatom. Heteroaryl may be monocyclic or polycyclic. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include but are not limited to: benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, and thiophene.

By the term "monocyclic heteroaryl" as used herein, unless otherwise defined, is meant a monocyclic heteroaryl ring containing 1-5 carbon atoms and 1-4 hetero atoms.

By the term "alkylcarboxy" as used herein, unless otherwise defined, is meant —(CH$_2$)$_n$COOR$_{80}$, wherein R80 is hydrogen or C1-C6alkyl, n is 0-6.

By the term "alkoxy" as used herein is meant —O(alkyl) including —OCH$_3$, —OCH$_2$CH$_3$ and —OC(CH$_3$)$_3$ where alkyl is as described herein.

By the term "alkylthio" as used herein is meant —S(alkyl) including —SCH$_3$, —SCH$_2$CH$_3$ where alkyl is as described herein.

The term "cycloalkyl" as used herein unless otherwise defined, is meant a nonaromatic, unsaturated or saturated, cyclic or polycyclic C$_3$-C$_{12}$.

Examples of cycloalkyl and substituted cycloalkyl substituents as used herein include: cyclohexyl, aminocyclohexyl, cyclobutyl, aminocyclobutyl, 4-hydroxy-cyclohexyl, 2-ethylcyclohexyl, propyl-4-methoxycyclohexyl, 4-methoxycyclohexyl, 4-carboxycyclohexyl, cyclopropyl, aminocyclopentyl, and cyclopentyl.

By the term "heterocycloalkyl" as used herein is meant a non-aromatic, unsaturated or saturated, monocyclic or polycyclic, heterocyclic ring containing at least one carbon and at least one heteroatom. Exemplary monocyclic heterocyclic rings include: piperidine, piperazine, pyrrolidine, and morpholine. Exemplary polycyclic heterocyclic rings include quinuclidine.

By the term "substituted" as used herein, unless otherwise defined, is meant that the subject chemical moiety has one to five substituents, suitably from one to three, selected from the group consisting of: hydrogen, halogen, C1-C6alkyl, amino, urea, trifluoromethyl, —$(CH_2)_n$COOH, C3-C7cycloalkyl, substituted amino, aryl, heteroaryl, arylalkyl, arylcycloalkyl, heteroarylalkyl, heterocycloalkyl, cyano, hydroxyl, alkoxy, alkylthio, aryloxy, acyloxy, acyl, acylamino, aminoacyl, arylamino, nitro, oxo, —$CO_2R_{50}$, —$SO_2R_{70}$, —$NR_{50}SO_2R_{70}$, $NR_{50}C(O)R_{75}$ and —$CONR_{55}R_{60}$, wherein R50 and R55 are each independently selected from: hydrogen, alkyl, and C3-C7cycloalkyl; R55 and R60 can optionally form a heterocycloalkyl ring; n is 0 to 6; R75 is selected from the group consisting of: C1-C6alkyl, C3-7cycloalkyl, substituted C3-7cycloalkyl, aryl, substituted aryl, heteroaryl, substituted heteroaryl, amino, substituted amino, arylamino, C1-C6heterocycloalkyl, alkoxy, aryloxy and substituted C1-C6heterocycloalkyl; each R60 and R70 is independently selected from the group consisting of: C1-C6alkyl, C3-C7cycloalkyl, substituted C1-C6heterocycloalkyl, C1-C6heterocycloalkyl, halogen, amino, substituted amino, arylamino, trifluoromethyl, cyano, hydroxyl, alkoxy, oxo, —$(CH_2)_n$COOH, aryl optionally fused with a five-membered ring or substituted with one to five groups selected from the group consisting of: C1-C6alkyl, C3-C7cycloalkyl, halogen, amino, substituted amino, trifluoromethyl, cyano, hydroxyl, alkoxy, oxo, or —$(CH_2)_n$COOH, or heteroaryl optionally fused with a five-membered ring or substituted with one to five groups selected from the group consisting of: C1-C6alkyl, C3-C7cycloalkyl, halogen, amino, trifluoromethyl, cyano, hydroxyl, alkoxy, oxo, or —$(CH_2)_n$COOH.

By the term "substituted", when referred in the definition of R60, R70, R75, "arylamino", and "aryloxy", is meant that the subject chemical moiety has one to five substituents, suitably from one to three substituents selected from the group consisting of: hydrogen, C1-C6alkyl, halogen, trifluoromethyl, —$(CH_2)_n$COOH, amino, substituted amino, cyano, hydroxyl, alkoxy, alkylthio, aryloxy, acyloxy, acyl, acylamino, and nitro, n is 0-6.

By the term "acyloxy" as used herein is meant —OC(O) alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "acylamino" as used herein is meant —N(H)C(O)alkyl, —N(H)C(O)(cycloalkyl) where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aminoacyl" as used herein is meant —C(O)N(alkyl)$_n$, —C(O)N(cycloalkyl)$_n$ where alkyl is as described herein, n is 1-2.

By the term "aryloxy" as used herein is meant —O(aryl), —O(substituted aryl), —O(heteroaryl) or —O(substituted heteroaryl).

By the term "arylamino" as used herein is meant —$NR_{80}$(aryl), —$NR_{80}$(substituted aryl), —$NR_{80}$(heteroaryl) or —$NR_{80}$(substituted heteroaryl), wherein R80 is H, C1-6alkyl or C3-C7cycloalkyl.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein, including alkyl chains defined by the term "—$(CH_2)_n$", "—$(CH_2)_m$" and the like, is meant a linear or branched, saturated or unsaturated hydrocarbon chain, and unless otherwise defined, the carbon chain will contain from 1 to 12 carbon atoms.

By the term "substituted alkyl" as used herein is meant an alkyl group substituted with one to six substituents selected from the group consisting of: halogen, trifluoromethyl, alkylcarboxy, amino, substituted amino, cyano, hydroxyl, alkoxy, alkylthio, aryloxy, acyloxy, acyl, acylamino, carbamate, urea, sulfonamate, C3-7cycloheteralkyl, C3-7cycloalkyl and nitro.

Examples of alkyl and substituted alkyl substituents as used herein include: —$CH_3$, —$CH_2$—$CH_3$, —$CH_2$—$CH_2$—$CH_3$, —$CH(CH_3)_2$, —$CH_2$—$CH_2$—$C(CH_3)_3$, —$CH_2$—$CF_3$, —$C\equiv C$—$C(CH_3)_3$, —$C\equiv C$—$CH_2$—OH, cyclopropylmethyl, —$CH_2$—$C(CH_3)_2$—$CH_2$—$NH_2$, —$C\equiv C$—$C_6H_5$, —$C\equiv C$—$C(CH_3)_2$—OH, —$CH_2$—$CH(OH)$—$CH(OH)$—$CH(OH)$—$CH(OH)$—$CH_2$—OH, piperidinylmethyl, methoxyphenylethyl, —$C(CH_3)_3$, —$(CH_2)_3$—$CH_3$, —$CH_2$—$CH(CH_3)_2$, —$CH(CH_3)$—$CH_2$—$CH_3$, —$CH=CH_2$, and —$C\equiv C$—$CH_3$.

By the term "treating" and derivatives thereof as used herein, is meant prophylatic and therapeutic therapy.

By the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Suitably, if the administration is not simultaneous, the compounds are administered in a close time proximity to each other. Furthermore, it does not matter if the compounds are administered in the same dosage form, e.g. one compound may be administered topically and another compound may be administered orally.

The term "compound" as used herein includes all isomers of the compound. Examples of such isomers include: enantiomers, tautomers, rotamers.

In formula (II) to (VIII), when a "dot" bond is drawn between two atoms, it is meant that such bond can be either single or double bond. A ring system containing such bonds can be aromatic or non-aromatic.

Certain compounds described herein may contain one or more chiral atoms, or may otherwise be capable of existing as two enantiomers, or two or more diastereoisomers. Accordingly, the compounds of this invention include mixtures of enantiomers/diastereoisomers as well as purified enantiomers/diastereoisomers or enantiomerically/diastereoisomerically enriched mixtures. Also included within the scope of the invention are the individual isomers of the compounds represented by formula I or II above as well as any wholly or partially equilibrated mixtures thereof. The present invention also covers the individual isomers of the compounds represented by the formulas above as mixtures with isomers thereof in which one or more chiral centers are inverted. Further, an example of a possible tautomer is an oxo substituent in place of a hydroxy substituent. Also, as stated above, it is understood that all tautomers and mixtures of tautomers are included within the scope of the compounds of Formula I or II.

Compounds of Formula (I) are included in the pharmaceutical compositions of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

It has now been found that compounds of the present invention are inhibitors of the Phosphatoinositides 3-kinases (PI3Ks). When the phosphatoinositides 3-kinase (PI3K) enzyme is inhibited by a compound of the present invention, PI3K is unable to exert its enzymatic, biological and/or pharmacological effects. The compounds of the present invention are therefore useful in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

The compounds of Formula (I) are useful as medicaments in particular for the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries. According to one embodiment of the present invention, the compounds of Formula (I) are inhibitors of one or more phosphatoinositides 3-kinases (PI3Ks), suitably, Phosphatoinositides 3-kinase γ (PI3Kγ), Phosphatoinositides 3-kinase γ (PI3Kα), Phosphatoinositides 3-kinase γ (PI3Kβ), and/or Phosphatoinositides 3-kinase γ (PI3Kδ).

Compounds according to Formula (I) are suitable for the modulation, notably the inhibition of the activity of phosphatoinositides 3-kinases (PI3K), suitably phosphatoinositides 3-kinase (PI3Kα). Therefore the compounds of the present invention are also useful for the treatment of disorders which are mediated by PI3Ks. Said treatment involves the modulation—notably the inhibition or the down regulation—of the phosphatoinositides 3-kinases.

Suitably, the compounds of the present invention are used for the preparation of a medicament for the treatment of a disorder selected from multiple sclerosis, psoriasis, rheumatoid arthritis, systemic lupus erythematosis, inflammatory bowel disease, lung inflammation, thrombosis or brain infection/inflammation, such as meningitis or encephalitis, Alzheimer's disease, Huntington's disease, CNS trauma, stroke or ischemic conditions, cardiovascular diseases such as atherosclerosis, heart hypertrophy, cardiac myocyte dysfunction, elevated blood pressure or vasoconstriction.

Suitably, the compounds of Formula (I) are useful for the treatment of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

Suitably, the compounds of Formula (I) are useful for the treatment of neurodegenerative diseases including multiple sclerosis, Alzheimer's disease, Huntington's disease, CNS trauma, stroke or ischemic conditions.

Suitably, the compounds of Formula (I) are useful for the treatment of cardiovascular diseases such as atherosclerosis, heart hypertrophy, cardiac myocyte dysfunction, elevated blood pressure or vasoconstriction.

Suitably, the compounds of Formula (I) are useful for the treatment of chronic obstructive pulmonary disease, anaphylactic shock fibrosis, psoriasis, allergic diseases, asthma, stroke, ischemic conditions, ischemia-reperfusion, platelets aggregation/activation, skeletal muscle atrophy/hypertrophy, leukocyte recruitment in cancer tissue, angiogenesis, invasion metastasis, in particular melanoma, Karposi's sarcoma, acute and chronic bacterial and viral infections, sepsis, transplantation rejection, graft rejection, glomerulo sclerosis, glomerulo nephritis, progressive renal fibrosis, endothelial and epithelial injuries in the lung, and lung airway inflammation.

Because the pharmaceutically active compounds of the present invention are active as PI3 kinase inhibitors, particularly the compounds that inhibit PI3Kα, either selectively or in conjunction with one or more of PI3Kδ, PI3Kβ, and/or PI3Kγ, they exhibit therapeutic utility in treating cancer.

Suitably, the invention relates to a method of treating cancer in a mammal, including a human, wherein the cancer is selected from: brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone and thyroid.

Suitably, the invention relates to a method of treating cancer in a mammal, including a human, wherein the cancer is selected from: Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, Acute megakaryocytic leukemia, promyelocytic leukemia and Erythroleukemia.

Suitably, the invention relates to a method of treating cancer in a mammal, including a human, wherein the cancer is selected from: malignant lymphoma, hodgkins lymphoma, non-hodgkins lymphoma, lymphoblastic T cell lymphoma, Burkitt's lymphoma and follicular lymphoma.

Suitably, the invention relates to a method of treating cancer in a mammal, including a human, wherein the cancer is selected from: neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

When a compound of Formula (I) is administered for the treatment of cancer, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present PI3 kinase inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4-[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H, 12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

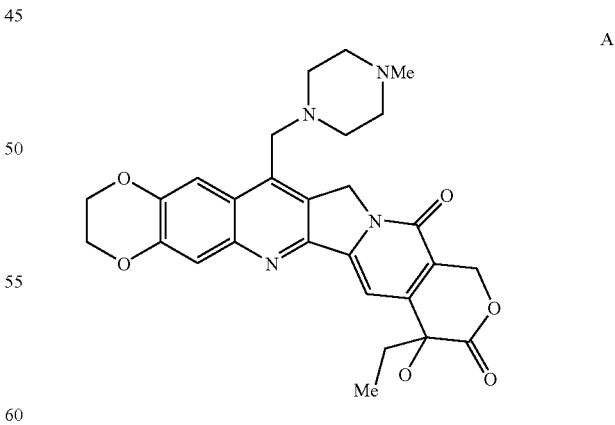

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of formula I and/or a pharmaceutically acceptable salt, hydrate, solvate or pro-drug thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Because the pharmaceutically active compounds of the present invention are active as PI3 kinase inhibitors, particularly the compounds that modulate/inhibit PI3Kα, either selectively or in conjunction with one or more of PI3Kγ, PI3Kβ, and/or PI3Kδ, they exhibit therapeutic utility in treating a disease state selected from: autoimmune disorders, inflammatory diseases, cardiovascular diseases, neurodegenerative diseases, allergy, cancer, asthma, pancreatitis, multiorgan failure, kidney diseases, platelet aggregation, sperm motility, transplantation rejection, graft rejection and lung injuries.

When a compound of Formula (I) is administered for the treatment of a disease state selected from: autoimmune disorders, inflammatory diseases, cardiovascular diseases, neurodegenerative diseases, cancer, allergy, asthma, pancreatitis, multiorgan failure, kidney diseases, platelet aggregation, sperm motility, transplantation rejection, graft rejection or lung injuries, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of autoimmune disorders, inflammatory diseases, cardiovascular diseases, cancer, neurodegenerative diseases, allergy, asthma, pancreatitis, multiorgan failure, kidney diseases, platelet aggregation, sperm motility, transplantation rejection, graft rejection and/or lung injuries.

Biological Assays

PI3K Alpha Leadseeker SPA Assay

Compounds of the present invention were tested according to the following assays and found as inhibitors of PI3 kinases, particularly PI3Kα. The exemplified compounds were tested and found active against PI3Kα. The $IC_{50}$'s ranged from about 1 nM to 10 μM. The majority of the compounds were under 500 nM; the most active compounds were under 10 nM.

The compound of Example 1 was tested generally according to the assays described herein and in at least one experimental run exhibited a IC50 value: equal to 5 nM against PI3Kα.

The compound of Example 2 was tested generally according to the assays described herein and in at least one experimental run exhibited a IC50 value: equal to 100 nM against PI3Kα.

The compound of Example 4 was tested generally according to the assays described herein and in at least one experimental run exhibited a IC50 value: equal to 50 nM against PI3Kα.

The compound of Example 19 was tested generally according to the assays described herein and in at least one experimental run exhibited a IC50 value: equal to 8 nM against PI3Kα.

The compound of Example 20 was tested generally according to the assays described herein and in at least one experimental run exhibited a IC50 value: equal to 16 nM against PI3Kα.

The compound of Example 69 was tested generally according to the assays described herein and in at least one experimental run exhibited a IC50 value: equal to 13 nM against PI3Kα.

The compound of Example 70 was tested generally according to the assays described herein and in at least one experimental run exhibited a IC50 value: equal to 200 nM against PI3Kα.

Assay Principle

SPA imaging beads are microspheres containing scintillant which emit light in the red region of the visible spectrum. As a result, these beads are ideally suited to use with a CCD imager such as the Viewlux. The Leadseeker beads used in this system are polystyrene beads that have been coupled with polyethyleneimine. When added to the assay mixture, the beads absorb both the substrate (PIP2) and product (PIP3). Adsorbed $P^{33}$-PIP3 will cause an increase in signal, measured as ADUs (analog to digital units). This protocol details the use of the PEI-PS Leadseeker beads for assays using His-p110/p85 PI3K alpha.

Assay Protocol

Solid compounds are typically plated with 0.1 μl of 100% DMSO in all wells (except column 6 and 18) of a 384-well, flat bottom, low volume plate (Greiner 784075). The compounds are serially diluted (3-fold in 100% DMSO) across the plate from column 1 to column 12 and column 13 to column 24 and leave column 6 and 18 containing only DMSO to yield 11 concentrations for each test compound.

The assay buffer contains MOPS (pH 6.5), CHAPS, and DTT. PI3K alpha and PIP2 (L-alpha-D-myo-Phosphatidylinositol 4,5-bisphosphate [PI(4,5)P2]3-O-phospho linked, D(+)-sn-1,2-di-O-octanoylglyceryl, CellSignals # 901) are mixed and incubated in the plate with compound for 30 min prior to starting the reaction with the addition of $P^{33}$-ATP and $MgCl_2$ (reagents added using Zoom). Enzyme-free wells (column 18) are typically done to determine the low control. PEI-PS Leadseeker beads in PBS/EDTA/CHAPS are added (by Multidrop) to quench the reaction, and the plates are allowed to incubate for at least one hour (typically overnight) before centrifugation. The signal is determined using a Viewlux detector and is then imported into curve fitting software (Activity Base) for construction of concentration response curves. The percent inhibition of activity is calculated relative to high controls (C1, 0.1 μl DMSO in column 6, rows A-P)) and low controls (C2, 5 μl of 40 uM PIP2 in buffer in column 18, rows A-P) using, $100*(1-(U1-C2)/(C1-C2))$. The concentration of test compound yielding 50% inhibition is determined using the equation, $y=((Vmax*x)/(K+x))+Y2$, where "K" was equal to the IC50. The IC50 values are converted to pIC50 values, i.e., -log IC50 in Molar concentration.

Cellular Assays:
Day 1
Plate cells before noon
10K cells/well in clear flat-bottomed 96-well plates (f.v. 105 ul)
Last four wells in last column receive media only
Place in 37 degC incubator overnight
Compound plate
Prepare in polypropylene round-bottomed 96-well plates; 8 compounds per
plate, 11-pt titrations of each (3× serial dilution), DMSO in last column (0.15% f.c. on cells)
15 ul in first well, 10 ul DMSO in the rest; take 5 ul from first well and mix in next, continue across plate (excluding last column); seal with foil lid and place at 4 degC
Day 2
Take out Lysis buffer inhibitors (4 degC/−20 degC) and compound plates (4 degC), thaw on bench top; make 1× Tris wash buffer (WB) to fill reservoir on plate washer and top off bench supply (use MiliQ), turn on centrifuge to allow it to cool
Block MSD plates
Make 20 ml 3% blocking solution/plate (600 mg blocker A in 20 ml WB), add 150 ul/well and incubate at RT for at least 1 hr
Add compound (while blocking)
Add 300 ul growth media (RPMI w/Q, 10% FBS) per well (682× dil of compound) to each compound plate
Add 5 ul compound dilution into each well (f.v. 110 ul) on duplicate plates
Place in 37 degC incubator for 30 min
Make lysates
Prepare MSD Lysis buffer; for 10 ml add 200 ul protease inhibitor solution, and 100 ul each of Phosphatase inhibitors I & II (Keep on ice until ready for use)
Remove plates post-incubation, aspirate media with plate washer, wash 1× with cold PBS, and add 80 ul MSD Lysis buffer per well; incubate on shaker at 4 degC for ≧30 min
Spin cold at 2500 rpm for 10 min; leave plates in 4 degC centrifuge until ready for use
AKT duplex assay
Wash plates (4× with 200 ul/well WB in plate washer); tap plates on paper towel to blot
Add 60 ul of lysates/well, incubate on shaker at RT for 1 hr
During incubation prepare detection Ab (3 ml/plate; 2 ml WB and 1 ml blocking solution w/Ab at 10 nM); repeat wash step as above
Add 25 ul of Ab/well, incubate on shaker at RT for 1 hr; repeat wash step as above
Add 150 ul/well 1× Read Buffer (dilute 4× stock in ddH2O, 20 ml/plate), read immediately
Analysis
Observe all the data points at each compound concentration.
The data point from highest inhibitor concentration must be equal or greater than 70% of DMSO control.
IC50 for duplicate runs must be within 2-fold of each other (not flagged in summary template).
Y min must be greater than zero; if both mins are red flagged (>35) then compound is listed as inactive (IC50=>highest dose). If only one min is red flagged, but still ≦50 then call IC50 as listed.
Any data points equal or greater than 30% off the curve will not be considered.

Cell Growth/Death Assay:

BT474, HCC1954 and T-47D (human breast) were cultured in RPMI-1640 containing 10% fetal bovine serum at 37° C. in 5% $CO_2$ incubator. Cells were split into T75 flask (Falcon #353136) two to three days prior to assay set up at density which yields approximately 70-80% confluence at time of harvest for assay. Cells were harvested using 0.25% trypsin-EDTA (Sigma #4049). Cell counts were performed on cell suspension using Trypan Blue exclusion staining. Cells were then plated in 384 well black flat bottom polystyrene (Greiner #781086) in 48 μl of culture media per well at 1,000 cells/well. All plates were placed at 5% $CO_2$, 37° C. overnight and test compounds were added the following day. One plate was treated with CellTiter-Glo (Promega #G7573) for a day 0 (t=0) measurement and read as described below. The test compounds were prepared in clear bottom polypropylene 384 well plates (Greiner#781280) with consecutive two fold dilutions. 4 μl of these dilutions were added to 105 μl culture media, after mixing the solution, 2 μl of these dilutions were added into each well of the cell plates. The final concentration of DMSO in all wells was 0.15%. Cells were incubated at 37° C., 5% $CO_2$ for 72 hours. Following 72 hours of incubation with compounds each plate was developed and read. CellTiter-Glo reagent was added to assay plates using a volume equivalent to the cell culture volume in the wells. Plates were shaken for approximately two minutes and incubated at room temperature for approximately 30 minutes and chemiluminescent signal was read on the Analyst GT (Molecular Devices) reader. Results were expressed as a percent of the t=0 and plotted against the compound concentration. Cell growth inhibition was determined for each compound by fitting the dose response with a 4 or 6 parameter curve fit using XLfit software and determining the concentration that inhibited 50% of the cell growth (gIC50) with the Y min as the t=0 and Y max as the DMSO control. Value from wells with no cells was subtracted from all samples for background correction.

Additional References:

The compounds of the present invention can also be tested to determine their inhibitory activity at PI3Kα, PI3Kδ, PI3Kβ and PI3Kγ according to the following references:

For all PI3K isoforms:
1. Cloning, expression, purification, and characterization of the human Class Ia phosphoinositide 3-kinase isoforms: Meier, T. I.; Cook, J. A.; Thomas, J. E.; Radding, J. A.; Horn, C.; Lingaraj, T.; Smith, M. C. Protein Expr. Purif., 2004, 35(2), 218.
2. Competitive fluorescence polarization assays for the detection of phosphoinositide kinase and phosphatase activity: Drees, B. E.; Weipert, A.; Hudson, H.; Ferguson, C. G.; Chakravarty, L.; Prestwich, G. D. Comb. Chem. High Throughput.Screen., 2003, 6(4), 321.

For PI3Kγ: WO 2005/011686 A1

The pharmaceutically active compounds within the scope of this invention are useful as PI3 Kinase inhibitors in mammals, particularly humans, in need thereof.

The present invention therefore provides a method of treating diseases associated with PI3 kinase inhibition, particularly: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries and other conditions requiring PI3 kinase modulation/inhibition, which comprises administering an effective compound of Formula (I) or a pharmaceutically acceptable salt, hydrate, solvate or prodrug thereof. The compounds of Formula (I) also provide for a method of treating the above indicated disease states because of their ability to act as PI3 inhibitors. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a PI3K inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular PI3 kinase inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing PI3 kinase inhibitory activity in mammals, including humans, comprises administering to a subject in need of such activity an effective PI3 kinase modulating/inhibiting amount of a pharmaceutically active compound of the present invention.

The invention also provides for the use of a compound of Formula (I) in the manufacture of a medicament for use as a PI3 kinase inhibitor.

The invention also provides for the use of a compound of Formula (I) in the manufacture of a medicament for use in therapy.

The invention also provides for the use of a compound of Formula (I) in the manufacture of a medicament for use in treating autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

The invention also provides for a pharmaceutical composition for use as a PI3 inhibitor which comprises a compound of Formula (I) and a pharmaceutically acceptable carrier.

The invention also provides for a pharmaceutical composition for use in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries, which comprises a compound of Formula (I) and a pharmaceutically acceptable carrier.

In addition, the pharmaceutically active compounds of the present invention can be co-administered with further active ingredients, including compounds known to have utility when used in combination with a PI3 kinase inhibitor.

Without further elaboration, it is believed that one skilled in the art can, using the preceding description, utilize the present invention to its fullest extent. The following examples are, therefore, to be construed as merely illustrative and not a limitation of the scope of the present invention in any way.

Experimental Details

The compounds of the following examples are readily made according to Schemes 1-5 or by analogous methods.

Schemes:

Quinoxalines such as represented by compounds of Formula I can be prepared from, for example, bromoquinoxalinols (2) which have been prepared in the literature (*Journal of Medicinal Chemistry*, 1981, 24(1), 93-101). As outlined in Scheme 1, bromoquinoxalinols such as compound 2 may be converted to a bromochloroquinoxaline such as compound 3 by for example, treatment with phosphorous oxychloride at elevated temperatures (typically 120° C.). The resulting chlorinated compound (3) may undergo a variety of coupling reactions as delineated by steps C, D or E. When the coupling step is for instance a nucleophilic displacement reaction such as for steps C or D, suitable nucleophiles such as amines, or alkoxides are commercially available or easily prepared by methods known to those skilled in the art. In the instances where the coupling step is an amine or alkoxide displacement of the chloride in compound 3, such a displacement may be carried out at room temperature or further facilitated by heating to temperatures such as 70-100° C. either in neat reagent or in a suitable polar solvent such as N,N'-dimethylformamide. Alternatively, the coupling step to prepare compounds of formula 4 may be a transition metal (such as palladium) catalyzed cross-coupling reaction of an aryl or heteroaryl stannane, boronate ester or boronic acid with compound 3, such as in step E. An examplerary coupling reaction such as a Suzuki cross-coupling depicted in step E can be achieved by treating compound 3 with an appropriate palladium catalyst (typically 1,1'-bis(diphenylphosphino)ferrocene]dichloropalladium(II) dichloromethane complex (1:1)), in the presence of inorganic base (such as potassium carbonate, sodium carbonate or sodium bicabonate) and a suitable solvent (such as 1,4-dioxane or N,N'-dimethylformamide) at elevated temperatures (typically 100° C.). The resulting compounds of formula (4) may undergo another palladium catalyzed coupling reaction as described above with an aryl or heteroaryl boronate ester or boronic acid to furnish compounds of the present invention such as 6. Likewise, in the instances when R2 in compound 4 is N or O, borylation can be achieved with a palladium catalyst (such as 1,1'-bis(diphenylphosphino)ferrocene]dichloropalladium(II) dichloromethane complex (1:1)) in the presence of base (such as potassium acetate) in solvent (such as dioxane) at elevated temperature (typically 100° C.) to provide boronate esters such as compound 5. Such boronate esters can undergo typical Suzuki cross-coupling reactions (as described above) with appropriate aryl or heteroaryl halides to provide compounds of the present invention, such as compound 6.

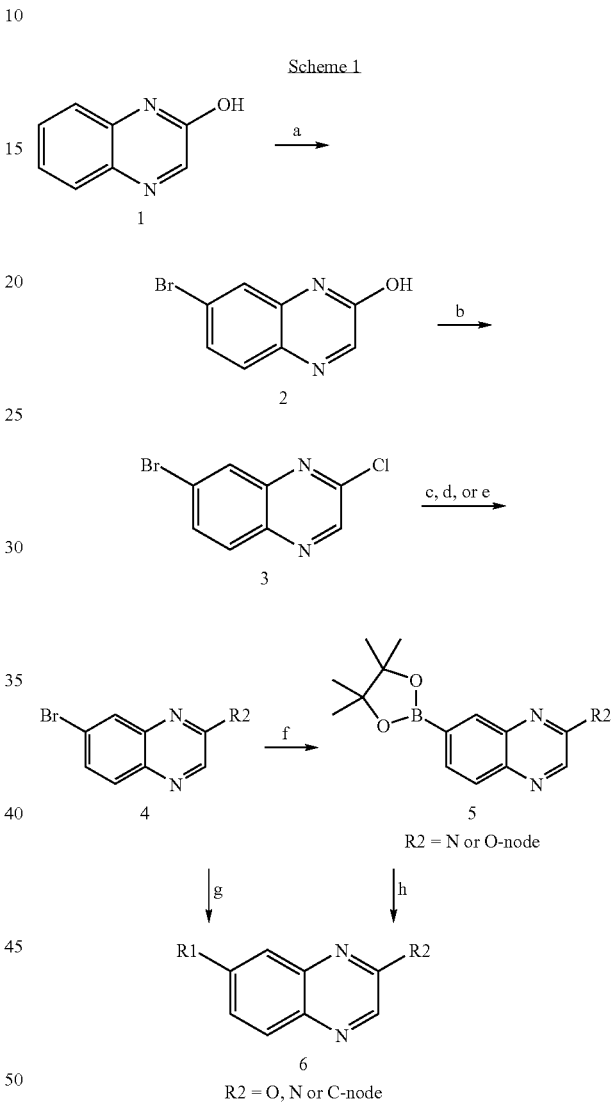

Scheme 1

Conditions: a) Bromine, acetic acid, rt; b) POCl$_3$, 120° C.; c) HNR$_1$R$_2$, DMF, 25° C.-120° C.; d) NaH, HOR$_1$, DMF, 25° C.-120° C.; e) aryl or heteroaryl (R2) boronic or boronate ester, palladium catalyst, K$_2$CO$_3$, NaHCO$_3$ or Na$_2$CO$_3$, water, dioxane or DMF, heat; or (R2) amide, palladium catalyst, xantphos, Cs$_2$CO$_3$ 1,4-dioxane, 100° C.; or aryl or heteroaryl (R2) stannane, palladium catalyst, 1,4-dioxane, 100° C.; f) bis(pinacolato)diboron, potassium acetate, palladium catalyst, dioxane, heat; g) aryl or heteroaryl (R1) bromide, palladium catalyst, K$_2$CO$_3$, NaHCO$_3$ or Na$_2$CO$_3$, water, dioxane or DMF, 100 heat; h) aryl or heteroaryl (R1) boronic or boronate ester, palladium catalyst, K$_2$CO$_3$, NaHCO$_3$ or Na$_2$CO$_3$, water, dioxane or DMF, heat.

Scheme 2 describes the removal of an amine protecting group when it is necessary to protect an amine before a coupling reaction (such as in steps C, D, or E in Scheme 1 above) can be carried out. For example, a Boc-protected amine such as compound 7 can be treated with trifluoroacetic acid in a suitable solvent (such as acetonitrile) at rt to furnish compounds of the present invention such as compound 8.

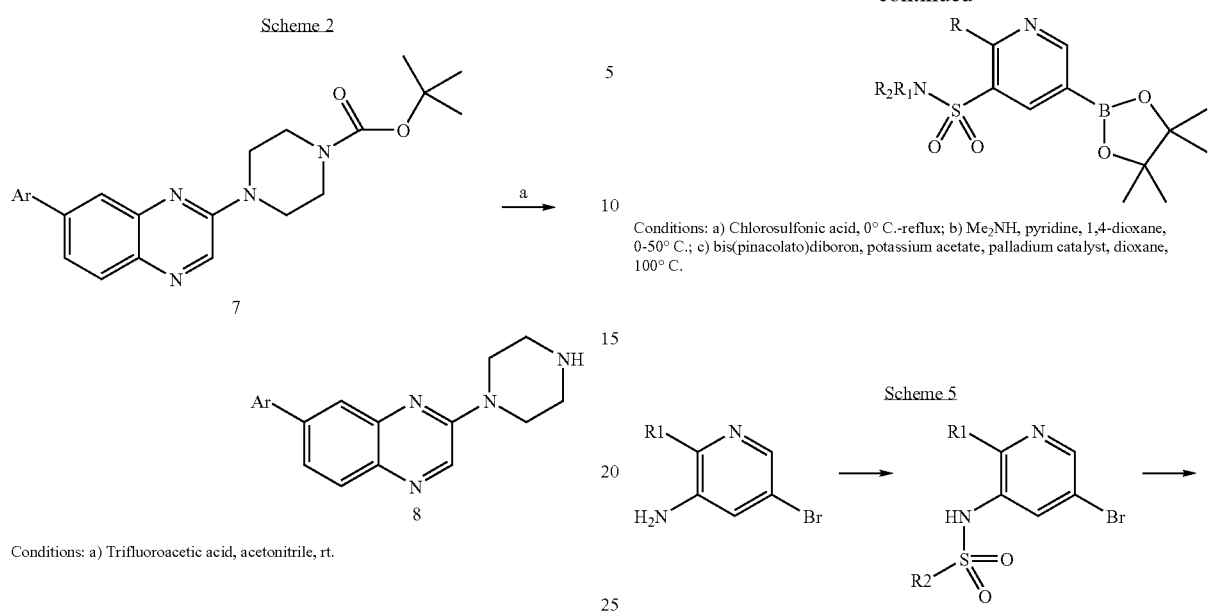

Conditions: a) Trifluoroacetic acid, acetonitrile, rt.

Schemes 3, 4, 5 and 6 describe exemplary preparations of non-commercial intermediate amines, bromides or boronate esters used.

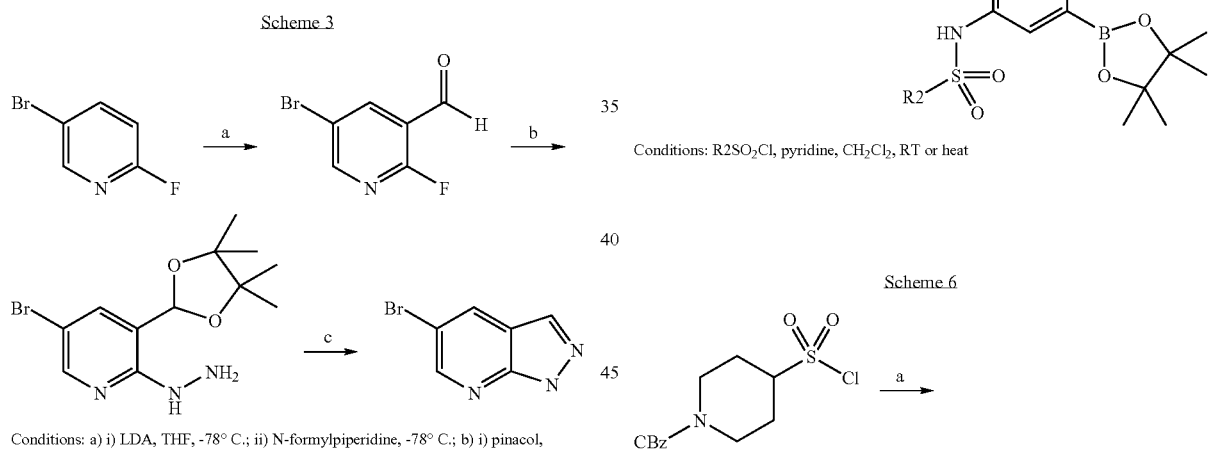

Conditions: a) i) LDA, THF, -78° C.; ii) N-formylpiperidine, -78° C.; b) i) pinacol, p-TsOH, benzene, reflux; ii) anhydrous hydrazine, DIPEA, EtOH, reflux,; c) conc aq HCl (36.5%-38%), EtOH, H₂O, 60° C. to rt.

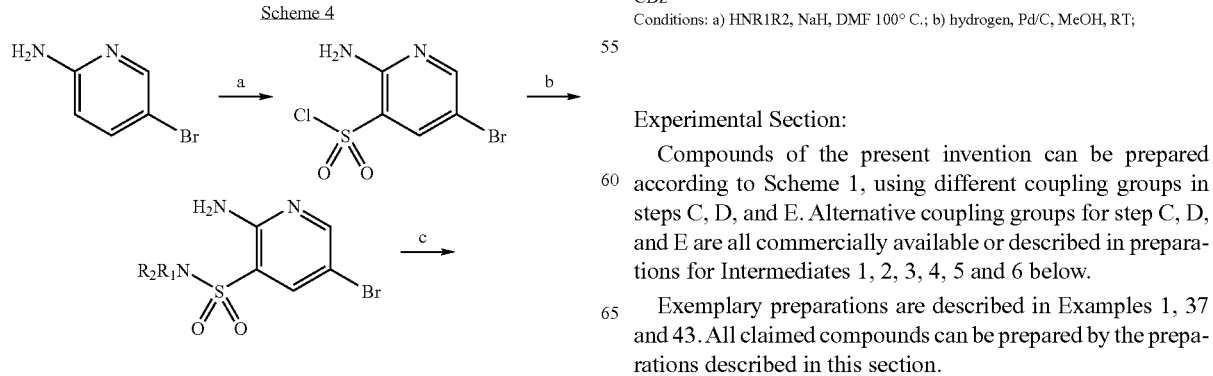

Conditions: a) Chlorosulfonic acid, 0° C.-reflux; b) Me₂NH, pyridine, 1,4-dioxane, 0-50° C.; c) bis(pinacolato)diboron, potassium acetate, palladium catalyst, dioxane, 100° C.

Conditions: R2SO₂Cl, pyridine, CH₂Cl₂, RT or heat

Conditions: a) HNR1R2, NaH, DMF 100° C.; b) hydrogen, Pd/C, MeOH, RT;

Experimental Section:

Compounds of the present invention can be prepared according to Scheme 1, using different coupling groups in steps C, D, and E. Alternative coupling groups for step C, D, and E are all commercially available or described in preparations for Intermediates 1, 2, 3, 4, 5 and 6 below.

Exemplary preparations are described in Examples 1, 37 and 43. All claimed compounds can be prepared by the preparations described in this section.

EXAMPLE 1

Preparation of 2-(4-morpholinyl)-7-(1H-pyrazolo[3,4-b]pyridin-5-yl)quinoxaline

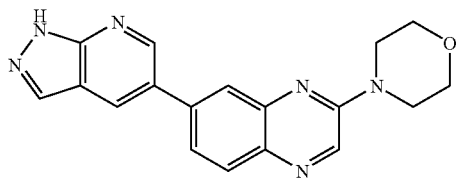

a) 7-bromo-2(1H)-quinoxalinone

Prepared according to the procedure described in *Journal of Medicinal Chemistry*, 1981, 24(1), 93-101.

b) 7-Bromo-2-chloroquinoxaline

A slurry of 7-bromo-2(1H)-quinoxalinone (22.2 mmol) in neat phosphorus oxychloride (50 ml) was heated at 120° C. for 20 hours. The reaction was cooled to ambient temperature then concentrated under reduced pressure to a purple residue. The residue was taken into ethyl acetate then slowly poured into ice-cold, saturated aqueous sodium bicarbonate solution (~100 ml) and extracted with ethyl acetate. The extracts were washed with saturated aqueous sodium bicarbonate and brine then dried over anhydrous sodium sulfate and decolorizing charcoal. The slurry was filtered through Celite then concentrated under reduced pressure to give the title compound (3.0 g, 55%) as a white solid. MS(ES)+ m/e 242.9; 244.8 [M+]+.

c) 7-Bromo-2-(4-morpholinyl)quinoxaline

A solution of 7-bromo-2-chloroquinoxaline (6.16 mmol) in N,N-dimethylformamide (20 ml) was treated with an amine or alcohol such as neat morpholine (18.5 mmol) then heated at 80° C. for 1 hour. The reaction was cooled to ambient temperature then concentrated under reduced pressure to a yellow residue. The residue was taken into ethyl acetate and washed with portions of saturated aqueous sodium bicarbonate. The organic phase was dried over anhydrous sodium sulfate and decolorizing charcoal then filtered through Celite. The filtrate was concentrated under reduced pressure to give (1.43 g, 95%) as a yellow solid. MS(ES)+ m/e 293.7; 295.9 [M+]+.

d) 2-(4-Morpholinyl)-7-(4,4,5,5-tetramethyl-1,3,2-dioxaborolan-2-yl)quinoxaline

A slurry of 7-bromo-2-(4-morpholinyl)quinoxaline (0.67 mmol), bis(pinacolato)diboron (0.87 mmol), potassium acetate (1.33 mmol) and [1,1'-bis(diphenylphosphino)ferrocene]dichloropalladium(II) dichloromethane complex (1:1) (0.03 mmol) in anhydrous 1,4-dioxane (10 ml) was heated at 110° C. for 18 hours. The reaction mixture was cooled to ambient temperature then filtered through a short pad of silica (~15 g) topped with anhydrous sodium sulfate (~5 g), rinsing with ethyl acetate. The filtrate was concentrated under reduced pressure to a brown residue then purified by column chromatography on silica (15% hexanes in ethyl acetate). The desired fractions were combined and concentrated to give the title compound (186 mg, 81%) as a yellow solid. MS(ES)+ m/e 342.0 [M+]+.

e) 2-(4-Morpholinyl)-7-(1H-pyrazolo[3,4-b]pyridin-5-yl)quinoxaline

A slurry of 2-(4-morpholinyl)-7-(4,4,5,5-tetramethyl-1,3,2-dioxaborolan-2-yl)quinoxaline (0.56 mmol), a heteroaryl bromide such as 5-bromo-1H-pyrazolo[3,4-b]pyridine (0.47 mmol), [1,1'-bis(diphenylphosphino)ferrocene]dichloropalladium(II) dichloromethane complex (1:1) (0.05 mmol) and 2 M aqueous sodium carbonate (1.88 mmol) in 1,4-dioxane (5 ml) was heated at 110° C. for 18 hours. The reaction was cooled to ambient temperature then filtered through a short pad of silica (~15 g) topped with anhydrous sodium sulfate (~5 g), rinsing well with ethyl acetate. The filtrate was concentrated under reduced pressure to a brown residue then purified by column chromatography on silica (10% hexanes in ethyl acetate). The desired fractions were combined and concentrated to give the title compound (40 mg, 26%) as a light yellow solid. MS(ES)+ m/e 333.1 [M+H]+.

The following compounds were or can be prepared following the procedures used to prepare Example 1:

| Example | Structure | MS(ES) [M + H]+ |
| --- | --- | --- |
| 2 | 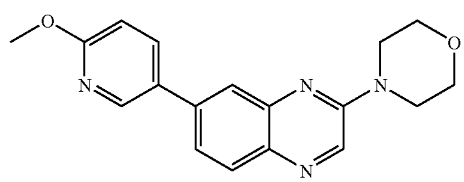 | 323 |
| 3 | 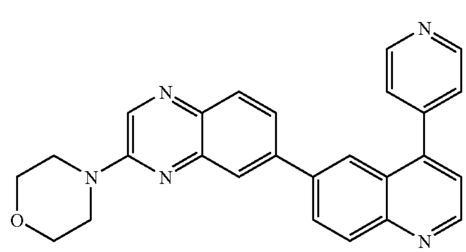 | 420 |

US 7,592,342 B2

-continued

| Example | Structure | MS(ES) [M + H]+ |
|---|---|---|
| 4 | 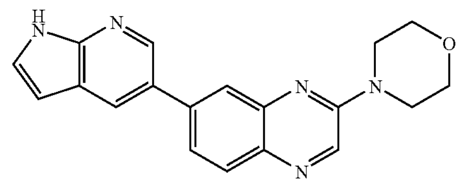 | 332 |
| 5 | 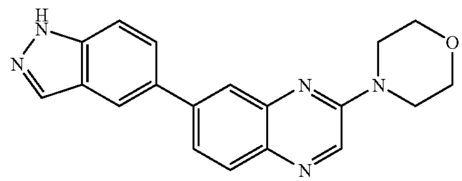 | 332 |
| 6 | 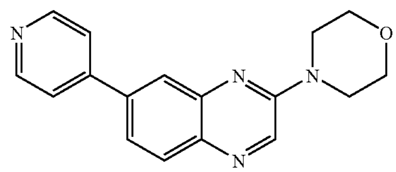 | 293 |
| 7 | 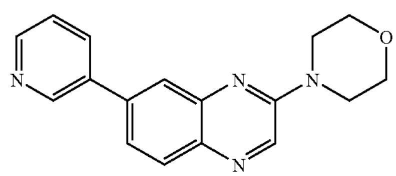 | 293 |
| 8 | 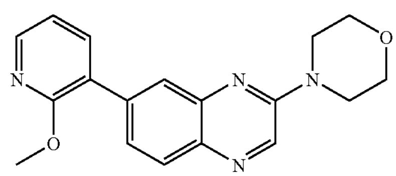 | 323 |
| 9 | 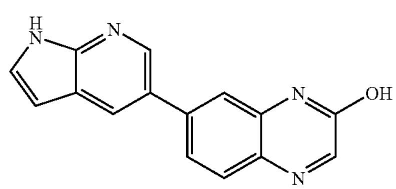 | 263 |
| 10 | 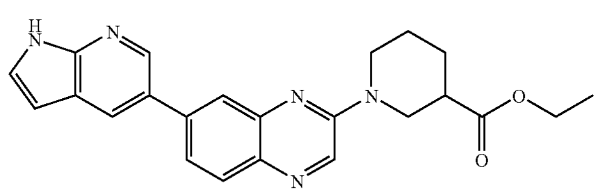 | 402 |
| 11 | 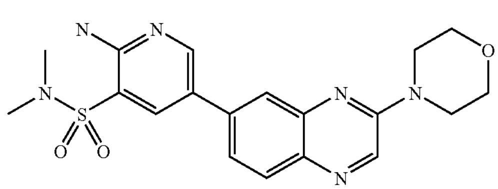 | 415 |

-continued

| Example | Structure | MS(ES) [M + H]+ |
|---|---|---|
| 12 | 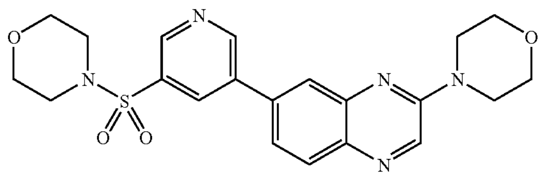 | 442 |
| 13 | 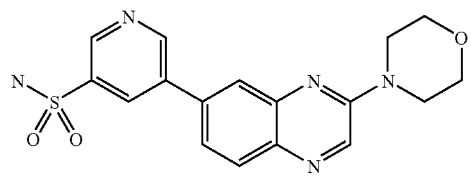 | 372 |
| 14 | 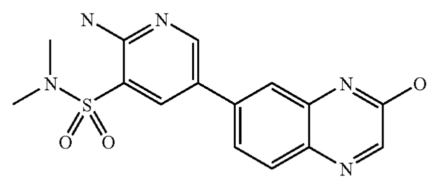 | 346 |
| 15 | 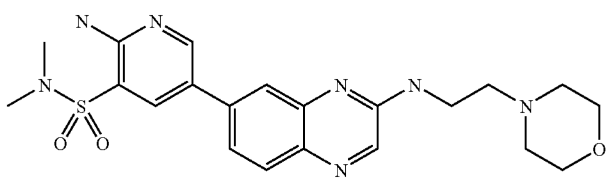 | 458 |
| 16 | 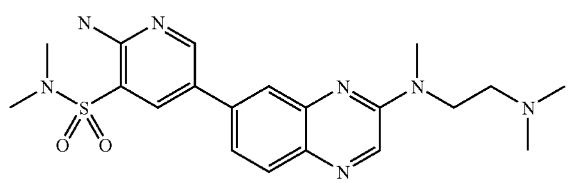 | 430 |
| 17 | 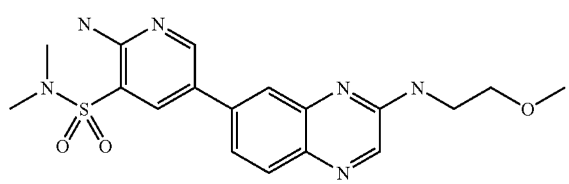 | 403 |
| 18 | 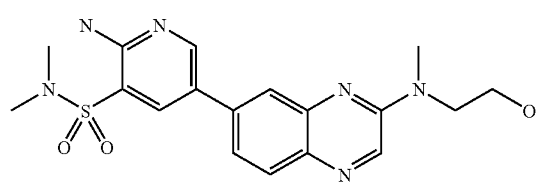 | 403 |
| 19 | 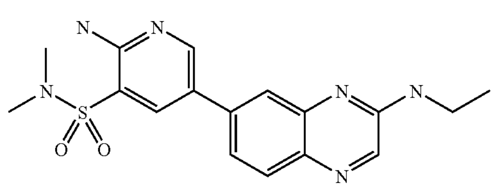 | 373 |

-continued

| Example | Structure | MS(ES) [M + H]+ |
|---|---|---|
| 20 | 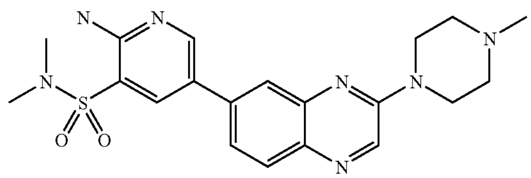 | 427 |
| 21 | 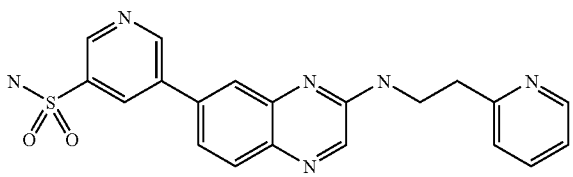 | 407 |
| 22 | 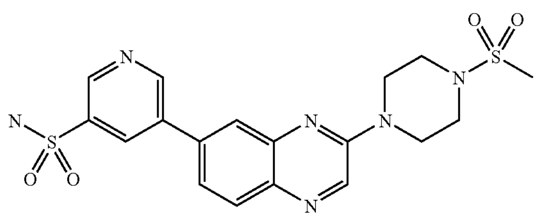 | 448 |
| 23 | 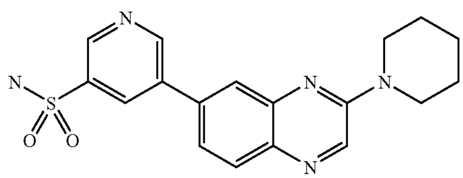 | 369 |
| 24 | 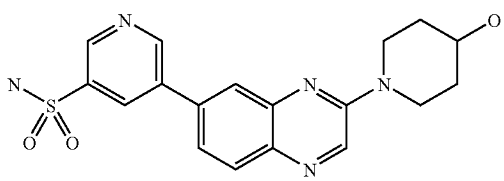 | 386 |
| 25 | 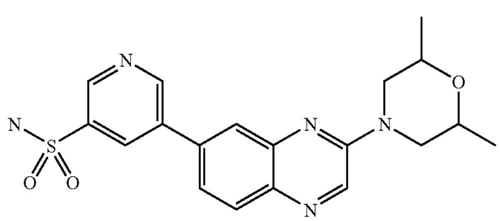 | 399 |
| 26 | 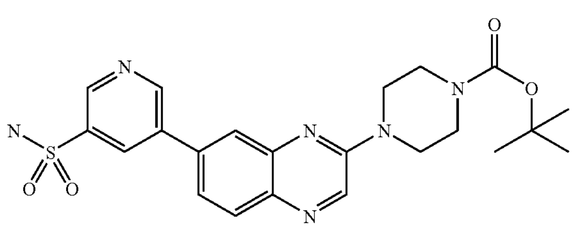 | 471 |
| 27 | 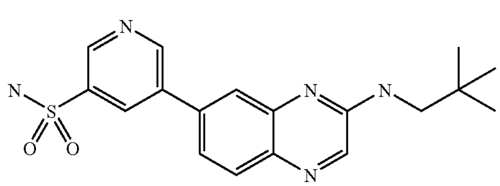 | 372 |

-continued

| Example | Structure | MS(ES) [M + H]+ |
|---------|-----------|-----------------|
| 28 | 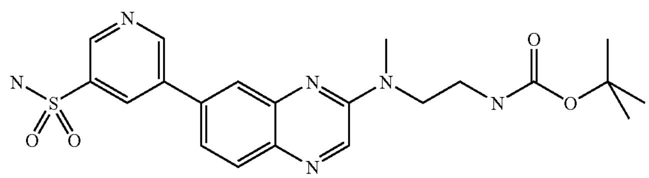 | 459 |
| 29 | 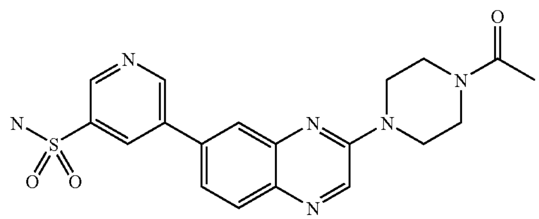 | 413 |
| 30 | 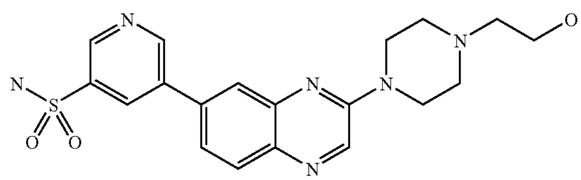 | 415 |
| 31 | 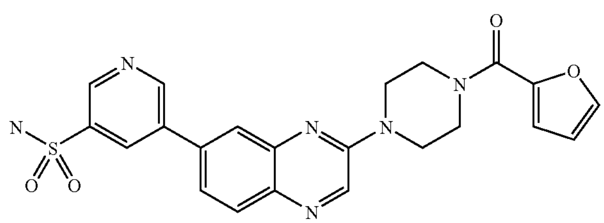 | 465 |
| 32 | 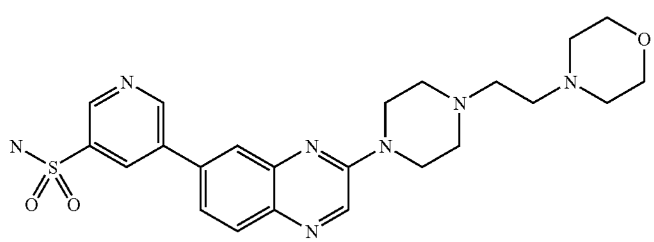 | 484 |
| 33 | 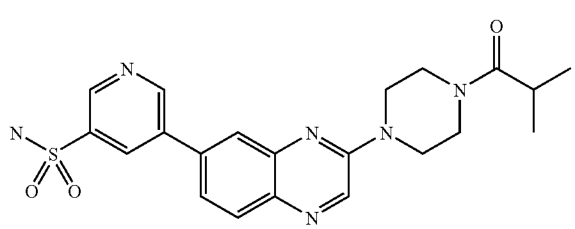 | 441 |
| 34 | 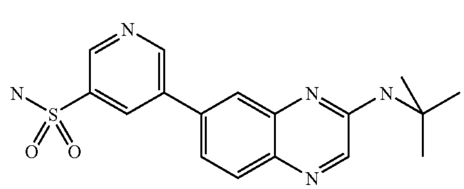 | 358 |

-continued

| Example | Structure | MS(ES) [M + H]+ |
|---|---|---|
| 35 | 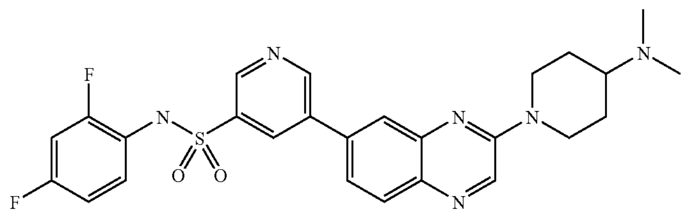 | 525 |
| 36 | 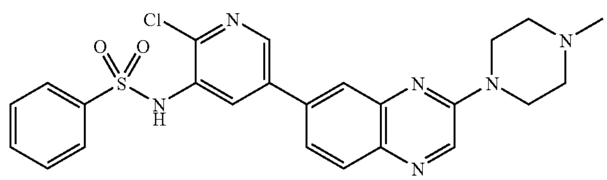 | 495 |
| 37 | 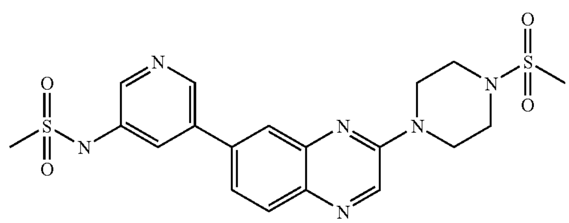 | 463 |
| 38 | 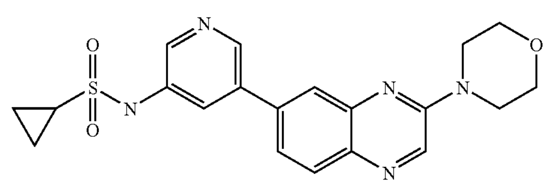 | 412 |
| 39 | 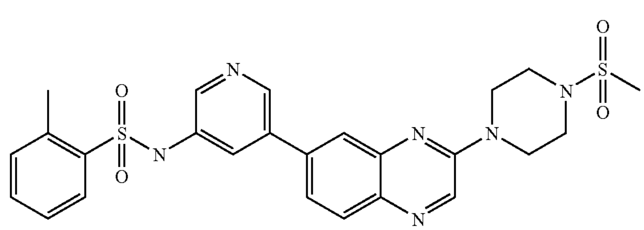 | 539 |
| 40 | 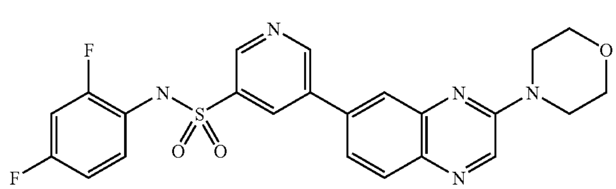 | 484 |
| 41 | 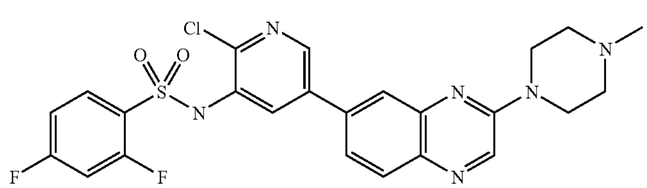 | 531 |

-continued

| Example | Structure | MS(ES) [M + H]+ |
| --- | --- | --- |
| 42 | 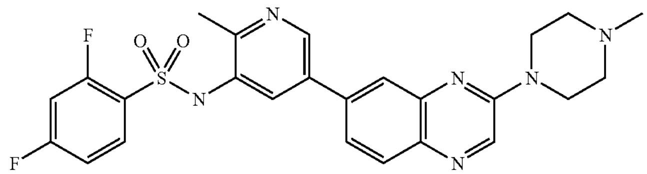 | 511 |
| 43 | 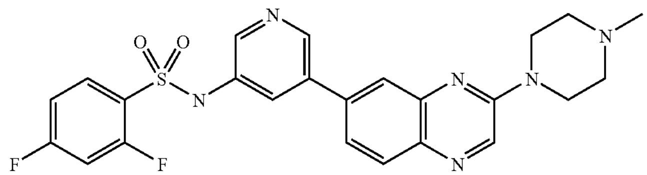 | 497 |
| 44 | 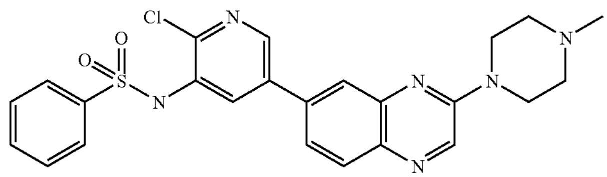 | 495 |
| 45 | 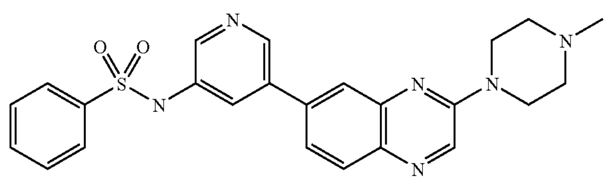 | 461 |
| 46 | 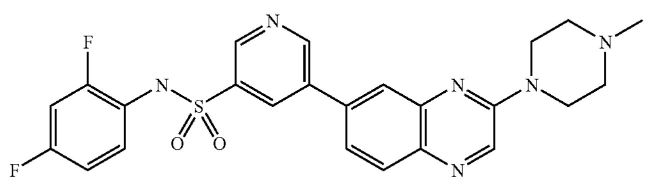 | 497 |
| 47 | 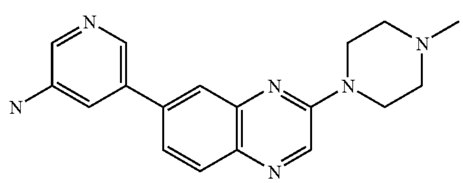 | 320 |
| 48 | 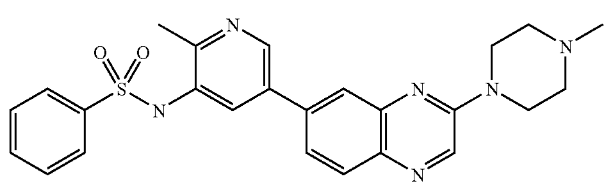 | 475 |
| 49 | 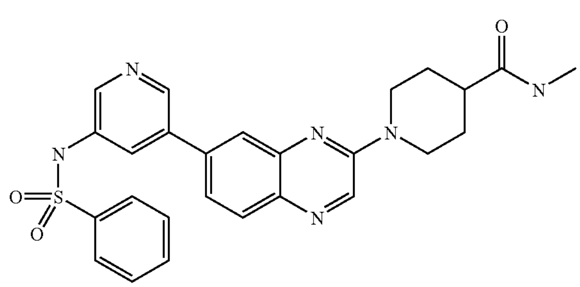 | 503 |

-continued
| Example | Structure | MS(ES) [M + H]+ |
|---|---|---|
| 50 | 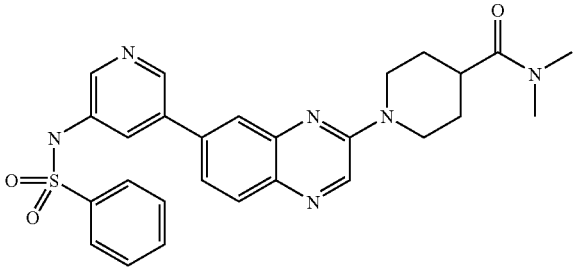 | 517 |
| 51 | 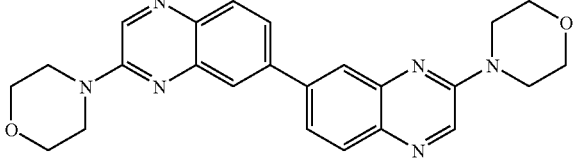 | 429 |
| 52 | 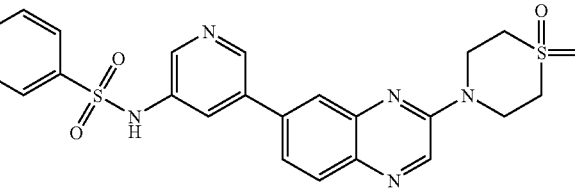 | 496 |
| 53 | 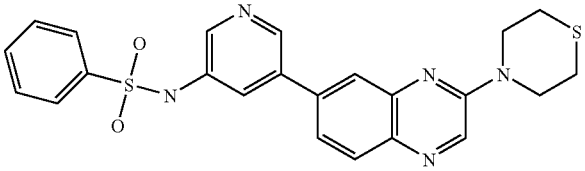 | 464 |
| 54 | 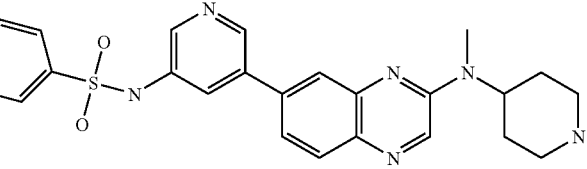 | 489 |
| 55 | 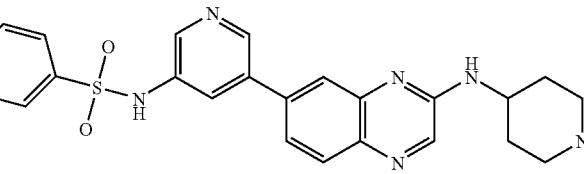 | 461 |
| 56 | 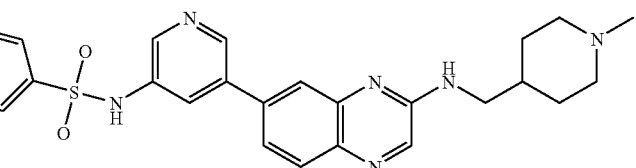 | 489 |

-continued
| Example | Structure | MS(ES) [M + H]+ |
|---|---|---|
| 57 | 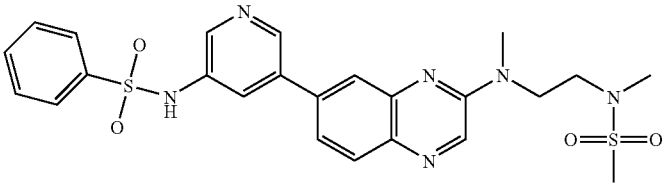 | 527 |
| 58 | 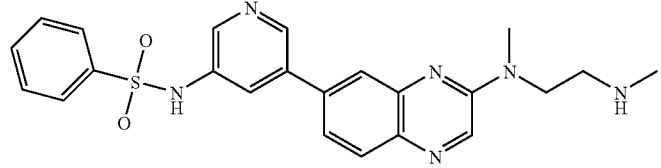 | 449 |
| 59 | 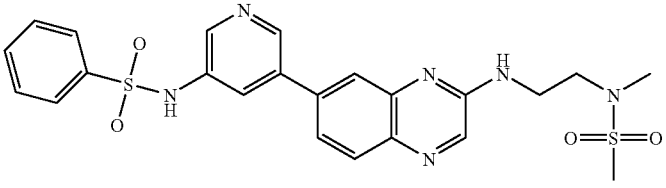 | 513 |
| 60 | 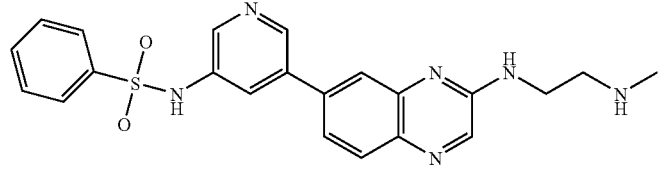 | 435 |
| 61 | 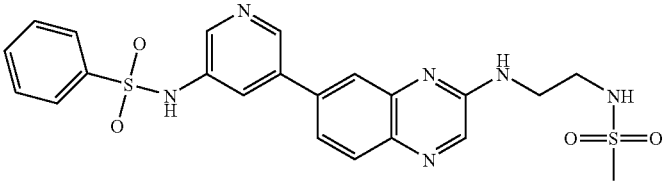 | 499 |
| 62 | 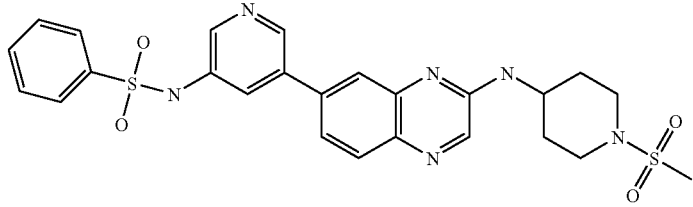 | 539 |
| 63 | 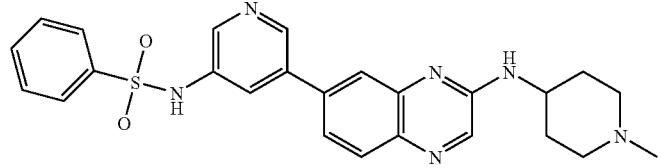 | 475 |

-continued

| Example | Structure | MS(ES) [M + H]+ |
|---|---|---|
| 64 | 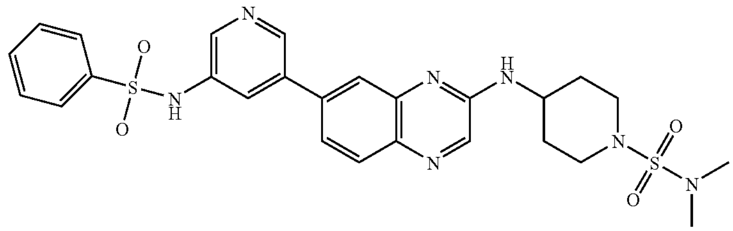 | 568 |
| 65 | 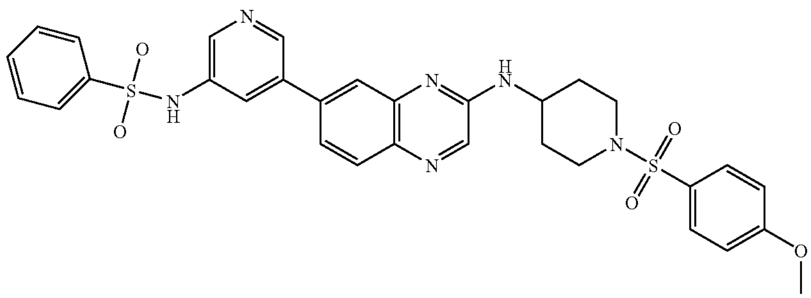 | 631 |
| 66 | 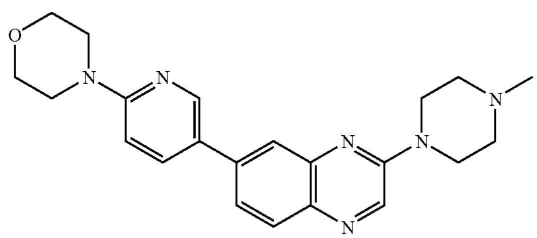 | 391 |
| 67 | 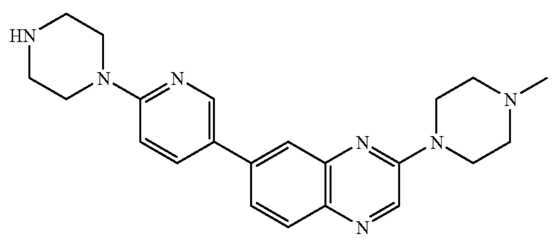 | 390 |
| 68 | 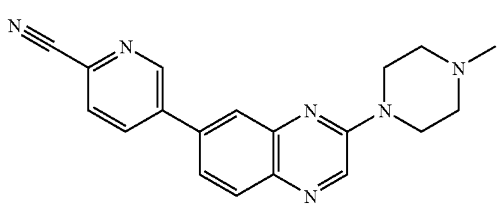 | 331 |

EXAMPLE 69

Preparation of 2-amino-N,N-dimethyl-5-[3-(4-pyridinyl)-6-quinoxalinyl]-3-pyridinesulfonamide

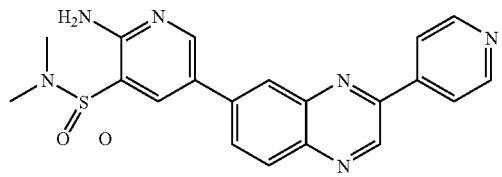

a) 7-bromo-2-(4-pyridinyl)quinoxaline

A mixture of 7-bromo-2-chloroquinoxaline (2.05 mmol), pyridine-4-boronic acid (2.05 mmol), [1,1'-bis(diphenylphosphino)-ferrocene]dichloropalladium(II) dichloromethane complex (1:1) (0.1025 mmol), 2M aqueous potassium carbonate (5 mL) and anhydrous 1,4-dioxane (15 mL) was heated at 100° C. for 16.5 h in a sealed pressure vessel. After cooling to room temperature, the organic layer was separated and purified directly on silica gel, eluting with 50-100% ethyl acetate in hexanes to provide the title compound as a yellow solid (382 mg, 65% yield). MS(ES)+ m/e 285.9; 287.8 [M+]+.

b) 2-amino-N,N-dimethyl-5-[3-(4-pyridinyl)-6-quinoxalinyl]-3-pyridinesulfonamide A mixture of 7-bromo-2-(4-pyridinyl)quinoxaline (0.245 mmol), 2-amino-N,N-dimethyl-5-(4,4,5,5-tetramethyl-1,3,2-dioxaborolan-2-yl)-3-pyridinesulfonamide (0.245 mmol), [1,1'-bis(diphenylphosphino)-ferrocene]dichloropalladium (II) dichloromethane complex (1:1) (0.0196 mmol), 2M aqueous potassium carbonate (2 mL) and anhydrous 1,4-dioxane (6 mL) was heated at 100° C. for 4 h in a sealed pressure vessel. After cooling to room temperature, the organic layer was separated and purified directly on silica gel, eluting with 0-10% methanol in ethyl acetate followed by a second purification by HPLC (eluting with acetonitrile: 0.1% TFA in H2O) to afford the title compound as a bright yellow solid (47 mg, 47% yield). MS(ES)+ m/e 407.2 [M+H]+.

The following compounds were or can be prepared following the procedures used to prepare Example 69:

| Compound | Structure | MS(ES) [M + H]+ |
|---|---|---|
| 70 | 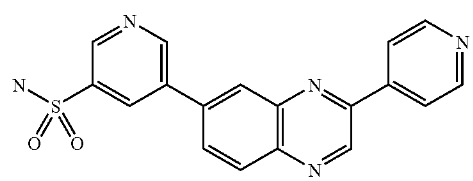 | 364 |
| 71 | 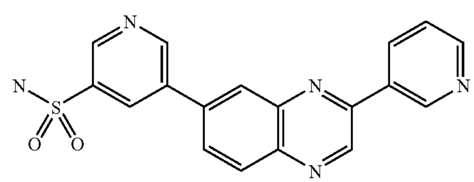 | 364 |
| 72 | 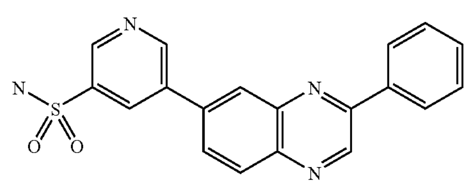 | 363 |
| 73 | 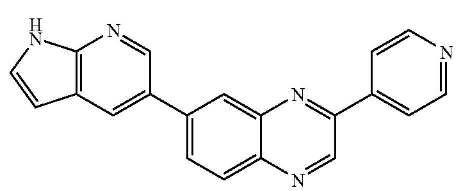 | 324 |
| 74 | 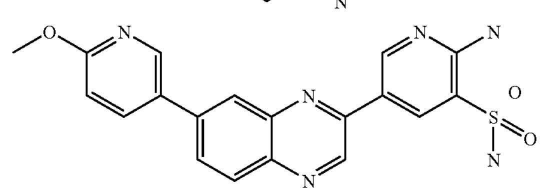 | 408 |

| Compound | Structure | MS(ES) [M + H]+ |
|---|---|---|
| 75 | 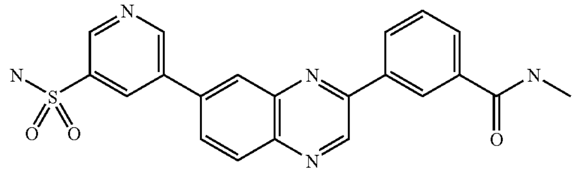 | 420 |
| 76 | 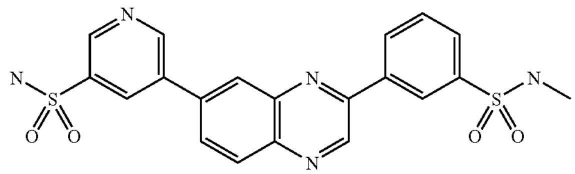 | 456 |
| 77 | 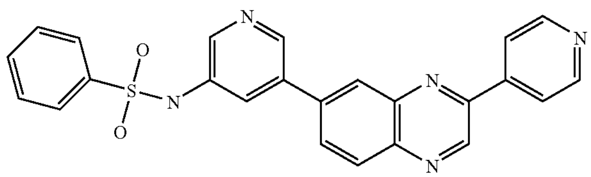 | 440 |
| 78 | 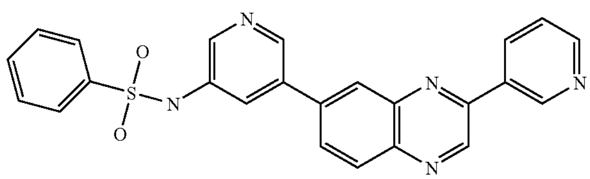 | 440 |
| 79 | 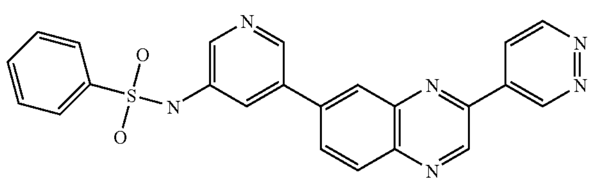 | 441 |

EXAMPLE 80

Preparation of 5-[3-(1-piperazinyl)-6-quinoxalinyl]-3-pyridinesulfonamide

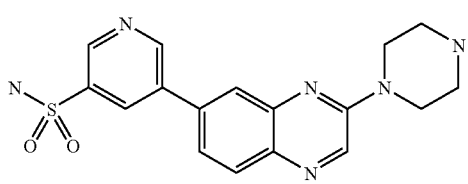

A solution of 1,1-dimethylethyl 4-{7-[5-(aminosulfonyl)-3-pyridinyl]-2-quinoxalinyl}-1-piperazinecarboxylate (0.21 mmol) (prepared according to Scheme 1) in acetonitrile (4 mL) was treated with concentrated trifluoroacetic acid (4 mL) for 2 hours. The reaction mixture was then concentrate and neutralized with saturated sodium bicarbonate (20 mL) and extracted with ethyl acetate (3×20 mL). The combined organic layers were washed with brine, dried over sodium sulfate, filtered and concentrated to yield the title product. MS(ES)+ m/e 371.0 [M+H]+.

Similar compounds were or can be prepared following the procedures used to prepare Example 80, with or without N,N'-dimethylformamide as solvent.

EXAMPLE 81

Preparation of N-{5-[3-(1-methyl-1H-pyrazol-4-yl)-6-quinoxalinyl]-3-pyridinyl}benzenesulfonamide

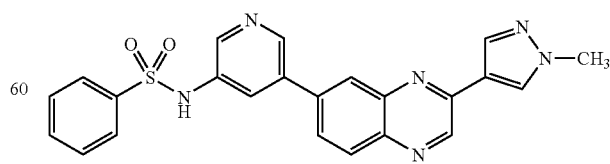

a) 7-bromo-2-(1-methyl-1H-pyrazol-4-yl)quinoxaline

A slurry of 7-bromo-2-chloroquinoxaline (10.0 mmol), 1-methyl-4-(4,4,5,5-tetramethyl-1,3,2-dioxaborolan-2-yl)-

1H-pyrazole (10.5 mmol), and [1,1'-bis(diphenylphosphino)ferrocene]dichloropalladium(II) dichloromethane complex (1:1) (0.3 mmol) in 2M aqueous potassium carbonate (15 mL) and 1,4-dioxane (40 mL) was heated at 100° C. for 4 h. The reaction mixture was cooled, poured into water (100 mL), and extracted with (3×100 mL) ethyl acetate. The combined organic layers were filtered through a pad of Celite while rinsing with water and ethyl acetate. The filtrate was separated and the organic layer was dried over sodium sulfate, filtered, and concentrated in vacuo. Purification of the residue by silica gel chromatography (40-70% ethyl acetate/hexanes) provided the title compound as a yellow solid (1.73 g, 57%). MS(ES)+ m/e 289, 291 [M+H]$^+$.

b) N-{5-[3-(1-methyl-1H-pyrazol-4-yl)-6-quinoxalinyl]-3-pyridinyl}benzenesulfonamide A mixture of 7-bromo-2-(1-methyl-1H-pyrazol-4-yl)quinoxaline (5.98 mmol), N-[5-(4,4,5,5-tetramethyl-1,3,2-dioxaborolan-2-yl)-3-pyridinyl]benzenesulfonamide (6.78 mmol), and [1,1'-bis(diphenylphosphino)ferrocene]dichloropalladium(II) dichloromethane complex (1:1) (0.18 mmol) in 2M aqueous sodium carbonate (15 mL) and 1,4-dioxane (40 mL) was heated at 100° C. for 22 h. Additional N-[5-(4,4,5,5-tetramethyl-1,3,2-dioxaborolan-2-yl)-3-pyridinyl]benzenesulfonamide (0.83 mmol), [1,1'-bis(diphenylphosphino)ferrocene]dichloropalladium(II) dichloromethane complex (1:1) (0.09 mmol), and 2M aqueous potassium carbonate (3 mL) were added and the reaction mixture was heated at 100° C. for 22 h for complete consumption of starting material. The reaction mixture was cooled, diluted with diethyl ether (30 mL), and filtered through a pad of Celite while rinsing with (2×30 mL) diethyl ether. The organic layer was poured into a separatory funnel containing water (100 mL) and the layers were separated. The aqueous layer was acidified with 6N aqueous HCl until the pH was approximately 7 and then further extracted with (3×200 mL) ethyl acetate. The combined organic layers were dried over sodium sulfate with decolorizing activated carbon, filtered through a pad of Celite while rinsing with (2×100 mL) ethyl acetate, and concentrated in vacuo. The filtrate was separated and the organic layer was dried over sodium sulfate, filtered, and concentrated in vacuo. Recrystallization of the residue from hot ethyl acetate afforded the title product as an ivory solid (804 mg, 30%). Additional product was obtained from the concentrated mother liquors after purification by silica gel chromatography (70-100% ethyl acetate/hexanes) followed by precipitation from cold ethyl acetate (534 mg, 20%). MS(ES)+ m/e 443 [M+H]$^+$.

Related analogs such as the following were or can be prepared following the general procedures in Example 81 by varying the choice of boronate ester and heteroaryl halide coupling partners. Some analogs could be isolated by direct purification of the organic layer by alternative purification methods such as reverse phase Gilson HPLC, silica gel chromatography, recrystallization from ethanol, or trituration from other solvents.

| Example | Structure | MS(ES) [M + H]$^+$ |
|---|---|---|
| 82 | 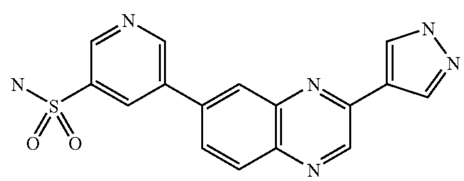 | 353 |
| 83 | 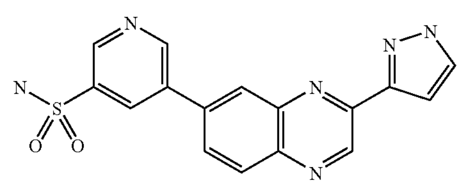 | 353 |
| 84 | 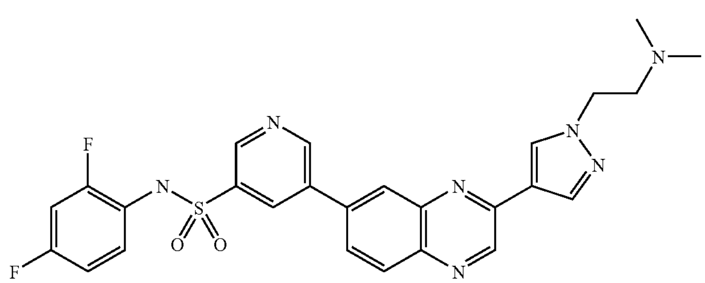 | 536 |
| 85 | 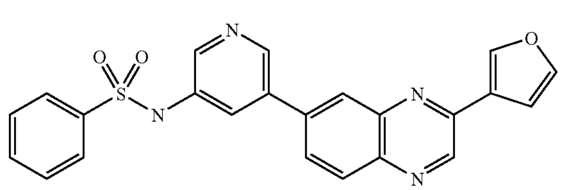 | 429 |

-continued

| Example | Structure | MS(ES) [M + H]+ |
|---|---|---|
| 86 | 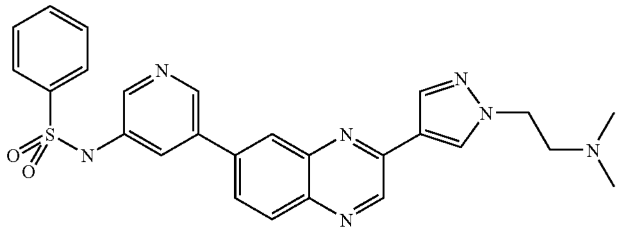 | 500 |
| 87 | 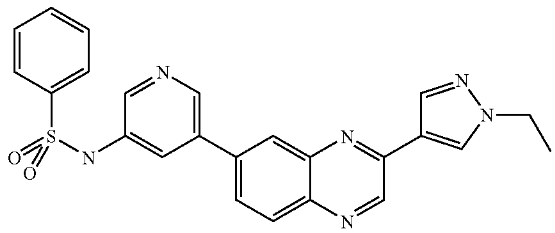 | 457 |
| 88 | 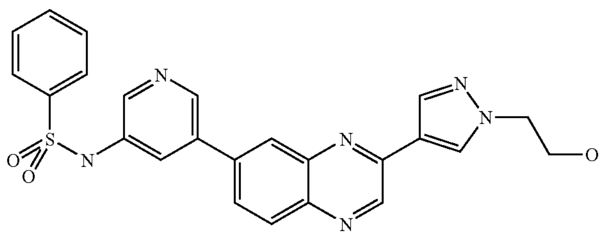 | 473 |
| 89 | 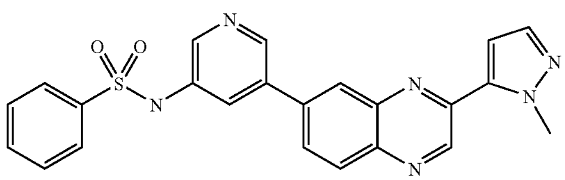 | 443 |
| 90 | 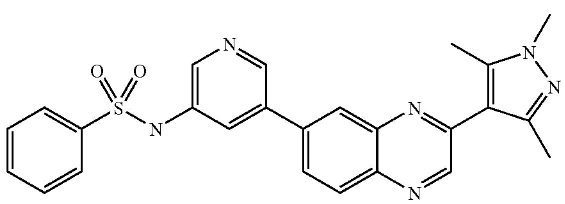 | 471 |
| 91 | 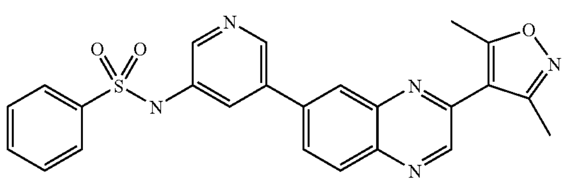 | 458 |
| 92 | 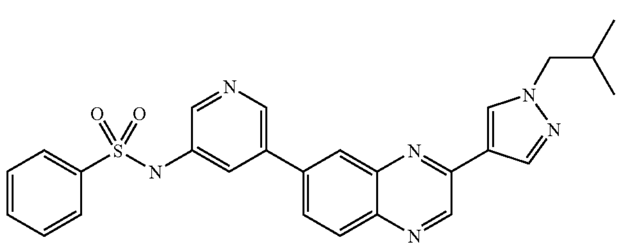 | 485 |

-continued

| Example | Structure | MS(ES) [M + H]+ |
|---------|-----------|-----------------|
| 93 | 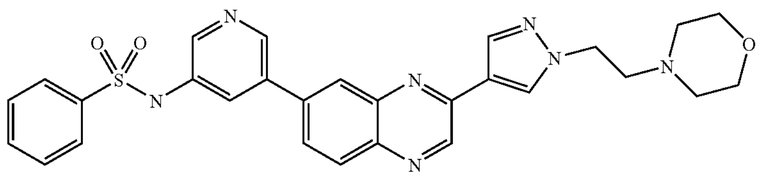 | 542 |
| 94 | 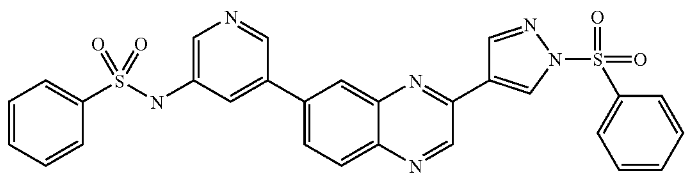 | 569 |
| 95 | 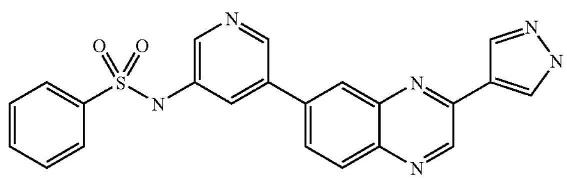 | 429 |
| 96 | 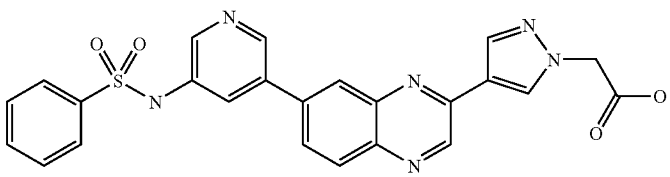 | 487 |
| 97 | 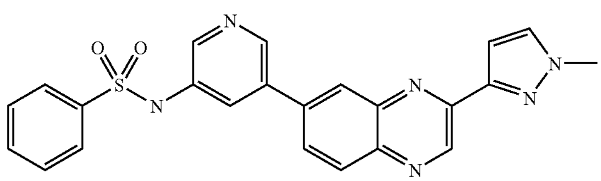 | 443 |
| 98 | 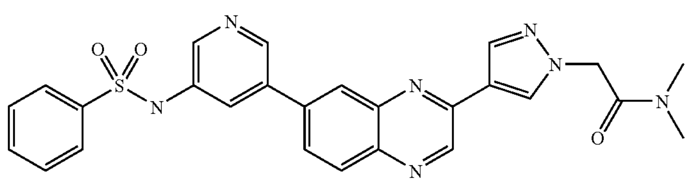 | 514 |
| 99 | 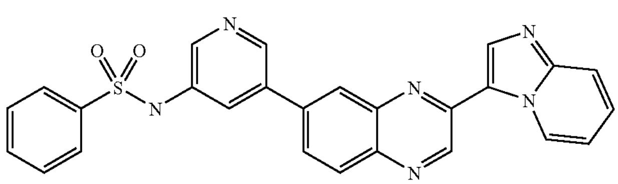 | 479 |
| 100 | 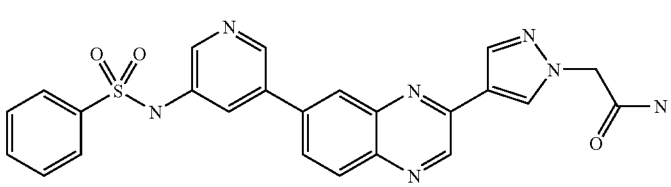 | 486 |

| Example | Structure | MS(ES) [M + H]+ |
|---|---|---|
| 101 | 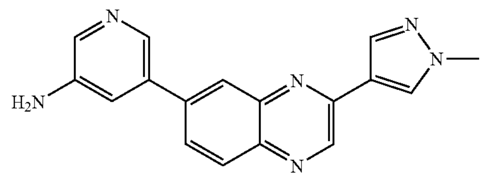 | 303 |
| 102 | 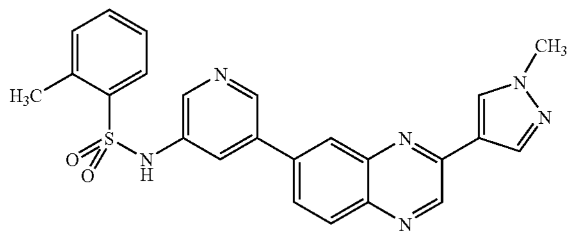 | 457 |
| 103 | 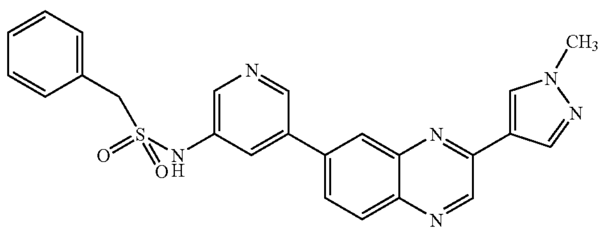 | 457 |
| 104 | 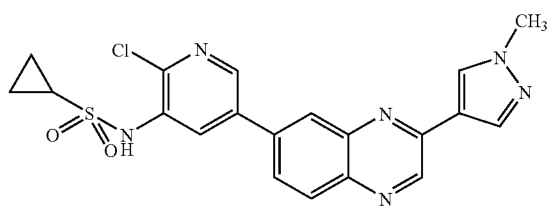 | 442 |
| 105 | 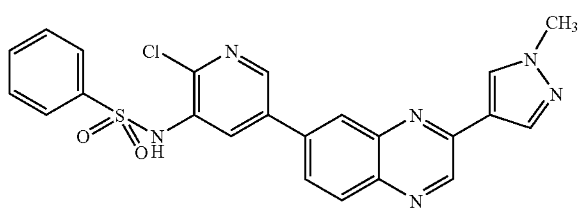 | 478 |
| 106 | 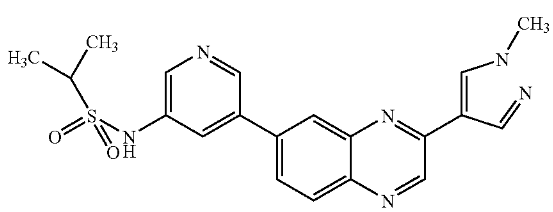 | 409 |
| 107 | 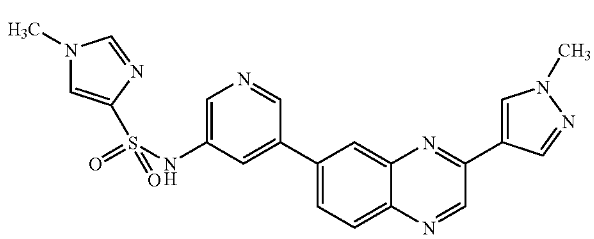 | 447 |

| Example | Structure | MS(ES) [M + H]+ |
|---|---|---|
| 108 | 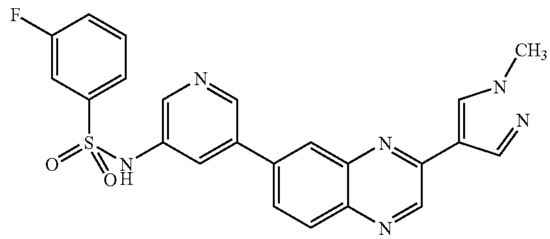 | 461 |
| 109 | 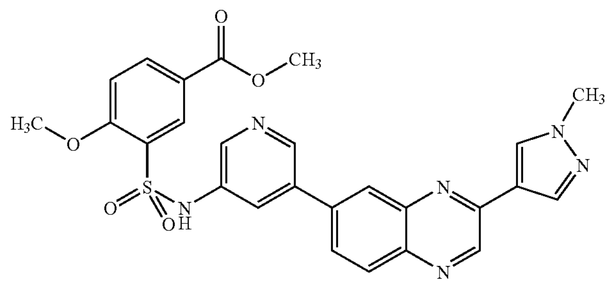 | 531 |
| 110 | 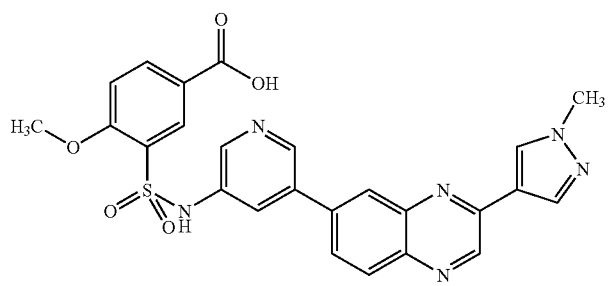 | 517 |
| 111 | 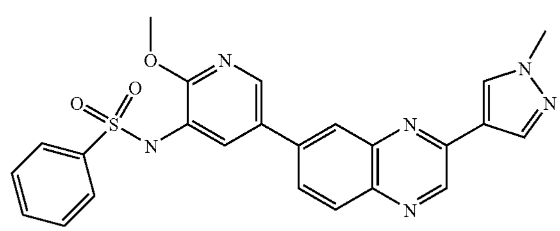 | 473 |
| 112 | 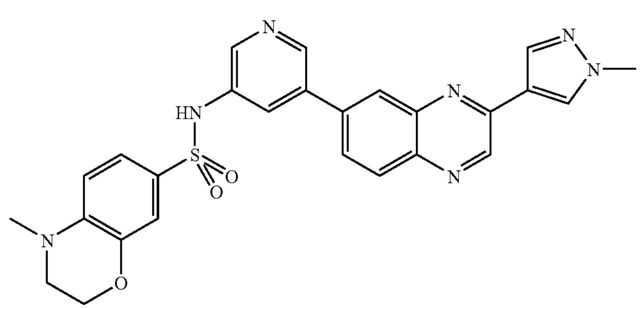 | 514 |
| 113 | 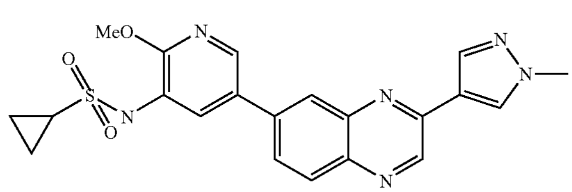 | 437 |

-continued

| Example | Structure | MS(ES) [M + H]+ |
|---|---|---|
| 114 | 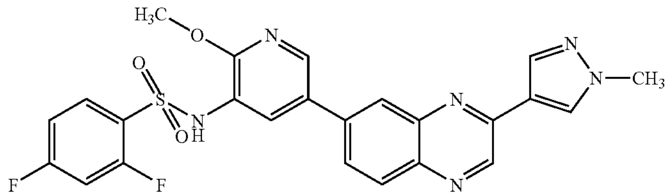 | 509 |
| 115 | 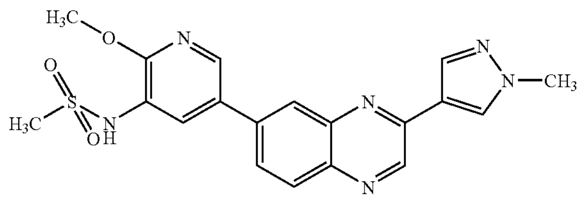 | 411 |
| 116 | 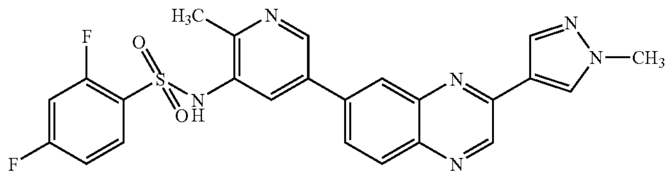 | 493 |
| 117 | 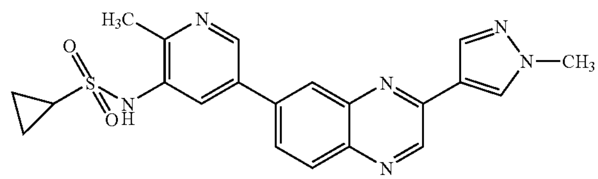 | 421 |
| 118 | 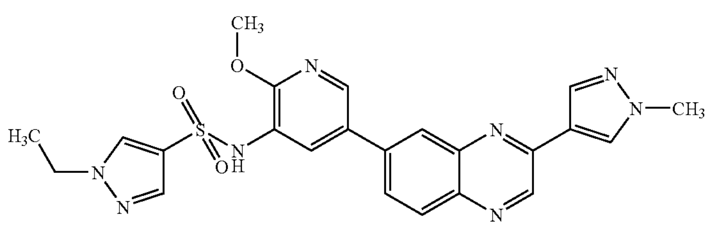 | 491 |

EXAMPLE 119

Preparation of 2,4-difluoro-N-{5-[3-(1-methyl-1H-pyrazol-4-yl)-6-quinoxalinyl]-3-pyridinyl}benzenesulfonamide

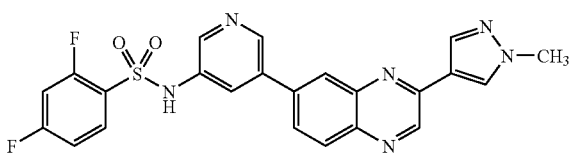

A mixture of 2-(1-methyl-1H-pyrazol-4-yl)-7-(4,4,5,5-tetramethyl-1,3,2-dioxaborolan-2-yl)quinoxaline (9.22 mmol), N-(5-bromo-3-pyridinyl)-2,4-difluorobenzenesulfonamide (8.13 mmol), and [1,1'-bis(diphenylphosphino)ferrocene]dichloropalladium(II) dichloromethane complex (1:1) (0.404 mmol) in 2M aqueous sodium carbonate (40 mL) and 1,4-dioxane (40 mL) was heated at 100° C. for 1 h. Upon cooling, the reaction mixture separated into two layers (aqueous and organic). The organic layer was partitioned between ethyl acetate (50 mL) and water (25 mL). The two aqueous layers were then combined and the pH was adjusted to ~7 with 2N aqueous HCl. A solid precipitated and was filtered away from the solution. The solid was dried in vacuo and then desiccated over $P_2O_5$ to afford the title product (2.5 g, 64%). MS(ES)+ m/e 479 [M+H]+.

EXAMPLE 120

Preparation of 4-cyano-N-{5-[3-(1-methyl-1H-pyrazol-4-yl)-6-quinoxalinyl]-3-pyridinyl}benzenesulfonamide

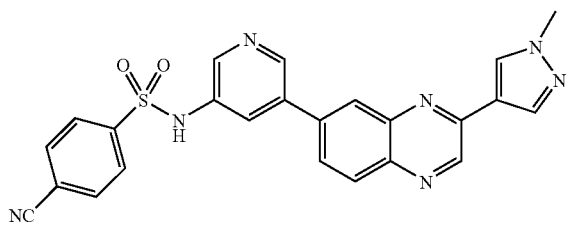

To a solution of 5-[3-(1-methyl-1H-pyrazol-4-yl)-6-quinoxalinyl]-3-pyridinamine (52 g, 0.172 mmol) in pyridine (1.7 mL) was added 4-cyanobenzenesulfonyl chloride (56 mg, 0.278 mmol). The reaction mixture was stirred at room temperature overnight. Monitoring by LCMS still showed 30% of starting material. An additional portion of 4-cyanobenzenesulfonyl chloride (17 mg, 0.084 mmol) was added to the reaction mixture and after stirring for a further 30 minutes, all starting material was consumed. Cold water was poured into the reaction resulting in precipitate formation. This solid was collected by filtration, washed with water and dried under vacuum to give the title compound (54 mg, 67%) as a brown colored solid. MS(ES)+ m/e 468 [M+H]$^+$.

The following compounds were or can be prepared following the general procedures used to prepare the compound of Example 120 above:

| Compound | Structure | MS(ES) [M + H]$^+$ |
|---|---|---|
| 121 | 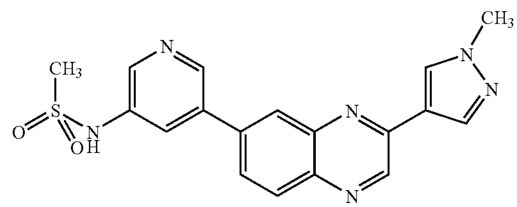 | 381 |
| 122 | 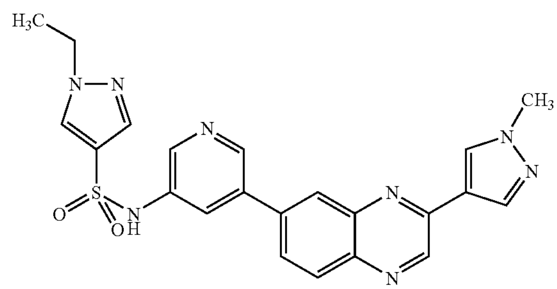 | 461 |
| 123 | 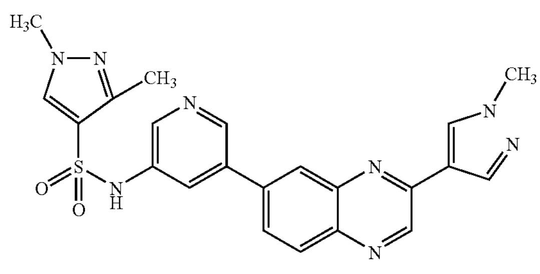 | 461 |
| 124 | 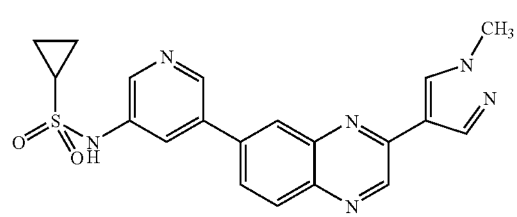 | 407 |

| Compound | Structure | MS(ES) [M + H]+ |
|---|---|---|
| 125 | 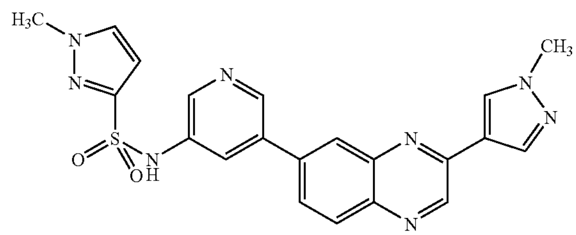 | 447 |
| 126 | 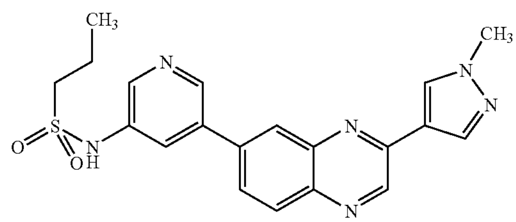 | 409 |
| 127 | 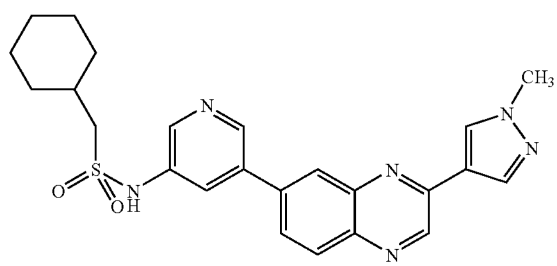 | 463 |
| 128 | 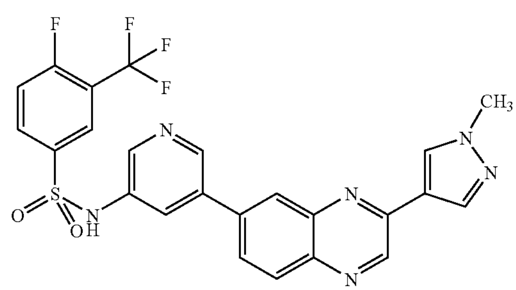 | 529 |
| 129 | 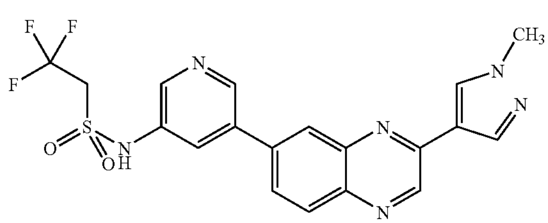 | 449 |
| 130 | 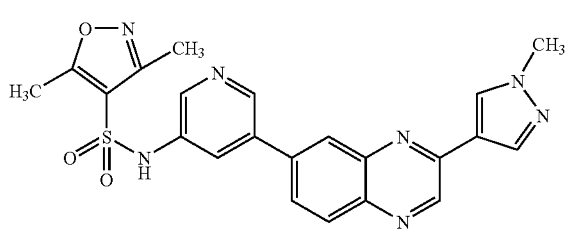 | 462 |

-continued

| Compound | Structure | MS(ES) [M + H]+ |
|---|---|---|
| 131 | 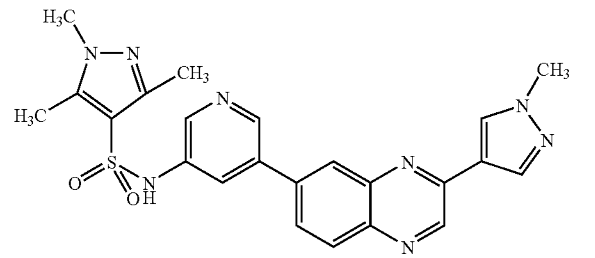 | 475 |
| 132 | 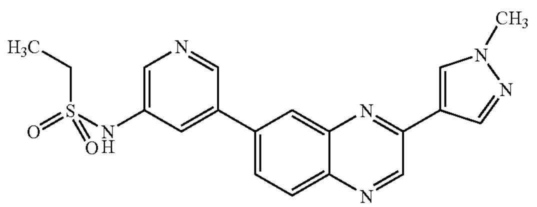 | 395 |
| 133 | 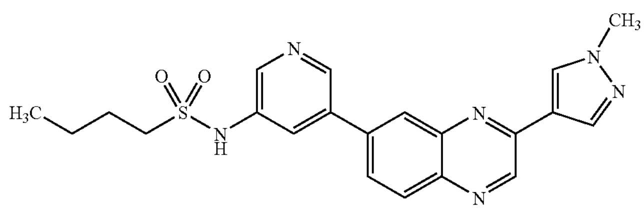 | 423 |
| 134 | 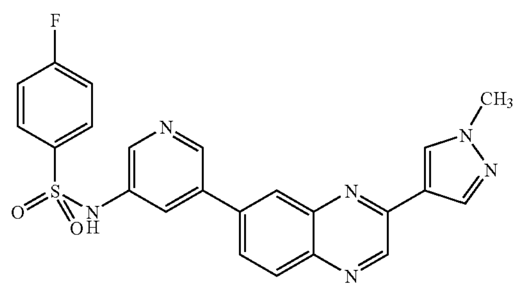 | 461 |
| 135 | 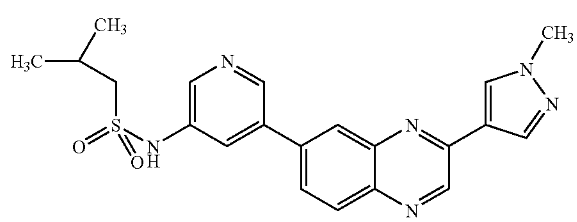 | 423 |
| 136 | 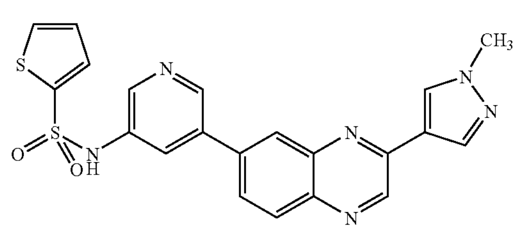 | 449 |

-continued

| Compound | Structure | MS(ES) [M + H]+ |
|---|---|---|
| 137 | 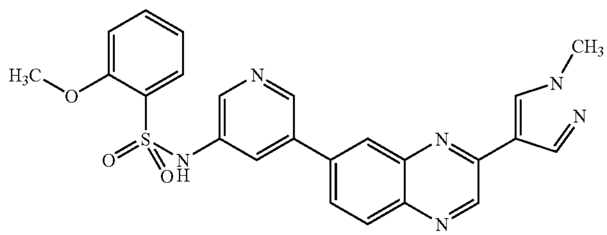 | 473 |
| 138 | 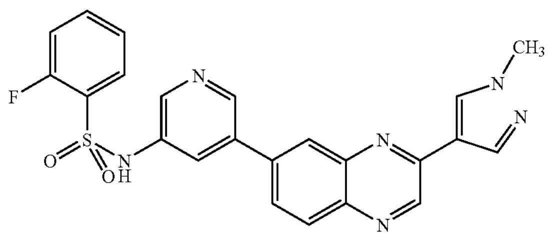 | 461 |
| 139 | 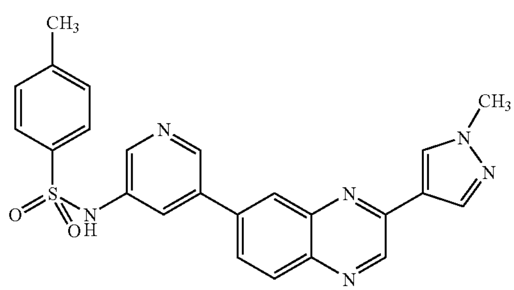 | 457 |
| 140 | 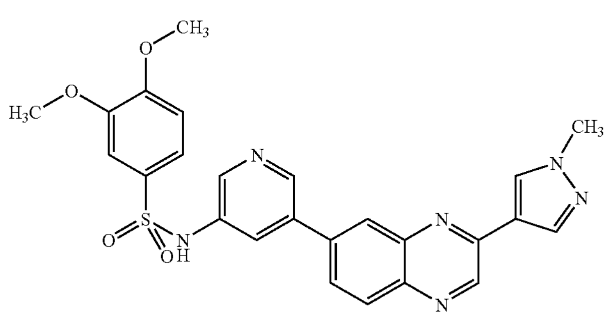 | 503 |
| 141 | 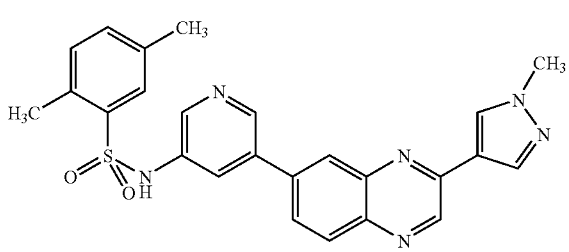 | 471 |

-continued

| Compound | Structure | MS(ES) [M + H]+ |
|---|---|---|
| 142 | 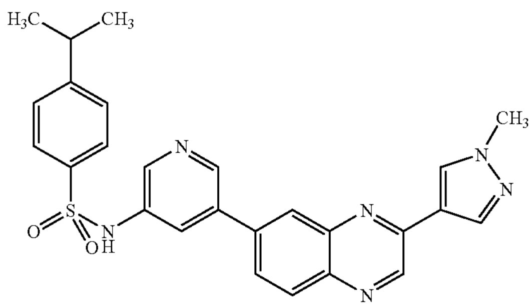 | 485 |
| 143 | 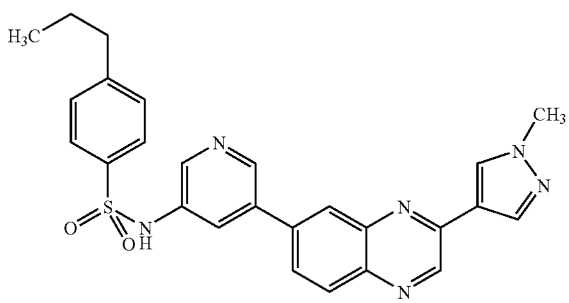 | 485 |
| 144 | 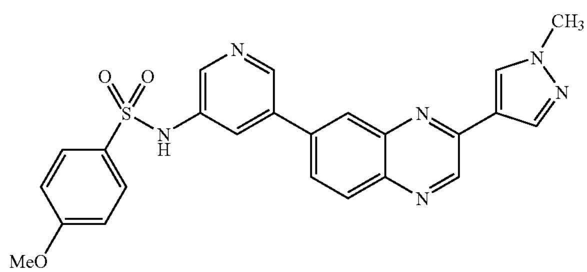 | 472 |
| 145 | 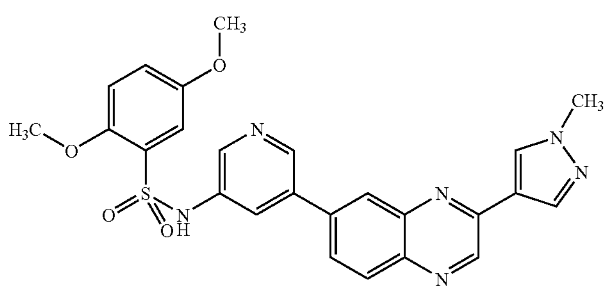 | 503 |
| 146 | 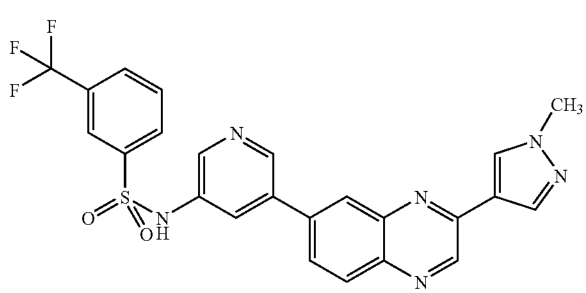 | 511 |

-continued

| Compound | Structure | MS(ES) [M + H]+ |
|---|---|---|
| 147 | 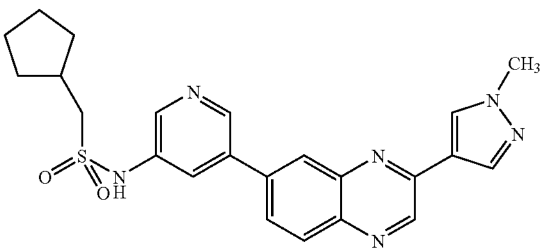 | 449 |
| 148 | 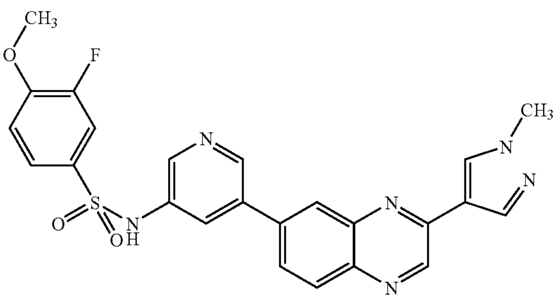 | 491 |
| 149 | 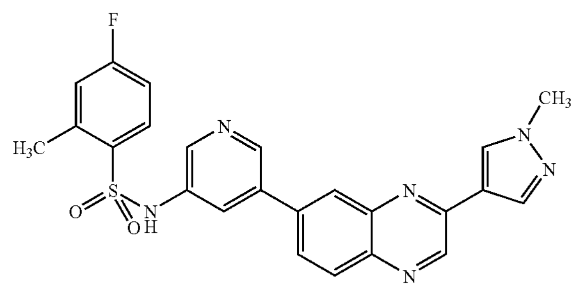 | 475 |
| 150 | 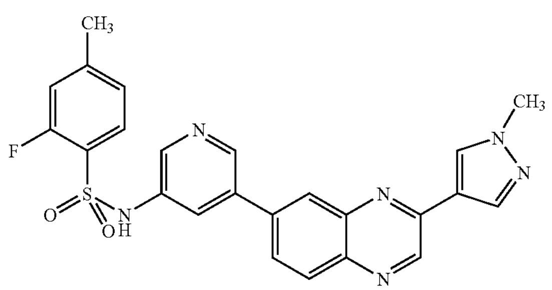 | 475 |
| 151 | 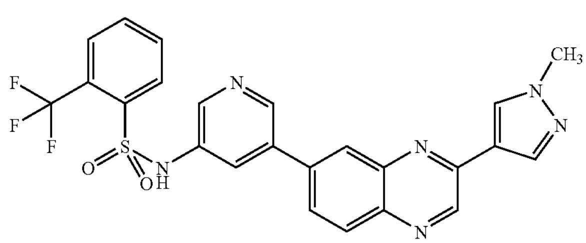 | 511 |

-continued

| Compound | Structure | MS(ES) [M + H]+ |
|---|---|---|
| 152 | 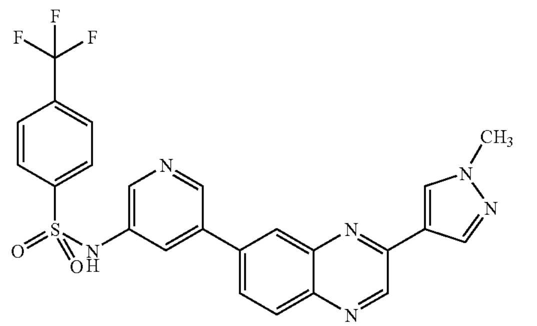 | 511 |
| 153 | 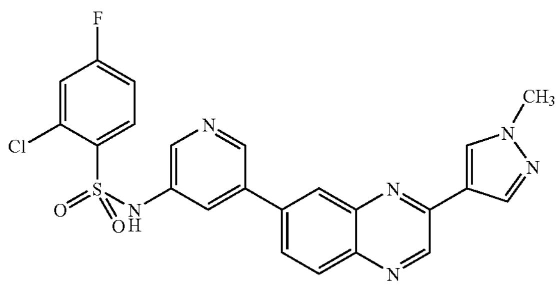 | 496 |
| 154 | 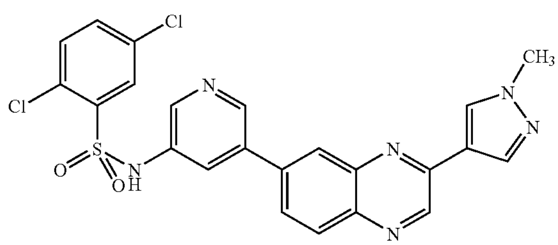 | 512 |
| 155 | 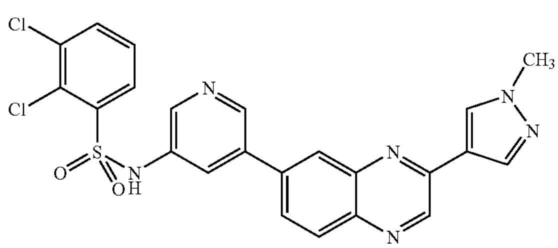 | 512 |
| 156 | 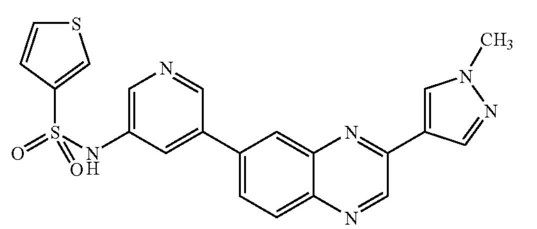 | 449 |

| Compound | Structure | MS(ES) [M + H]+ |
|---|---|---|
| 157 | 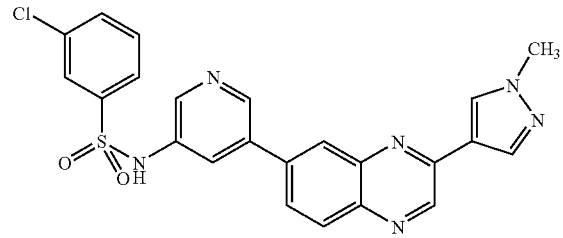 | 478 |
| 158 | 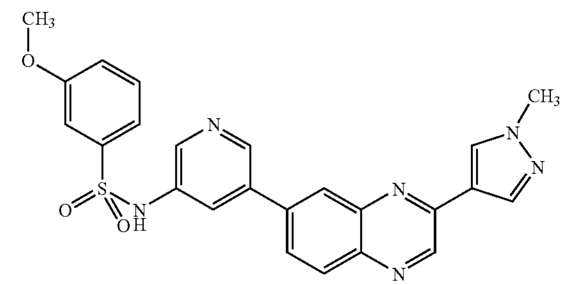 | 473 |
| 159 | 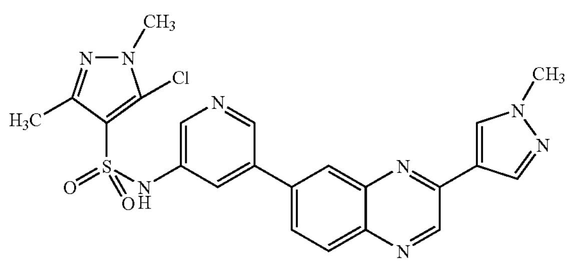 | 496 |
| 160 | 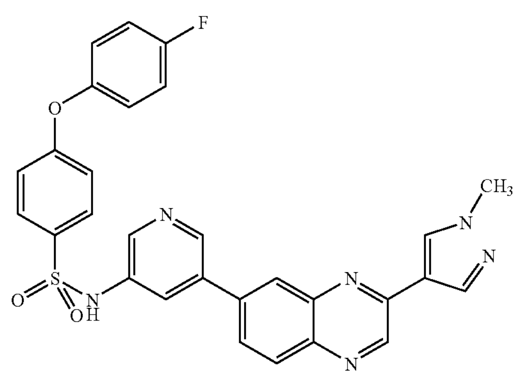 | 553 |
| 161 | 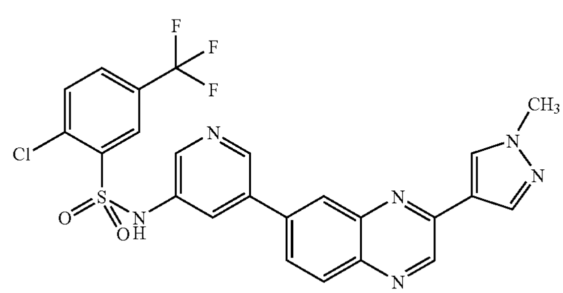 | 546 |

-continued

| Compound | Structure | MS(ES) [M + H]+ |
|---|---|---|
| 162 | 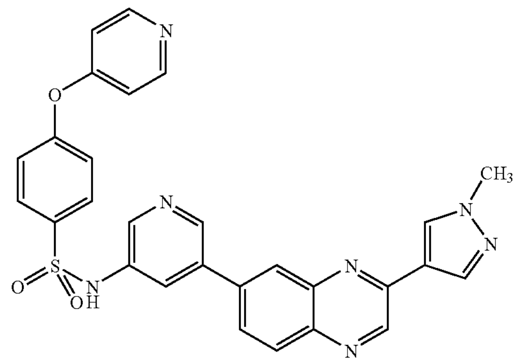 | 536 |
| 163 | 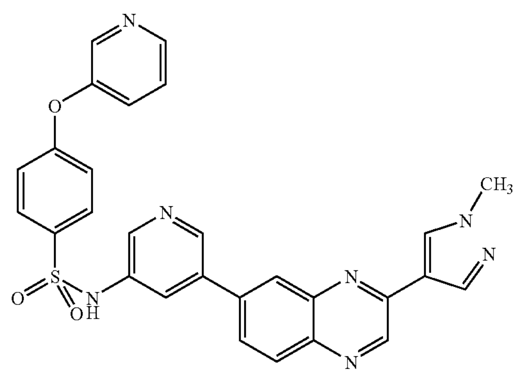 | 536 |
| 164 | 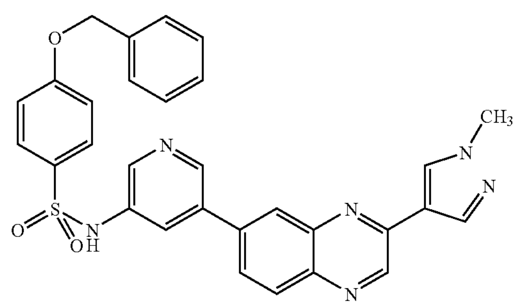 | 550 |
| 165 | 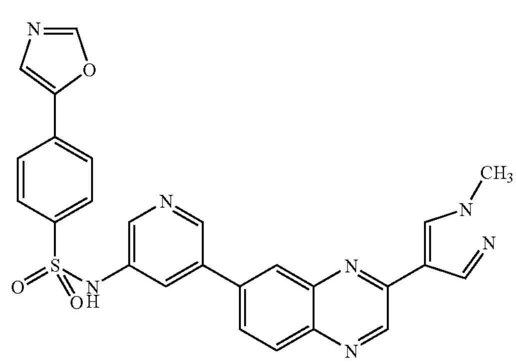 | 510 |

-continued

| Compound | Structure | MS(ES) [M + H]+ |
|---|---|---|
| 166 | 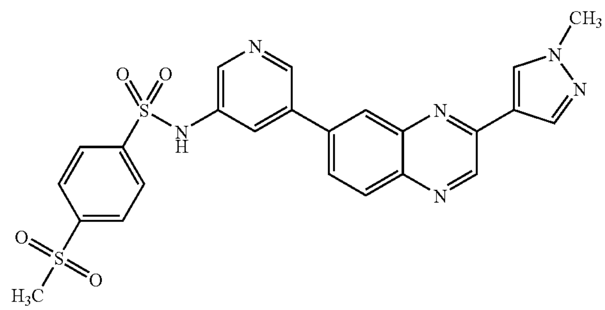 | 521 |
| 167 | 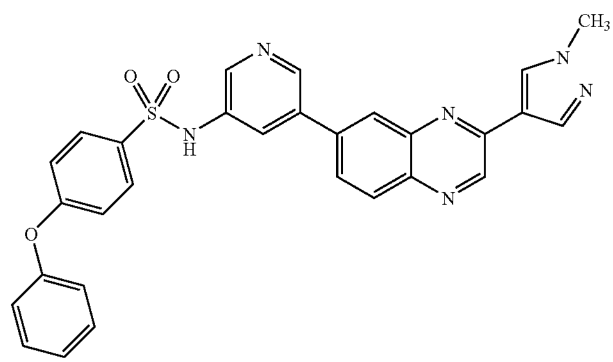 | 535 |
| 168 | 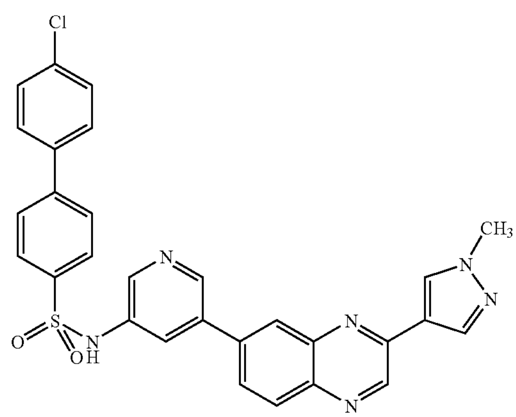 | 554 |
| 169 | 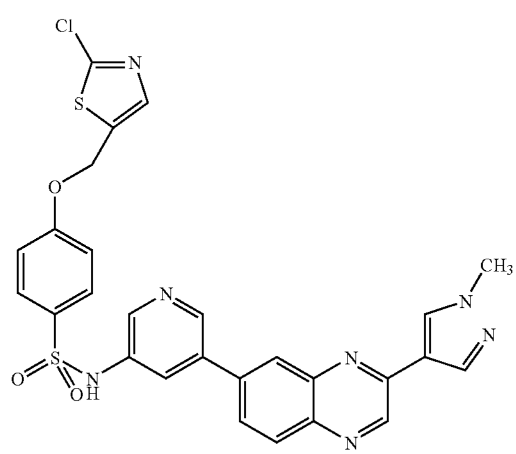 | 591 |

-continued

| Compound | Structure | MS(ES) [M + H]+ |
|---|---|---|
| 170 | 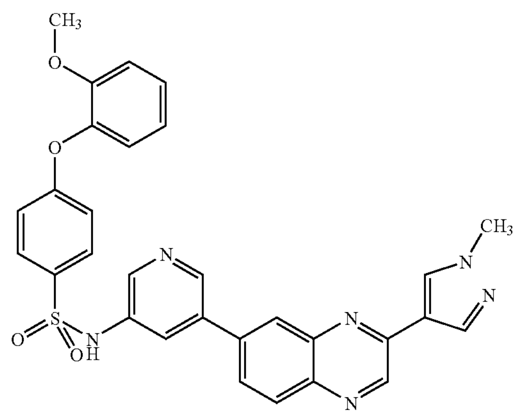 | 565 |
| 171 | 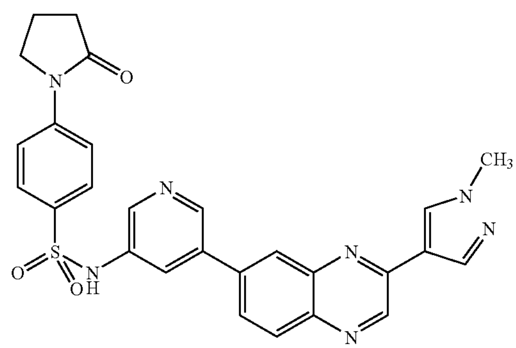 | 526 |
| 172 | 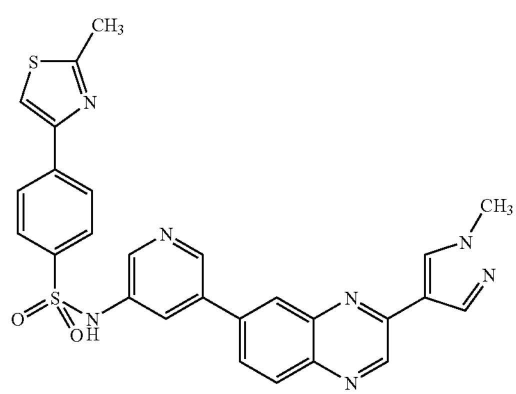 | 540 |
| 173 | 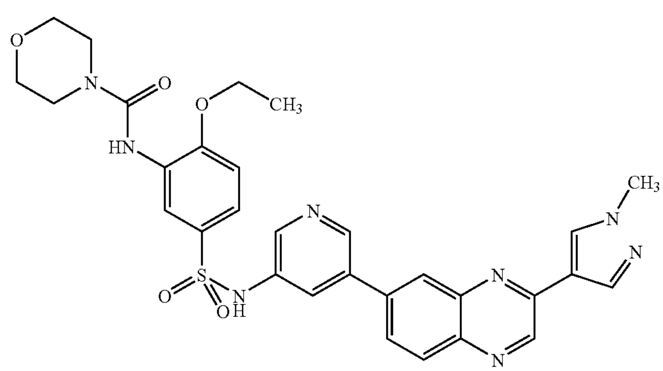 | 615 |

-continued

| Compound | Structure | MS(ES) [M + H]+ |
|---|---|---|
| 174 | 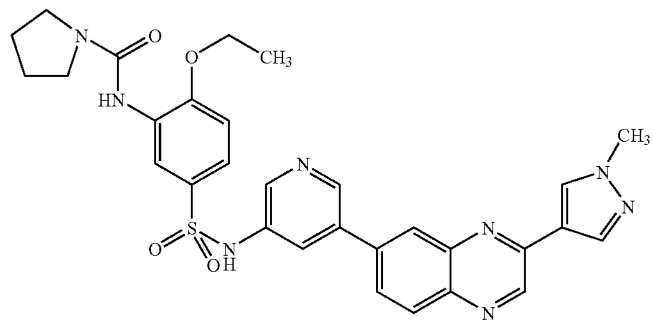 | 599 |
| 175 | 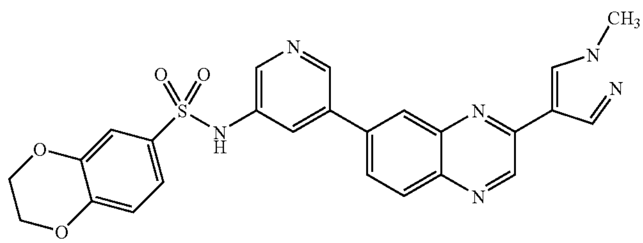 | 501 |
| 176 | 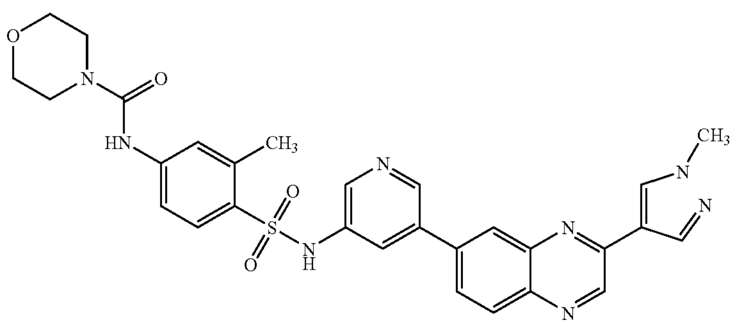 | 585 |
| 177 | 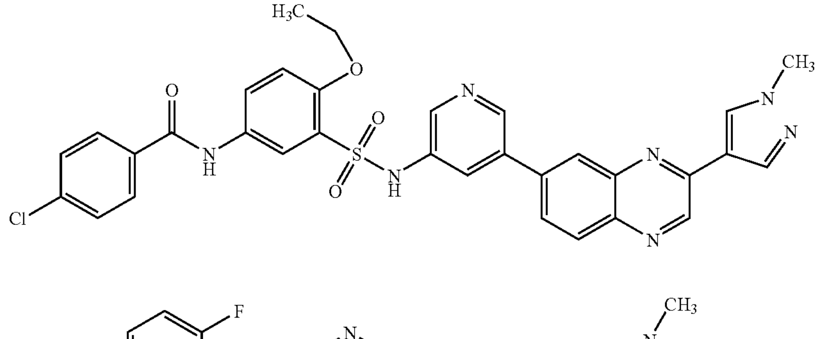 | 641 |
| 178 | 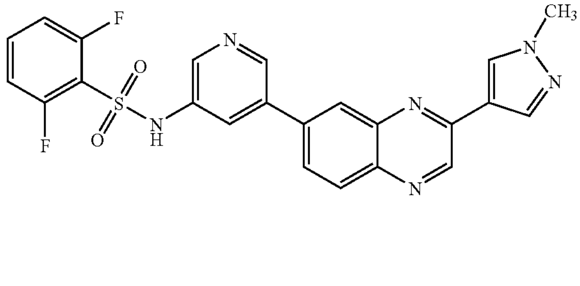 | 479 |

-continued

| Compound | Structure | MS(ES) [M + H]+ |
|---|---|---|
| 179 | 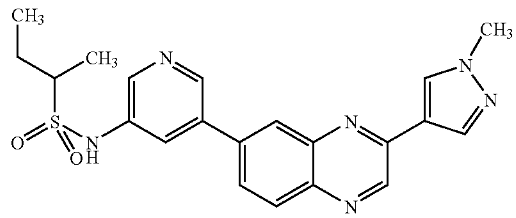 | 423 |
| 180 | 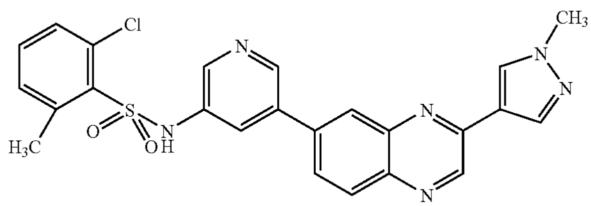 | 492 |
| 181 | 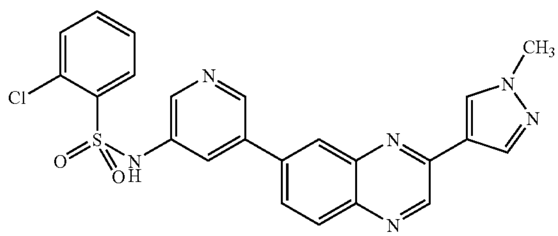 | 478 |
| 182 | 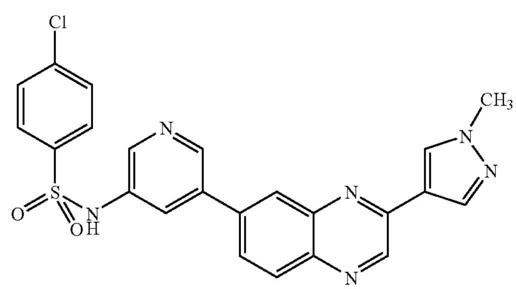 | 478 |
| 183 | 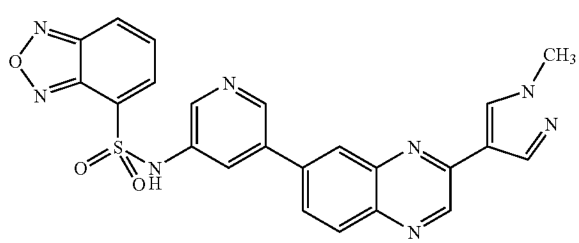 | 485 |

EXAMPLE 184

Preparation of N-{5-[3-(4-methyl-1-piperazinyl)-6-quinoxalinyl]-2-pyridinyl}acetamide

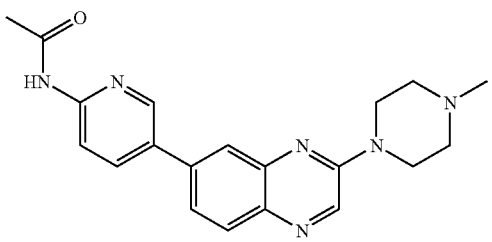

A solution of 5-[3-(4-methyl-1-piperazinyl)-6-quinoxalinyl]-2-pyridinamine (0.46 mmol) in pyridine (3 ml) was treated with a sulfonyl chloride, acyl chloride or anhydride such as acetic anhydride (0.56 mmol) and heated at 50° C. for 18 hour. The reaction mixture was treated with another portion of acetic anhydride (0.10 mmol) and stirred for another 2 days. The reaction mixture was diluted with water and saturated sodium bicarbonate (aq) and extracted with ethyl acetate. The ethyl acetate layer was dried over $Na_2SO_4$ filtered and concentrated under reduced pressure. The residue was taken into hot ethyl acetate and diluted with hexanes and cool to 0° C. The reaction mixture was filtered and washed with hexanes to give the title compound (98 mg, 58%). MS(ES)+ m/e 321 [M+H]$^+$.

The following compounds were or can be prepared following the procedures used to prepare Example 184 using the appropriate sulfonyl chloride, anhydride or acyl chloride:

| Example | Structure | MS(ES) [M + H]$^+$ |
|---|---|---|
| 185 | 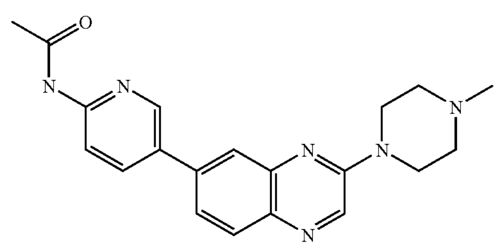 | 363 |
| 186 | 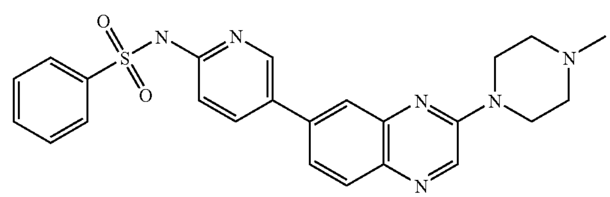 | 461 |
| 187 | 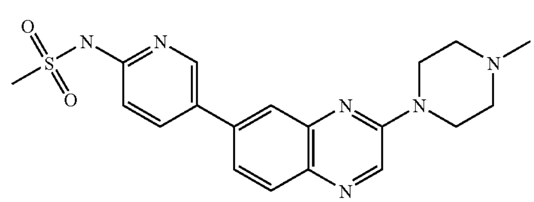 | 399 |
| 188 | 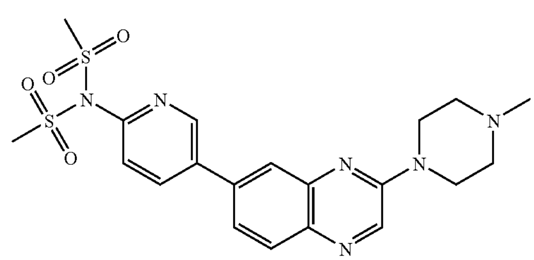 | 477 |

EXAMPLE 189

Preparation of N,N-dimethyl-N'-{5-[3-(1-methyl-1H-pyrazol-4-yl)-6-quinoxalinyl]-3-pyridinyl}sulfamide

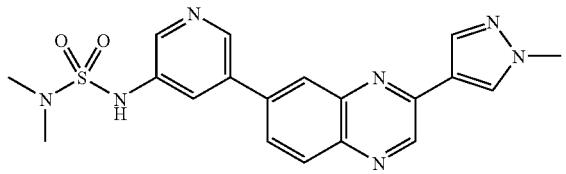

In an oven dried high pressure vessel under a nitrogen atmosphere, 7-bromo-2-(1-methyl-1H-pyrazol-4-yl)quinoxaline (150 mg, 0.519 mmol), bis(pinacolato)diboron (158 mg, 0.623 mmol), potassium acetate (153 mg, 1.556 mmol), and 1,1'-bis(diphenylphosphino)ferrocene-palladium(II) dichloride dichloromethane complex (18.98 mg, 0.026 mmol) in anhydrous 1,4-dioxane (2 mL) was stirred at 100° C. in an oil bath for 1 hr. The reaction mixture was cooled to room temperature. N'-(5-bromo-3-pyridinyl)-N,N-dimethylsulfamide (145 mg, 0.519 mmol) followed by sodium bicarbonate (131 mg, 1.556 mmol) in water (0.67 mL) were added to the reaction mixture and the vessel was sealed again. The reaction was stirred at 100° C. for 16.75 hours then cooled to room temperature. The reaction was filtered through Celite and the pad was washed with ethyl acetate. The bi-phasic mixture was separated in a separatory funnel. The organic layer was washed with brine (20 mL), dried over magnesium sulfate, and concentrated in vacuo to give a brown solid. Trituration of the brown solid in dichloromethane (3 drops) and ether (8 mL) provided the title compound (120 mg, 57%) as a light brown solid. MS(ES)+ m/e 410.2 [M+H]+.

EXAMPLE 190

Preparation of N-{5-[3-(1-methyl-1H-pyrazol-4-yl)-6-quinoxalinyl]-3-pyridinyl}-4-morpholinesulfonamide

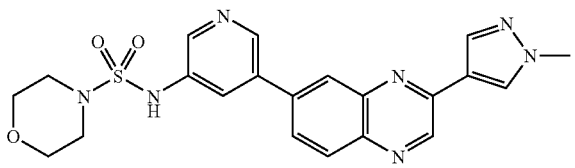

In an oven-dried flask under nitrogen, a solution of 5-[3-(1-methyl-1H-pyrazol-4-yl)-6-quinoxalinyl]-3-pyridinamine (99 mg, 0.327 mmol) in pyridine (3 mL) at room temperature was treated with morpholine-4-sulfonyl chloride (96 mg, 0.491 mmol) by syringe. The reaction was stirred at room temperature for 16.5 hours. The reaction was very sluggish so the reaction was placed in an oil bath at 50° C. and stirred at that temperature for 23 hours. The reaction was progressing to the desired product as determined by LCMS but was not yet complete. The reaction mixture was stirred for an additional 4 days at 50° C. The reaction did not progress to completion. The reaction was cooled to room temperature and concentrated in vacuo. The residue was taken up into 200 mL ethyl acetate and 50 mL water. The organic layer was washed with saturated aqueous sodium bicarbonate solution (100 mL) followed by brine (100 mL), dried over magnesium sulfate and concentrated in vacuo. Purification by silica gel chromatography eluting with 0-10% methanol in dichloromethane provided the desired product as a residue which was not pure. Addition of dichloromethane/ether resulted in precipitate formation. The precipitate was collected by filtration. Recrystallization of the precipitate from ethanol provided the title compound (26 mg, 18%) as a rust-coloured solid. MS(ES)+ m/e 452.0 [M+H]+.

Related sulfamide analogs can be prepared in a similar manner using the appropriate sulfamoyl chloride.

EXAMPLE 191

Preparation of 2-phenyl-N-(7-{5-[(phenylsulfonyl)amino]-3-pyridinyl}-2-quinoxalinyl)acetamide

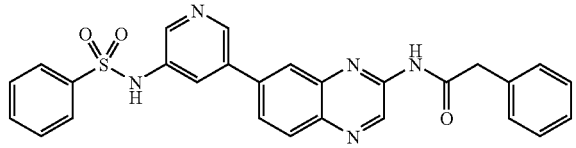

a) N-(7-bromo-2-quinoxalinyl)-2-phenylacetamide

A slurry of 7-bromo-2-chloroquinoxaline (0.493 mmol), 2-phenylacetamide (0.518 mmol), cesium carbonate (0.739 mmol), (9,9-dimethyl-9H-xanthene-4,5-diyl)bis(diphenylphosphane) (XantPhos, 0.029 mmol), and palladium(II) acetate (0.018 mmol) in 1,4-dioxane (3 mL) was heated at 100° C. for 18 h. The reaction mixture was cooled, poured into water (50 mL) and brine (20 mL), and extracted with ethyl acetate (3×50 mL). The combined organic layers were dried over sodium sulfate, filtered, and concentrated in vacuo. Purification of the residue by silica gel chromatography (10-30% ethyl acetate/hexanes) provided the title compound as a yellow solid (90 mg, 51%). MS(ES)+ m/e 342, 344 [M+H]+.

b) 2-phenyl-N-(7-{5-[(phenylsulfonyl)amino]-3-pyridinyl}-2-quinoxalinyl)acetamide A mixture of N-(7-bromo-2-quinoxalinyl)-2-phenylacetamide (0.254 mmol), N-[5-(4,4,5,5-tetramethyl-1,3,2-dioxaborolan-2-yl)-3-pyridinyl]benzenesulfonamide (0.508 mmol), and [1,1'-bis(diphenylphosphino)ferrocene]dichloropalladium(II) dichloromethane complex (1:1) (0.007 mmol) in 2M aqueous sodium carbonate (0.5 mL) and 1,4-dioxane (2 mL) was heated at 100° C. for 5 h. The reaction mixture was cooled, poured into water (60 mL) and brine (15 mL), and extracted with ethyl acetate (50 mL). The aqueous layer was acidified with 1N aqueous HCl until the pH was approximately 6-7 and then further extracted with (3×50 mL) ethyl acetate. The combined organic layers were dried over sodium sulfate, filtered, and concentrated in vacuo. Purification of the residue by silica gel chromatography eluting with 50-70% ethyl acetate/hexanes followed by reverse phase HPLC (30-75% acetonitrile/water with 0.1% TFA) afforded the title product as a tan solid (42 mg, 33%). MS(ES)+ m/e 496 [M+H]+.

The following compounds were or can be prepared in a similar manner to the compound of Example 191 using the appropriate amide or sulfonamide:

| Example | Structure | MS(ES) [M + H]+ |
|---|---|---|
| 192 | 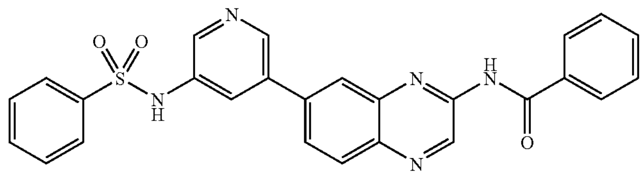 | 482 |
| 193 | 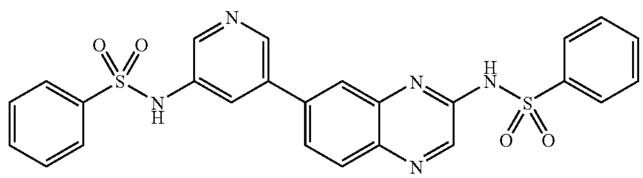 | 518 |

EXAMPLE 194

Preparation of 1,1-dimethylethyl [2-(4-{7-[5-(aminosulfonyl)-3-pyridinyl]-2-quinoxalinyl}-1-piperazinyl)ethyl]carbamate

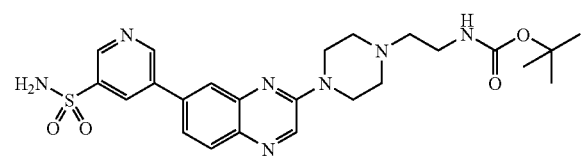

a) 1,1-dimethylethyl {2-[4-(7-bromo-2-quinoxalinyl)-1-piperazinyl]ethyl}carbamate A solution of 7-bromo-2-chloroquinoxaline (1.20 mmol) in N,N-dimethylformamide (5 ml) was treated with an amine (or an alcohol) such as 1,1-dimethylethyl [2-(1-piperazinyl)ethyl]carbamate (3.60 mmol) then heated at 80° C. for 1 hour. The reaction was cooled to ambient temperature then poured into water (25 ml). Product precipitated out of solution, which was filtered and dried. Alternatively, after the reaction is cooled to ambient temperature and poured into water (25 ml), it was extracted into ethyl acetate (3×25 ml). The extracts were washed with brine then dried over anhydrous sodium sulfate, filtered and concentrated under reduced pressure to give the title compound (520 mg, 80%) as a yellow solid. MS(ES)+ m/e 297.2 [M+]+.

b) 1,1-dimethylethyl [2-(4-{7-[5-(aminosulfonyl)-3-pyridinyl]-2-quinoxalinyl}-1-piperazinyl)ethyl]carbamate A slurry of 1,1-dimethylethyl {2-[4-(7-bromo-2-quinoxalinyl)-1-piperazinyl]ethyl}carbamate (0.96 mmol), bis(pinacolato)diboron (1.06 mmol), potassium acetate (3.84 mmol), and [1,1'-bis(diphenylphosphino)ferrocene]dichloropalladium(II) dichloromethane complex (1:1) (0.07 mmol) in 1,4-dioxane (5 ml) was heated at 100° C. After the reaction stirred for 1 hour, 5-bromo-3-pyridinesulfonamide (0.96 mmol) and 2M potassium carbonate (aq) (4 ml) was added and the reaction mixture stirred for 18 hours. The reaction was cooled to ambient temperature, separated the organic layer and purified directly on silica by column chromatography (10% ethyl acetate/hexanes). The desired fractions were combined and concentrated to give the title compound (20 mg, 7%) as a light yellow solid. MS(ES)+ m/e 514.2 [M+H]+.

The following compounds were or can be prepared following the procedures in Example 195 using the appropriate amine (or alcohol):

| Example | Structure | MS(ES) [M + H]+ |
|---|---|---|
| 196 | 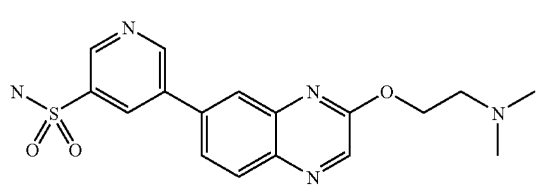 | 374 |
| 197 | 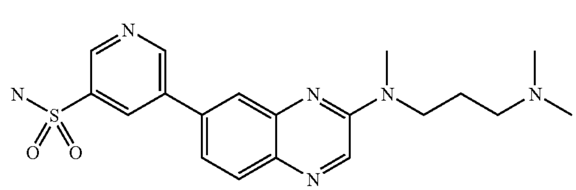 | 402 |

-continued
| Example | Structure | MS(ES) [M + H]+ |
|---------|-----------|-----------------|
| 198 | 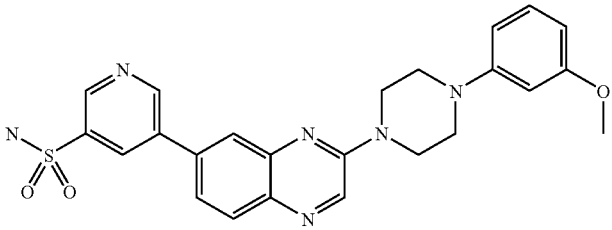 | 477 |
| 199 | 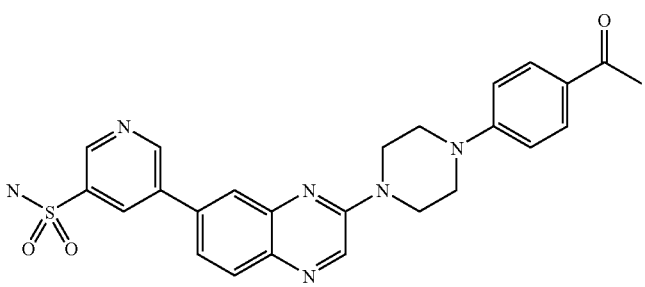 | 489 |
| 200 | 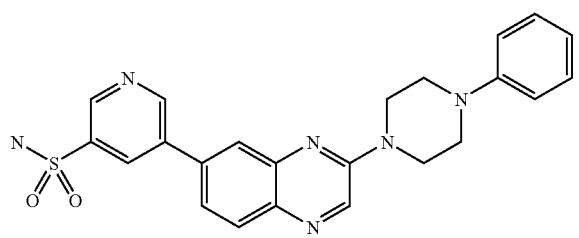 | 447 |
| 201 | 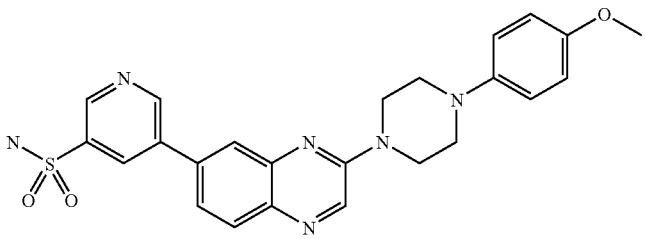 | 462 |
| 202 | 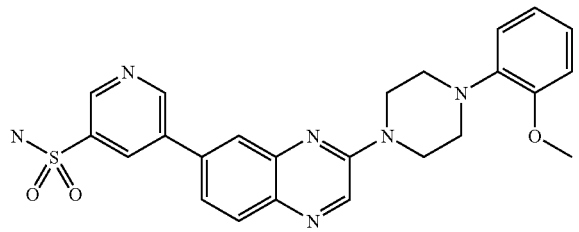 | 477 |
| 203 | 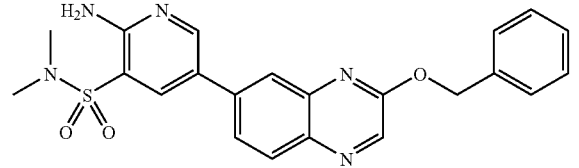 | 436 |

EXAMPLE 204

Preparation of N-(2,4-difluorophenyl)-5-{3-[4-(dimethylamino)-1-piperidinyl]-6-quinoxalinyl}-3-pyridinesulfonamide

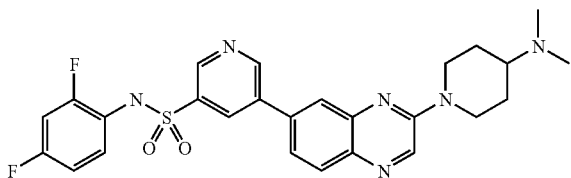

a) 1-(7-bromo-2-quinoxalinyl)-N,N-dimethyl-4-piperidinamine

A solution of 7-bromo-2-chloroquinoxaline (1.20 mmol) in N,N-dimethylformamide (5 ml) was treated with an amine (or an alcohol) such as 1,1-dimethylethyl [2-(1-piperazinyl)ethyl]carbamate (3.60 mmol) then heated at 80° C. for 1 hour. The reaction was cooled to ambient temperature then poured into water (25 ml). Product precipitated out of solution, which was filtered and dried. Alternatively, after the reaction is cooled to ambient temperature and poured into water (25 ml), it was extracted into ethyl acetate (3×25 ml). The extracts were washed with brine then dried over anhydrous sodium sulfate, filtered and concentrated under reduced pressure to give the title compound (400 mg, 99%) as a yellow solid. MS(ES)+ m/e 336.2 [M+]+.

b) N-(2,4-difluorophenyl)-5-{3-[4-(dimethylamino)-1-piperidinyl]-6-quinoxalinyl}-3-pyridinesulfonamide A slurry of 1-(7-bromo-2-quinoxalinyl)-N,N-dimethyl-4-piperidinamine (1.2 mmol), bis(pinacolato)diboron (1.30 mmol), potassium acetate (4.80 mmol), and [1,1'-bis(diphenylphosphino)ferrocene]dichloropalladium(II) dichloromethane complex (1:1) (0.09 mmol) in 1,4-dioxane (5 ml) was heated at 100° C. After the reaction stirred for 2.5 hours, 5-bromo-3-pyridinesulfonamide (0.96 mmol) and 2M solution potassium carbonate (5 ml) was added and continued to stir for 18 hours. The reaction was cooled to ambient temperature, separated the organic layer and purified directly on silica by column chromatography (5%, 5% ammonium hydroxide/methanol:ethyl acetate). The desired fractions were combined and concentrated to give the title compound (20 mg, 3%) as a tan solid. MS(ES)+ m/e 525.2 [M+H]+.

The following compounds were or can be prepared following the procedures in Example 204 using the appropriate amine or phenol. In some cases, pretreatment of the amine with sodium hydride (3 equivalents) was required:

| Example | Structure | MS(ES) [M + H]+ |
|---|---|---|
| 205 | 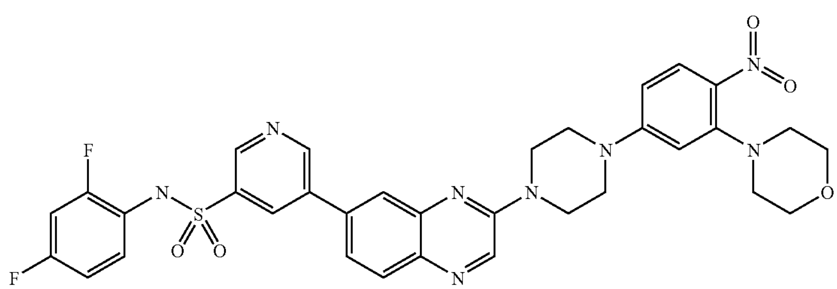 | 689 |
| 206 | 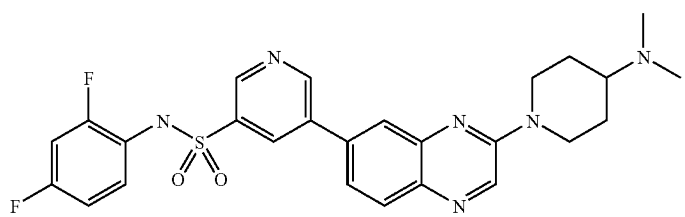 | 525.2 |
| 207 | 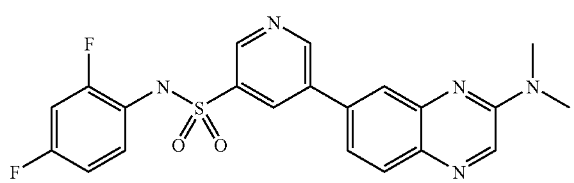 | 442 |
| 208 | 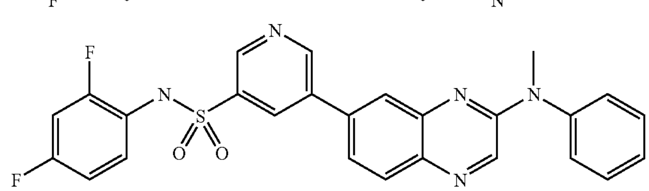 | 504 |

-continued

| Example | Structure | MS(ES) [M + H]+ |
|---|---|---|
| 209 | 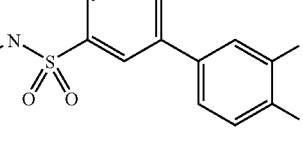 | 491 |
| 210 | 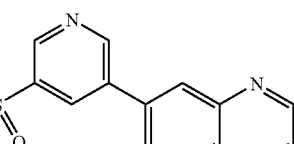 | 577 |
| 211 | 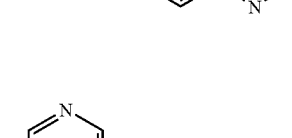 | 574 |
| 212 | 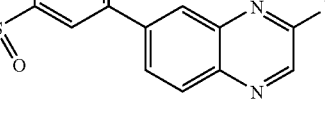 | 574 |

EXAMPLE 213

Preparation of N-(2-chloro-5-{3-[3-(dimethylamino)-1-piperidinyl]-6-quinoxalinyl}-3-pyridinyl)benzenesulfonamide

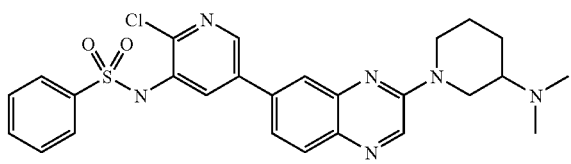

a) 1-(7-bromo-2-quinoxalinyl)-N,N-dimethyl-3-piperidinamine

A solution of 7-bromo-2-chloroquinoxaline (1.20 mmol) in N,N-dimethylformamide (5 ml) was treated with an amine (or an alcohol) such as N,N-dimethyl-3-piperidinamine dihydrochloride (3.60 mmol) and triethylamine (7.20 mmol) then heated at 100° C. for 1 hour. The reaction was cooled to ambient temperature then poured into water (25 ml). Product precipitated out of solution, which was filtered and dried. Alternatively, after the reaction is cooled to ambient temperature and poured into water (25 ml), it was extracted into ethyl acetate (3×25 ml). The extracts were washed with brine then dried over anhydrous sodium sulfate, filtered and concentrated under reduced pressure to give the title compound (400 mg, 99%) as an orange solid. MS(ES)+ m/e 336.2 [M+]+.

b) Preparation of N-(2-chloro-5-{3-[3-(dimethylamino)-1-piperidinyl]-6-quinoxalinyl}-3-pyridinyl)benzenesulfonamide A slurry of 1-(7-bromo-2-quinoxalinyl)-N,N-dimethyl-3-piperidinamine (1.2 mmol), bis(pinacolato)diboron (1.30 mmol), potassium acetate (4.80 mmol), and [1,1'-bis(diphenylphosphino)ferrocene]dichloropalladium(II) dichloromethane complex (1:1) (0.09 mmol) in 1,4-dioxane (5 ml) was heated at 100° C. After the reaction stirred for 2.5 hours, N-(5-bromo-2-chloro-3-pyridinyl)benzenesulfonamide (1.20 mmol) and 2M solution potassium carbonate (5 ml) was added and continued to stir for 18 hours. The reaction was cooled to ambient temperature, concentrated, redissolved in methanol and purified on reverse phase HPLC (0.1% trifluoracetic acid/water in acetonitrile). The desired fractions were combined, neutralized with saturated sodium bicarbonate, extracted with ethyl acetate (3×20 ml). Combined organic layers were washed with brine, dried over sodium sulfate, filtered and concentrated to give the title compound (52 mg, 10%) as a yellow solid. MS(ES)+ m/e 524.2 [M+H]+.

The following compounds were or can be prepared following the procedures in Example 213 using the appropriate amine:

| Example | Structure | MS(ES) [M + H]+ |
|---|---|---|
| 214 | 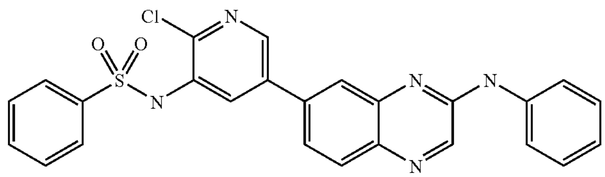 | 488 |
| 215 | 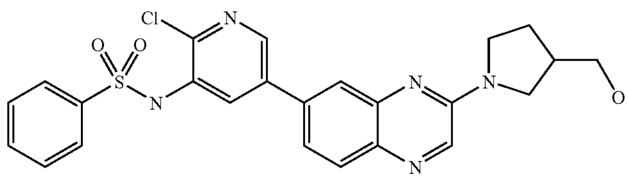 | 496 |
| 216 | 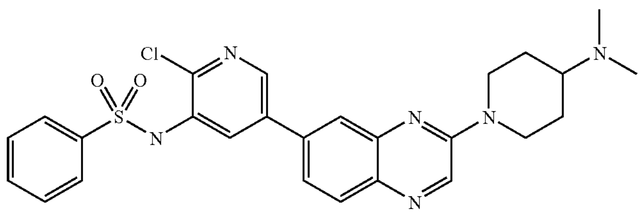 | 524 |
| 217 | 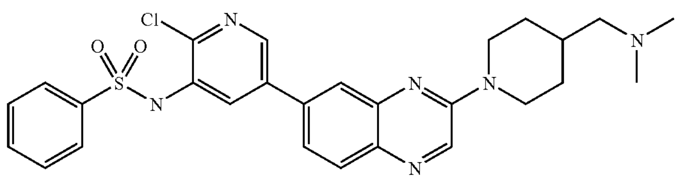 | 538 |
| 218 | 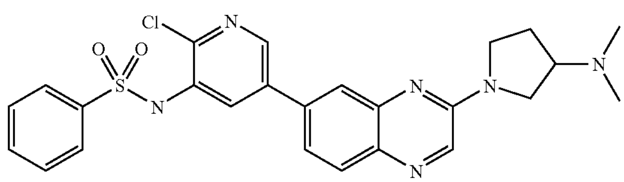 | 510 |
| 219 | 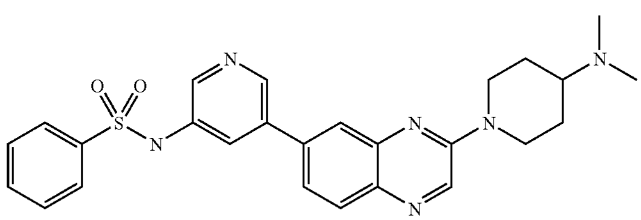 | 489 |
| 220 | 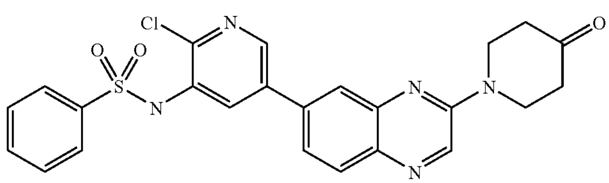 | 494 |
| 221 | 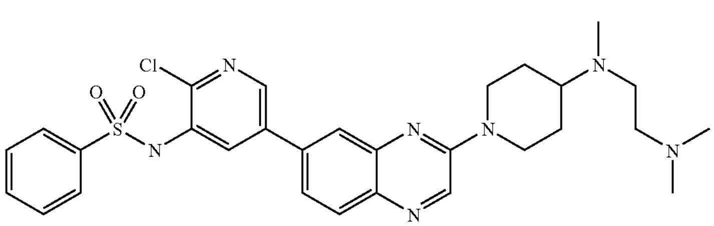 | 581 |

-continued

| Example | Structure | MS(ES) [M + H]+ |
|---|---|---|
| 222 | 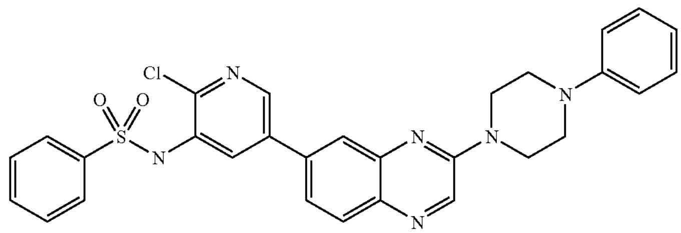 | 558 |
| 223 | 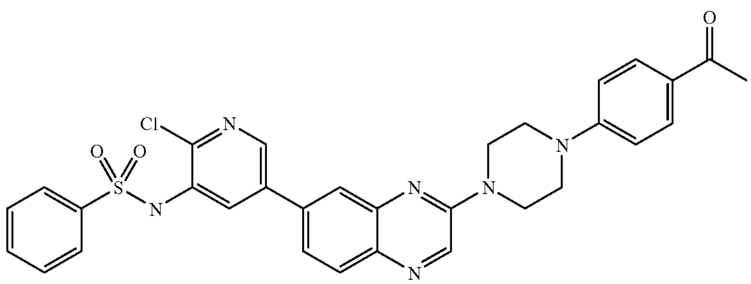 | 600 |
| 224 | 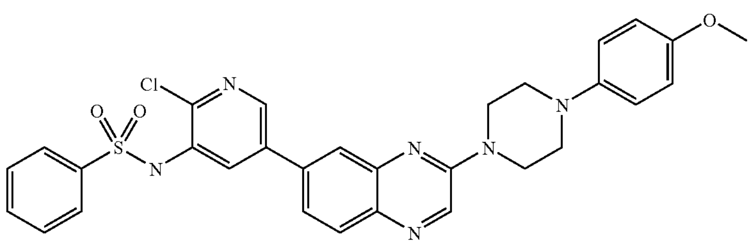 | 589 |
| 225 | 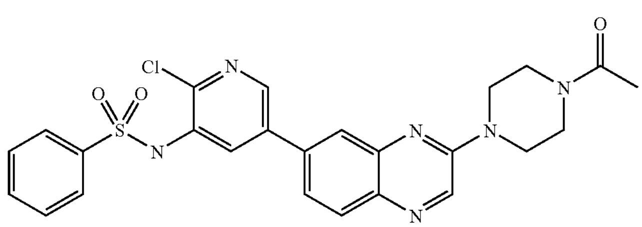 | 424 |
| 226 | 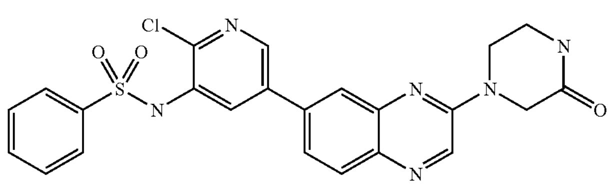 | 495 |
| 227 | 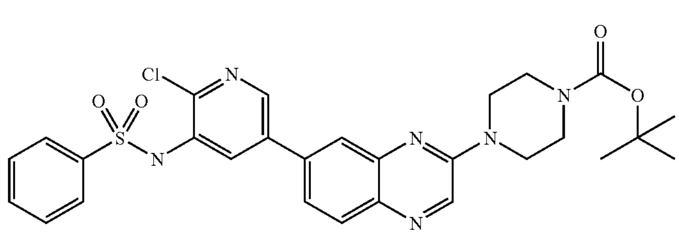 | 582 |

| Example | Structure | MS(ES) [M + H]+ |
|---|---|---|
| 228 | 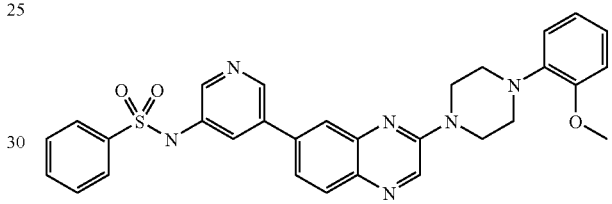 | 651 |

EXAMPLE 229

Preparation of N-{2-chloro-5-[3-(1-piperazinyl)-6-quinoxalinyl]-3-pyridinyl}benzenesulfonamide

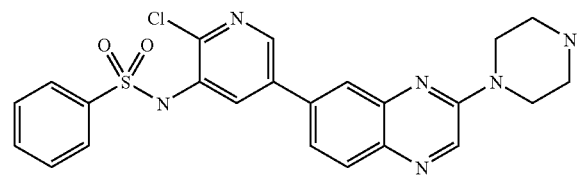

To a solution of 1,1-dimethylethyl 4-(7-{6-chloro-5-[(phenylsulfonyl)amino]-3-pyridinyl}-2-quinoxalinyl)-1-piperazinecarboxylate (0.83 mmol) in acetonitrile (6 ml) was added concentrated trifluoroacetic acid (3 ml). The reaction stirred at ambient temperature for 3 hours and was then concentrated to an orange oil. The residue was neutralized with saturated sodium bicarbonate solution upon which a precipitate was formed. The product was filtered and dried to give the title compound (260 mg, 65%) as an off-white solid. MS(ES)+ m/e 481.2 [M+H]+.

EXAMPLE 230

Preparation of N-(2-chloro-5-{3-[4-(methylsulfonyl)-1-piperazinyl]-6-quinoxalinyl}-3-pyridinyl)benzenesulfonamide

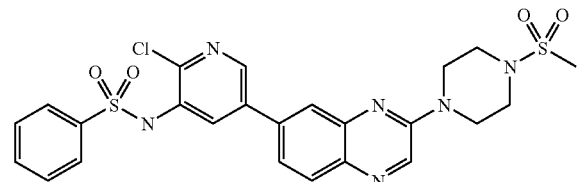

To a solution of N-{2-chloro-5-[3-(1-piperazinyl)-6-quinoxalinyl]-3-pyridinyl}benzenesulfonamide (0.23 mmol), triethylamine (0.92 mmol), in dichloromethane (5 ml) was added methanesulfonyl chloride (0.25 mmol), which stirred at 50° C. for 18 hours. The reaction was cooled to ambient temperature, concentrated, redissolved in methanol and purified on reverse phase HPLC (0.1% ammonium hydroxide/water in acetonitrile). The desired fractions were combined and concentrated to give the title compound (7.8 mg, 2%) as a white solid. MS(ES)+ m/e 560.2 [M+H]+.

EXAMPLE 231

Preparation of N-[5-(3-{4-[2-(methyloxy)phenyl]-1-piperazinyl}-6-quinoxalinyl)-3-pyridinyl]benzenesulfonamide a) 7-bromo-2-{4-[2-(methyloxy)phenyl]-1-piperazinyl}quinoxaline A solution of 7-bromo-2-chloroquinoxaline (1.20 mmol) in N,N-dimethylformamide (15 ml) was treated with an amine (or an alcohol) such as 1-[2-(methyloxy)phenyl]piperazine (3.60 mmol) and then heated at 100° C. for 1 hour. The reaction was cooled to ambient temperature then poured into water (25 ml) and extracted into ethyl acetate (3×25 ml). The extracts were washed with brine then dried over anhydrous sodium sulfate, filtered, concentrated and the residue crystallized with ethyl acetate:hexanes to give the title compound (331 mg, 70%) as yellow crystals. MS(ES)+ m/e 398.2 [M+]+.

b) N-[5-(3-{4-[2-(methyloxy)phenyl]-1-piperazinyl}-6-quinoxalinyl)-3-pyridinyl]benzenesulfonamide A slurry of a boronate ester such as N-[5-(4,4,5,5-tetramethyl-1,3,2-dioxaborolan-2-yl)-3-pyridinyl]benzenesulfonamide (0.55 mmol), 7-bromo-2-{4-[2-(methyloxy)phenyl]-1-piperazinyl}quinoxaline (0.37 mmol), and [1,1'-bis(diphenylphosphino)ferrocene]dichloropalladium(II) dichloromethane complex (1:1) (0.03 mmol) in 1,4-dioxane (4 ml) and 2M potassium carbonate (aq) (2 ml) was stirred at 100° C. for 18 hours. The reaction was cooled to ambient temperature, the organic layer separated and purified directly on silica by column chromatography (80% ethyl acetate/hexanes). The desired fractions were combined and concentrated to give the title compound (99 mg, 48%) as a yellow solid. MS(ES)+ m/e 553.4 [M+H]+.

The following compounds were or can be prepared following the procedures in Example 231 using the appropriate amine:

| Example | Structure | MS(ES) [M + H]+ |
|---|---|---|
| 232 | 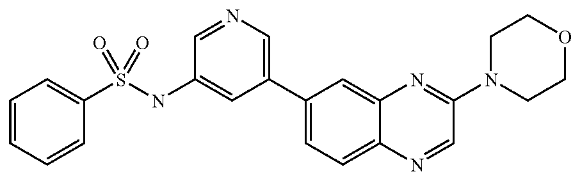 | 448 |
| 233 | 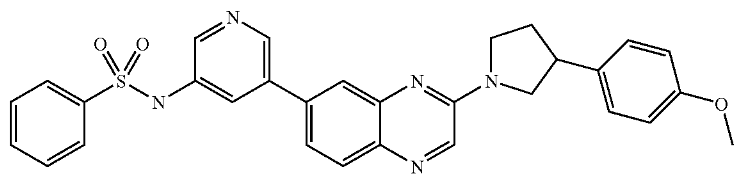 | 538 |
| 234 | 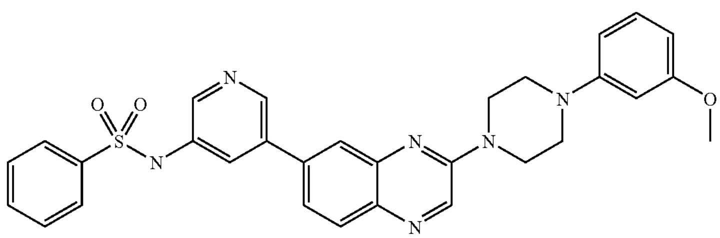 | 553 |
| 235 | 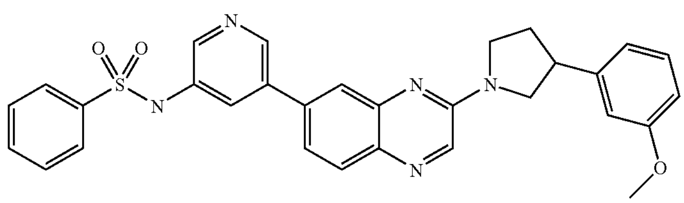 | 538 |
| 236 | 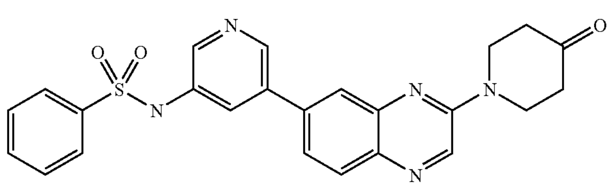 | 460 |
| 237 | 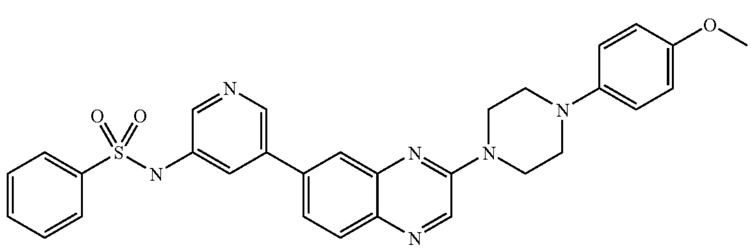 | 553 |
| 238 | 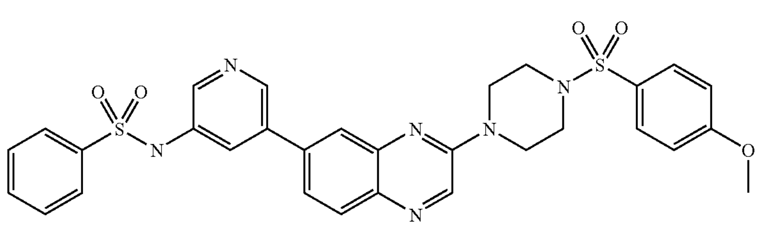 | 617 |

-continued

| Example | Structure | MS(ES) [M + H]+ |
|---|---|---|
| 239 | 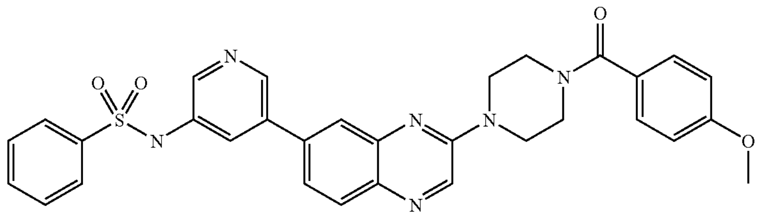 | 581 |
| 240 | 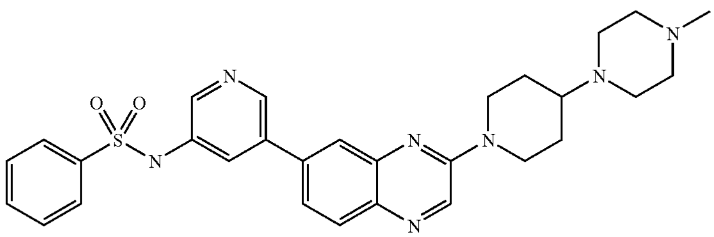 | 544 |
| 241 | 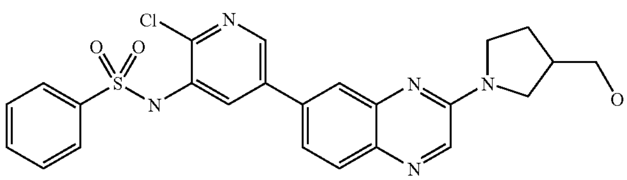 | 496 |
| 242 | 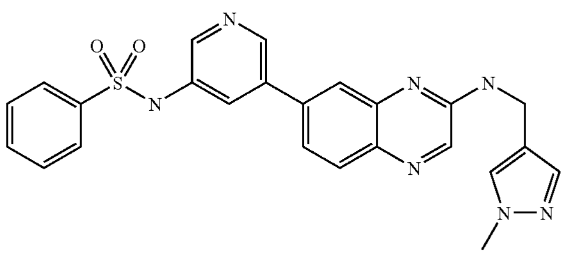 | 525 |
| 243 | 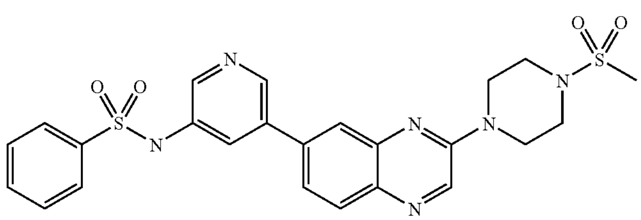 | 567 |
| 244 | 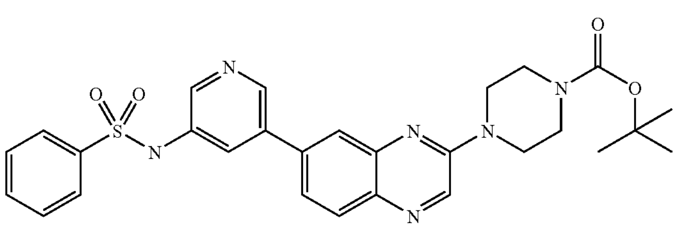 | 547 |
| 245 | 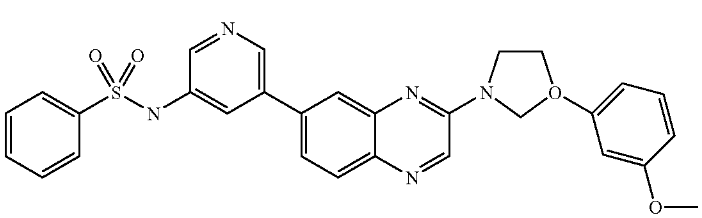 | 538 |

-continued

| Example | Structure | MS(ES) [M + H]+ |
|---|---|---|
| 246 | 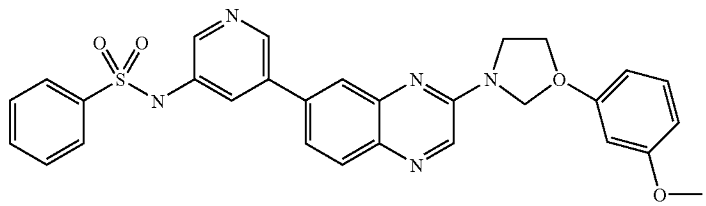 | 538 |
| 247 | 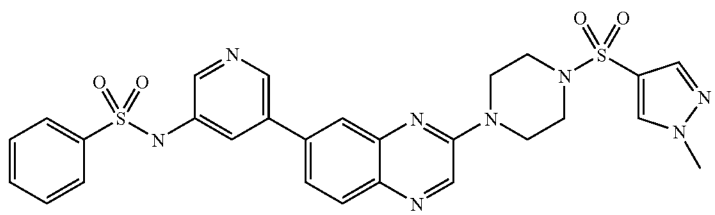 | 591 |
| 248 | 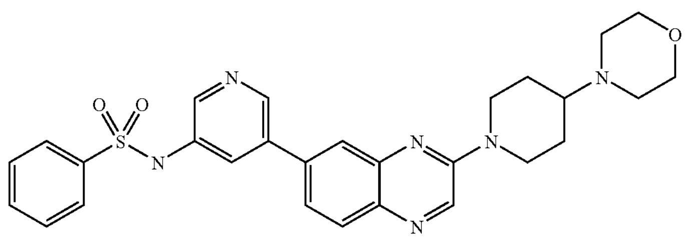 | 531 |
| 249 | 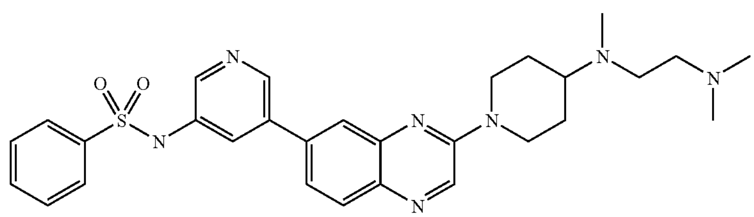 | 546 |
| 250 | 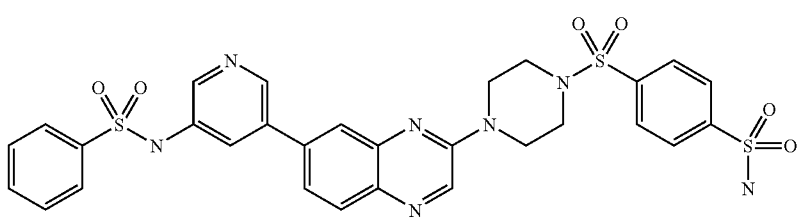 | 665 |
| 251 | 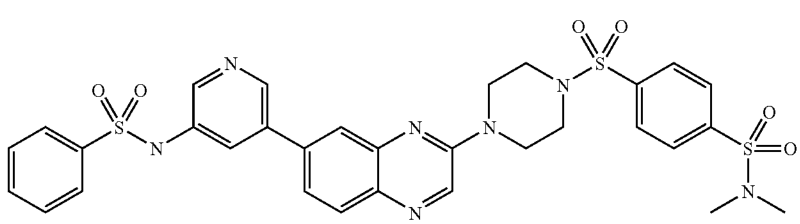 | 694 |
| 252 | 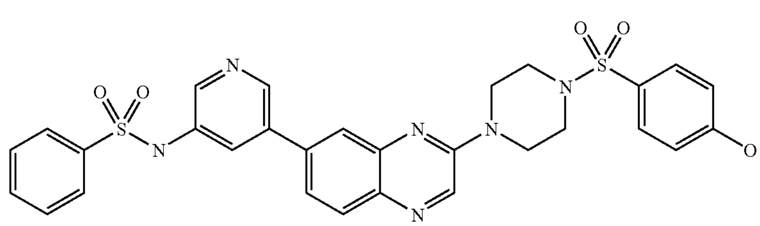 | 603 |

-continued

| Example | Structure | MS(ES) [M + H]+ |
|---|---|---|
| 253 | 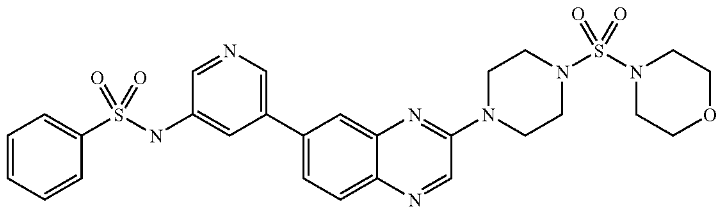 | 596 |
| 254 | 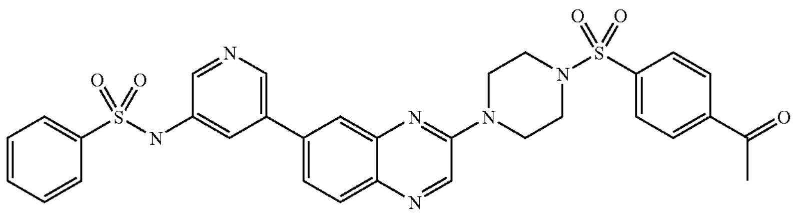 | 629 |
| 255 | 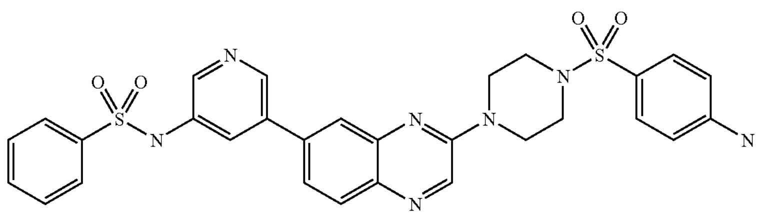 | 602 |
| 256 | 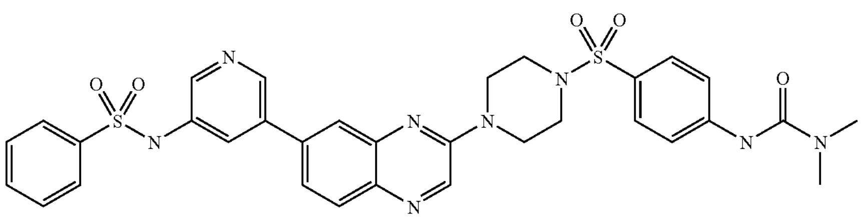 | 672 |
| 257 | 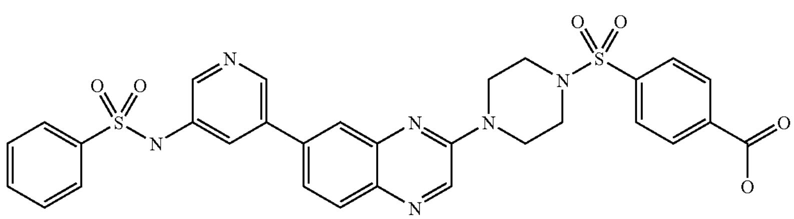 | 630 |
| 258 | 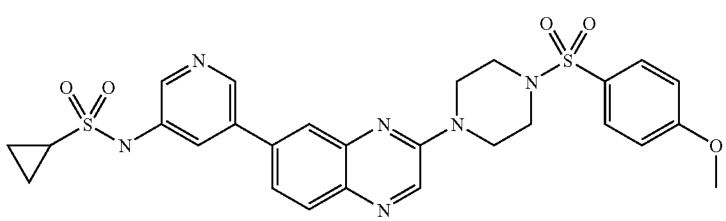 | 581 |
| 259 | 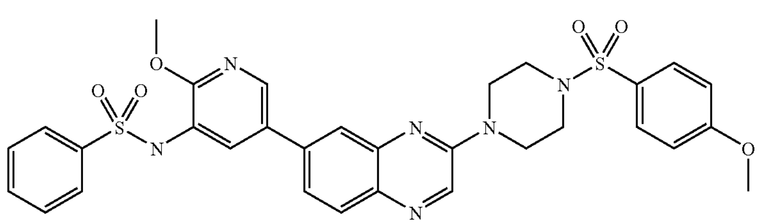 | 647 |

-continued

| Example | Structure | MS(ES) [M + H]+ |
|---|---|---|
| 260 | 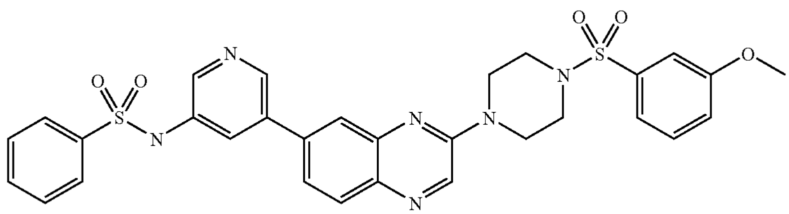 | 616 |
| 261 | 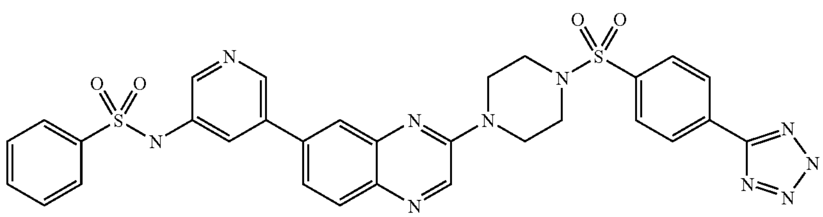 | 654 |
| 262 | 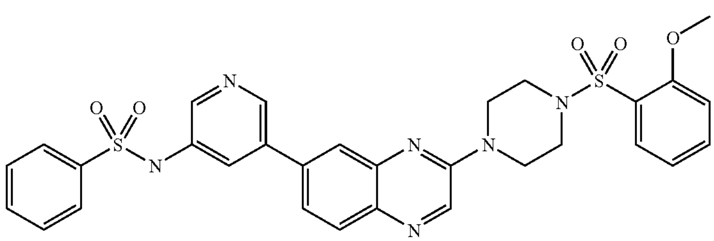 | 616 |
| 263 | 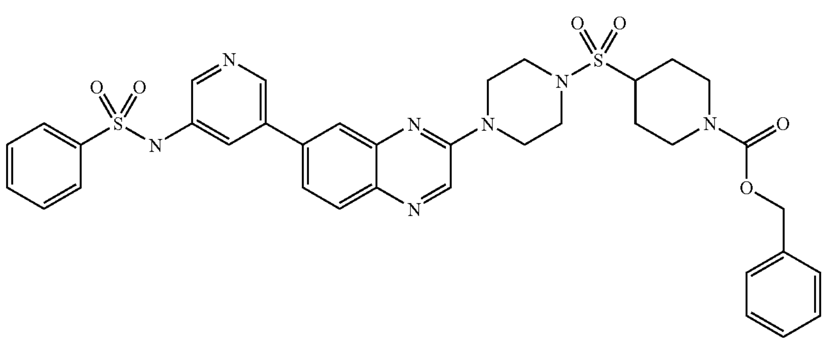 | 728 |
| 264 | 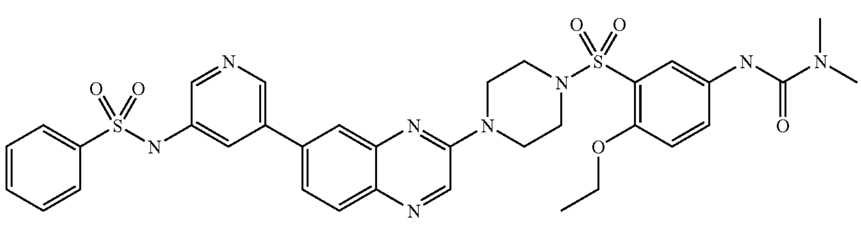 | 717 |
| 265 | 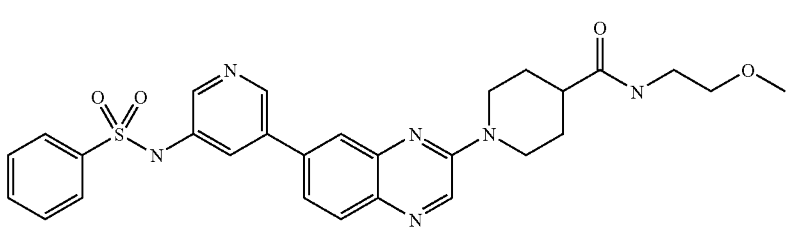 | 547 |

-continued

| Example | Structure | MS(ES) [M + H]+ |
|---------|-----------|-----------------|
| 266 | 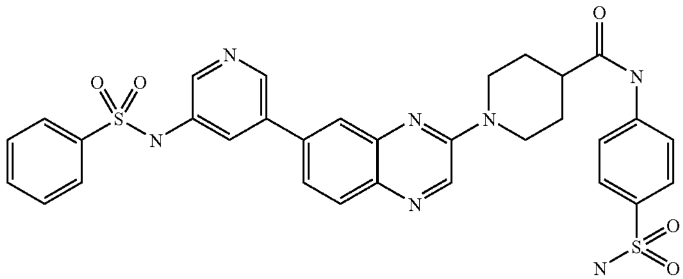 | 644 |
| 267 | 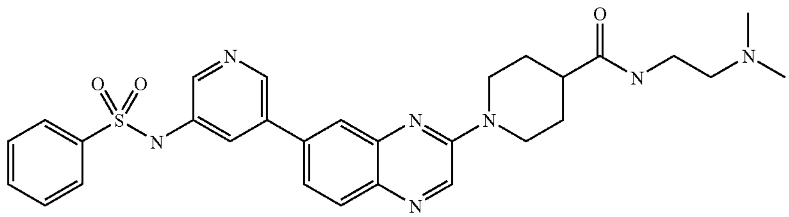 | 560 |
| 268 | 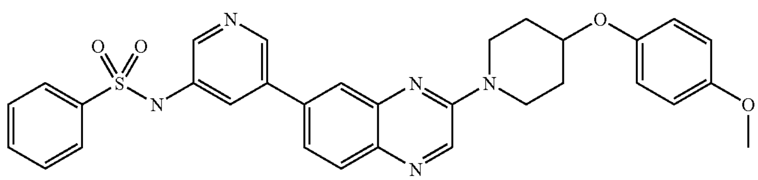 | 584 |
| 269 | 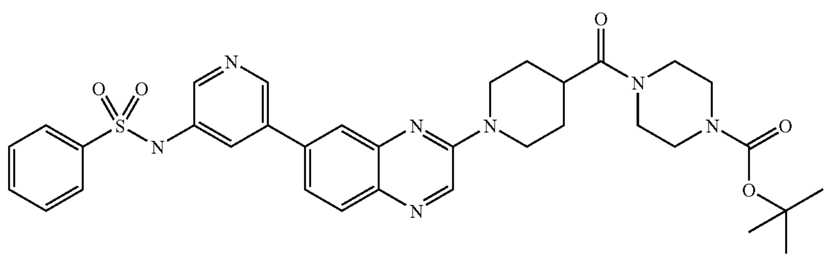 | 658 |

EXAMPLE 270

Preparation of N-(5-{3-[(1-methyl-1H-pyrazol-3-yl)amino]-6-quinoxalinyl}-3-pyridinyl)benzenesulfonamide

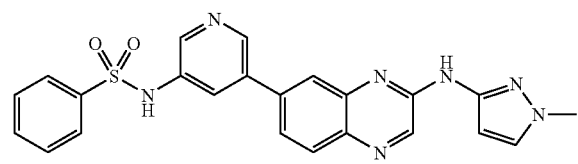

a) 7-bromo-N-(1-methyl-1H-pyrazol-3-yl)-2-quinoxalinamine

A slurry of 7-bromo-2-chloroquinoxaline (1.20 mmol), 1-methyl-1H-pyrazol-3-amine (2.50 mmol), potassium t-butoxide (2.50 mmol) in 1,4-dioxane (5 ml) was stirred at 100° C. for 30 minutes in the Smith Synthesizer microwave reactor. The reaction was poured into water (25 ml) upon which a precipitate formed, which was filtered and dried to afford the title compound (250 mg, 67%) as a yellow solid. MS(ES)+ m/e 303.9 [M+H]+.

b) N-(5-{3-[(1-methyl-1H-pyrazol-3-yl)amino]-6-quinoxalinyl}-3-pyridinyl)benzenesulfonamide A slurry of 7-bromo-N-(1-methyl-1H-pyrazol-3-yl)-2-quinoxalinamine (0.37 mmol), N-[5-(4,4,5,5-tetramethyl-1,3,2-dioxaborolan-2-yl)-3-pyridinyl]benzenesulfonamide (0.55 mmol), and [1,1'-bis(diphenylphosphino)ferrocene]dichloropalladium(II) dichloromethane complex (1:1) (0.03 mmol) in 1,4-dioxane (4 ml) and 2M solution potassium carbonate (2 ml) was stirred at 100° C. for 2 hours. The reaction was cooled to ambient temperature, separated the organic layer and purified directly on silica by column chromatography (10% methanol/ethyl acetate). The desired fractions were combined and concentrated to give the title compound (81 mg, 32%) as a pale green solid. MS(ES)+ m/e 458.1 [M+H]+.

The following compound was prepared following the procedures in Example 270 using the appropriate amine:

| Example | Structure | MS(ES) [M + H]+ |
|---|---|---|
| 271 | 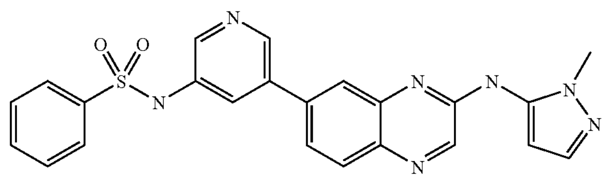 | 458 |

EXAMPLE 272

Preparation of N-{5-[3-(4-{[2-(methylsulfonyl)ethyl]amino}-1-piperidinyl)-6-quinoxalinyl]-3-pyridinyl}benzenesulfonamide

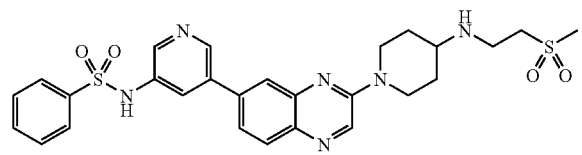

a) 1-(7-bromo-2-quinoxalinyl)-N-[2-(methylsulfonyl)ethyl]-4-piperidinamine

A slurry of 1-(7-bromo-2-quinoxalinyl)-4-piperidinone (0.98), 2-(methylsulfonyl)ethanamine (2.90 mmol), sodium triacetoxyborohydride (2.90 mmol), triethylamine (1.90 mmol) stirred in a solution of dichloromethane (4 ml) and acetic acid (1 ml) for 18 hours at ambient temperature. The reaction was concentrated and then triturated with ethyl acetate:hexanes (1:1) which was filtered and dried to give the title compound (210 mg, 52%) as a white solid. MS(ES)+ m/e 415.1 [M+H]+.

b) N-(5-{3-[(1-methyl-1H-pyrazol-3-yl)amino]-6-quinoxalinyl}-3-pyridinyl)benzenesulfonamide A slurry of a 1-(7-bromo-2-quinoxalinyl)-N-[2-(methylsulfonyl)ethyl]-4-piperidinamine (0.48 mmol), N-[5-(4,4,5,5-tetramethyl-1,3,2-dioxaborolan-2-yl)-3-pyridinyl]benzenesulfonamide (0.53 mmol), and [1,1'-bis(diphenylphosphino)ferrocene]dichloropalladium(II) dichloromethane complex (1:1) (0.03 mmol) in 1,4-dioxane (4 ml) and 2M solution potassium carbonate (2 ml) was stirred at 100° C. for 3 hours. The reaction was cooled to ambient temperature, separated the organic layer and purified directly on silica by column chromatography (10% methanol/ethyl acetate). The desired fractions were combined and concentrated to give the title compound (15 mg, 6%) as a tan solid. MS(ES)+ m/e 567.4 [M+H]+.

EXAMPLE 273

Preparation of N-{5-[3-(1-piperazinyl)-6-quinoxalinyl]-3-pyridinyl}benzenesulfonamide

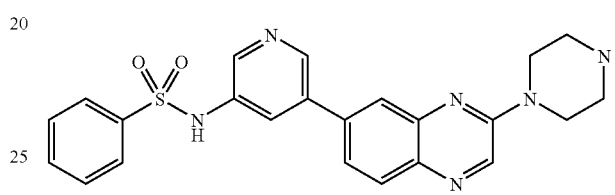

To a solution of 1,1-dimethylethyl 4-(7-{5-[(phenylsulfonyl)amino]-3-pyridinyl}-2-quinoxalinyl)-1-piperazinecarboxylate (1.80 mmol) in acetonitrile (4 ml) was added concentrated trifluoroacetic acid (4 ml). The reaction stirred at ambient temperature for 18 hours and was then concentrated to an orange oil. The residue was neutralized with 10% sodium carbonate solution and purified on silica by column chromatography (15% methanol/ethyl acetate). The desired fractions were combined and concentrated to give the title compound (500 mg, 61%) as a tan solid. MS(ES)+ m/e 447.2 [M+H]+.

EXAMPLE 274

Preparation of N-[5-(3-{4-[(2-methylpropyl)sulfonyl]-1-piperazinyl}-6-quinoxalinyl)-3-pyridinyl]benzenesulfonamide

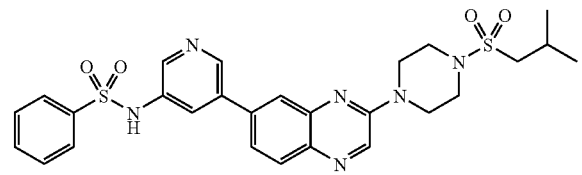

To a solution of N-{5-[3-(1-piperazinyl)-6-quinoxalinyl]-3-pyridinyl}benzenesulfonamide (0.20 mmol) and triethylamine (0.20 mmol) in dichloromethane (2 ml) was added a sulfonyl chloride such as 2-methyl-1-propanesulfonyl chloride (0.22 mmol). The reaction stirred for 18 hours at ambient temperature and purified on silica by column chromatography (80% ethyl acetate/hexanes). The desired fractions were combined and concentrated to give the title compound (22 mg, 20%) as an off-white solid. MS(ES)+ m/e 567.3 [M+H]+.

The following compounds were or can be prepared following the procedures in Example 274 using the appropriate sulfonyl chloride:

| Example | Structure | MS(ES) [M + H]+ |
|---|---|---|
| 275 | 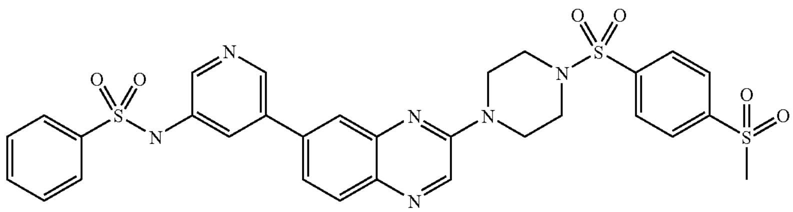 | 664 |
| 276 | 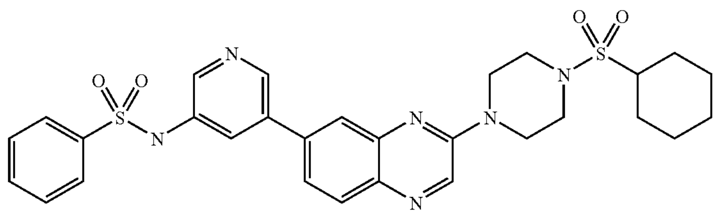 | 593 |
| 277 | 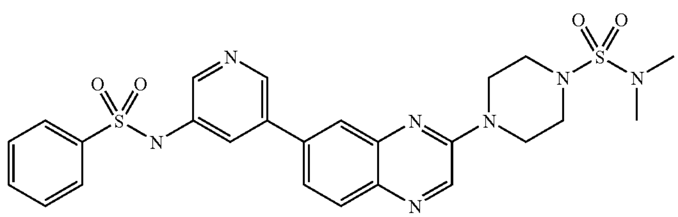 | 554 |
| 278 | 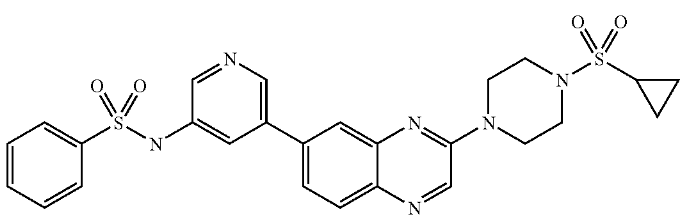 | 551 |

EXAMPLE 279

Preparation of 3-[(7-{5-[(phenylsulfonyl)amino]-3-pyridinyl}-2-quinoxalinyl)amino]benzoic acid

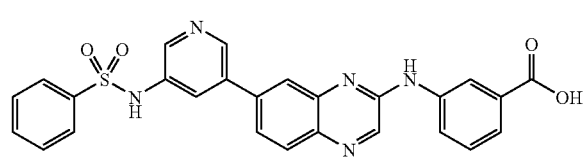

a) 3-[(7-bromo-2-quinoxalinyl)amino]-5-(methyloxy)benzoic acid

A slurry of 7-bromo-2-chloroquinoxaline (1.20 mmol) and an aniline such as 3-aminobenzoic acid (3.70 mmol) in a polar solvent such as dimethylsulfoxide (5 ml) was stirred for 2 hours at 120° C. The reaction was poured into ice-water upon which a precipitate formed. The precipitate was filtered and dried to afford the title compound (400 mg, 94%) as a yellow solid. MS(ES)+ m/e 345.8 [M+H]+.

b) 3-[(7-{5-[(phenylsulfonyl)amino]-3-pyridinyl}-2-quinoxalinyl)amino]benzoic acid A slurry of 3-[(7-bromo-2-quinoxalinyl)amino]-5-(methyloxy)benzoic acid (0.73 mmol), N-[5-(4,4,5,5-tetramethyl-1,3,2-dioxaborolan-2-yl)-3-pyridinyl]benzenesulfonamide (0.80 mmol), and [1,1'-bis(diphenylphosphino)ferrocene] dichloropalladium(II) dichloromethane complex (1:1) (0.06 mmol) in 1,4-dioxane (4 ml) and 2M solution potassium carbonate (2 ml) was stirred at 100° C. for 18 hours. The reaction was cooled to ambient temperature, separated the organic layer and purified directly on silica by column chromatography (100% ethyl acetate). The desired fractions were combined and concentrated to give the title compound (60 mg, 16%) as a yellow solid. MS(ES)+ m/e 497.8 [M+H]+.

The following compounds were or can be prepared following the procedures in Example 279 using the appropriate aniline. Alternatively, in some instances, the aniline in step a was or can be pretreated with 3 equivalents of sodium hydride in a solvent such as N,N-dimethylformamide prior to reaction with 7-bromo-2-chloroquinoxaline:

| Example | Structure | MS(ES) [M + H]+ |
|---|---|---|
| 280 | 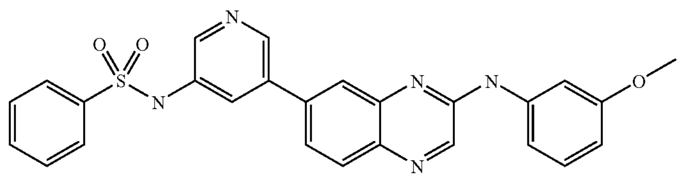 | 483 |
| 281 | 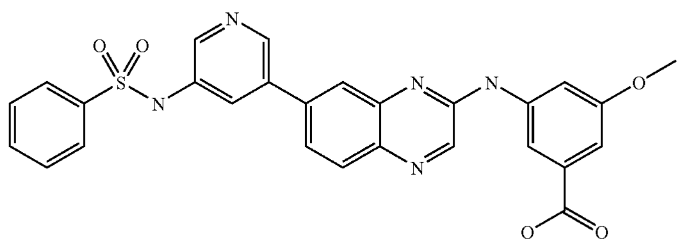 | 527 |
| 282 | 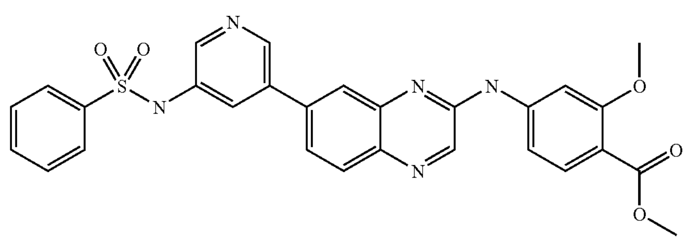 | 542 |
| 283 | 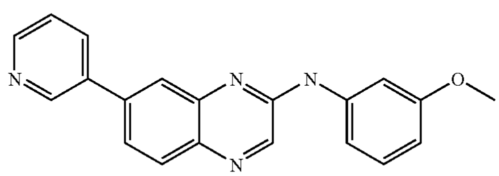 | 329 |
| 284 | 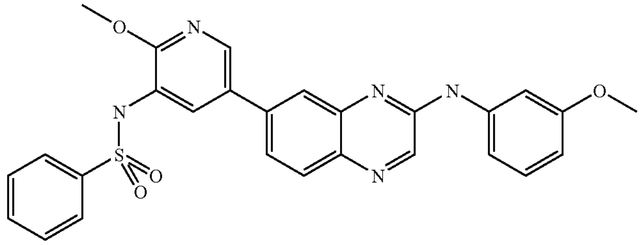 | 514 |
| 285 | 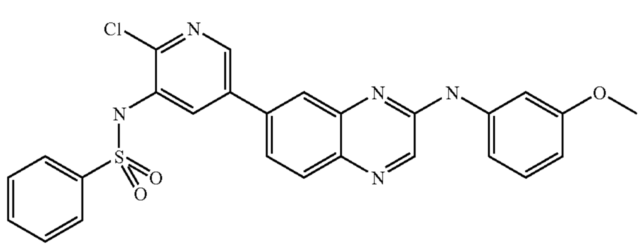 | 519 |

EXAMPLE 286

Preparation of N-{5-[3-(2-furanyl)-6-quinoxalinyl]-3-pyridinyl}benzenesulfonamide

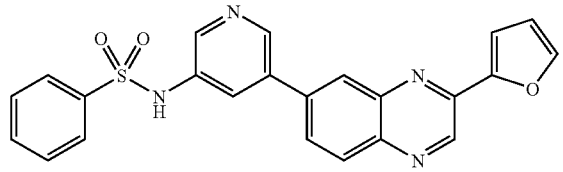

A slurry of 7-bromo-2-chloroquioxaline (0.82 mmol), a boronic acid such as 2-furan boronic acid (0.82 mmol), [1,1'-bis(diphenylphosphino)ferrocene]dichloropalladium(II) dichloromethane complex (1:1) (0.06 mmol), in 1,4-dioxane (4 ml) and 2M solution potassium carbonate (2 ml) was stirred at 100° C. for 3 hour. Then N-[5-(4,4,5,5-tetramethyl-1,3,2-dioxaborolan-2-yl)-3-pyridinyl]benzenesulfonamide (0.90 mmol) was added and the reaction mixture stirred at 100° C. for 18 hours. The reaction was cooled to ambient temperature, the organic layer separated and purified directly on silica by column chromatography (50% ethyl acetate/hexanes). The desired fractions were combined and concentrated to give the title compound (50 mg, 14%) as a tan solid. MS(ES)+ m/e 429.0 [M+H]+.

The following compounds were or can be prepared following the procedures in Example 286 using the appropriate boronic acid, bornate ester or stannane reagent:

| Example | Structure | MS(ES) [M + H]+ |
|---------|-----------|-----------------|
| 287 | 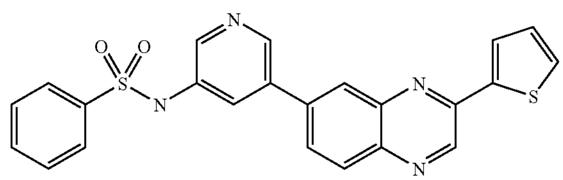 | 443 |
| 288 | 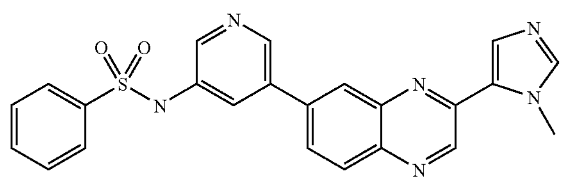 | 443 |
| 289 | 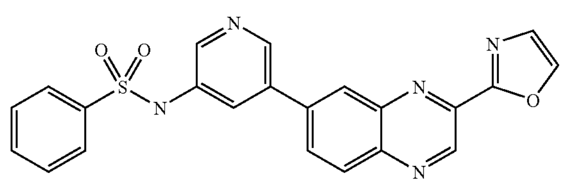 | 430 |
| 290 | 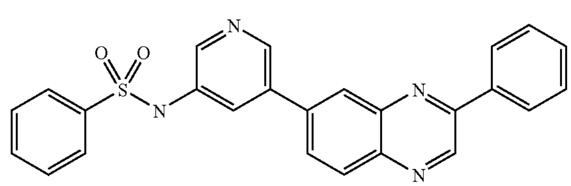 | 439 |
| 291 | 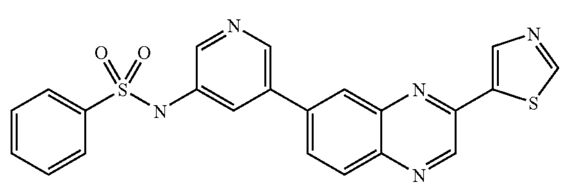 | 446 |
| 292 | 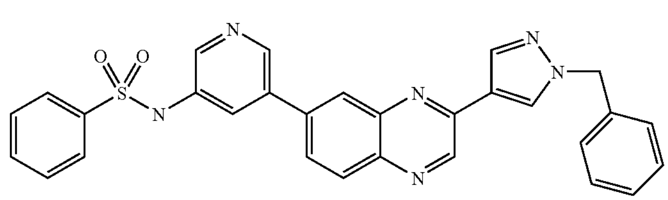 | 519 |

EXAMPLE 293

Preparation of 1,1-dimethylethyl 3-oxo-4-(7-{5-[(phenylsulfonyl)amino]-3-pyridinyl}-2-quinoxalinyl)-1-piperazinecarboxylate

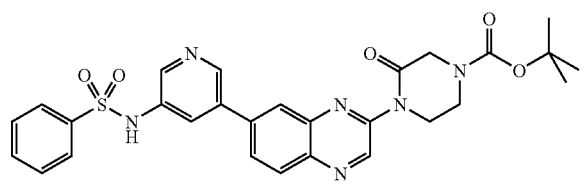

a) 1,1-dimethylethyl 4-(7-bromo-2-quinoxalinyl)-3-oxo-1-piperazinecarboxylate

A slurry of 7-bromo-2-chloroquioxaline (6.20 mmol), 1,1-dimethylethyl 3-oxo-1-piperazinecarboxylate (7.4 mmol), (0.06 mmol), Xantphos (0.28 mmol), cesium carbonate (9.20 mmol) in 1,4-dioxane (30 ml) was stirred at 100° C. for 18 hour. The reaction was cooled to ambient temperature, filtered through a pad of celite and purified directly on silica by column chromatography (50% ethyl acetate/hexanes). The desired fractions were combined and concentrated to give the title compound (1.3 g, 50%) as a yellow solid. MS(ES)+ m/e 409.2 [M+H]+.

b) 1,1-dimethylethyl 3-oxo-4-(7-{5-[(phenylsulfonyl)amino]-3-pyridinyl}-2-quinoxalinyl)-1-piperazinecarboxylate A slurry of 1,1-dimethylethyl 4-(7-bromo-2-quinoxalinyl)-3-oxo-1-piperazinecarboxylate (1.30 mmol), N-[5-(4,4,5,5-tetramethyl-1,3,2-dioxaborolan-2-yl)-3-pyridinyl]benzenesulfonamide (1.35 mmol), [1,1'-bis(diphenylphosphino)ferrocene]dichloropalladium(II) dichloromethane complex (1:1) (0.10 mmol), in 1,4-dioxane (6 ml) and saturated sodium bicarbonate solution (2 ml) was stirred at 100° C. for 1 hour. The reaction was cooled to ambient temperature, separated the organic layer and purified directly on silica by column chromatography (80% ethyl acetate/hexanes). The desired fractions were combined and concentrated to give the title compound (150 mg, 22%) as a tan solid. MS(ES)+ m/e 561.1 [M+H]+.

EXAMPLE 294

Preparation of N-{5-[3-(2-oxo-1-piperazinyl)-6-quinoxalinyl]-3-pyridinyl}benzenesulfonamide

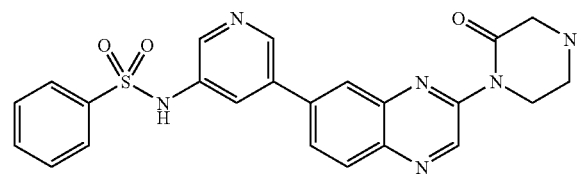

To a solution of 1,1-dimethylethyl 3-oxo-4-(7-{5-[(phenylsulfonyl)amino]-3-pyridinyl}-2-quinoxalinyl)-1-piperazinecarboxylate (0.21 mmol) in acetonitrile (4 ml) was added concentrated trifluoroacetic acid (4 ml). The reaction stirred at ambient temperature for 1 hour and was then concentrated to an orange oil. The residue was neutralized with saturated sodium bicarbonate solution upon which a precipitate formed. The precipitate was dissolved in ethyl acetate and crashed out of solution with hexanes, which was filtered and dried to afford the title compound (66 mg, 67%) as an off-white solid. MS(ES)+ m/e 461.2 [M+H]+.

EXAMPLE 295

Preparation of N-(5-{3-[4-(methylsulfonyl)-2-oxo-1-piperazinyl]-6-quinoxalinyl}-3-pyridinyl)benzenesulfonamide

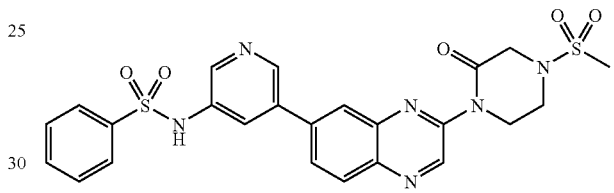

a) 1-(7-bromo-2-quinoxalinyl)-2-piperazinone

To a solution of 1,1-dimethylethyl 4-(7-bromo-2-quinoxalinyl)-3-oxo-1-piperazinecarboxylate (1.45 mmol) in acetonitrile (10 ml) was added concentrated trifluoroacetic acid (10 ml). The reaction stirred at ambient temperature for 1 hour and was then concentrated to an orange oil. The residue was neutralized with saturated sodium bicarbonate solution and extracted into ethyl acetate (3×10 ml). The combined organic layers were washed with brine, dried over sodium sulfate, filtered, and concentrated. The product was then purified on silica by column chromatography (20% methanol/ethyl acetate). The desired fractions were combined and concentrated to give the title compound (450 mg, 60%) as a white solid. MS(ES)+ m/e 309.1 [M+H]+.

b) 1-(7-bromo-2-quinoxalinyl)-4-(methylsulfonyl)-2-piperazinone

To a solution of 1-(7-bromo-2-quinoxalinyl)-2-piperazinone (0.48 mmol) and triethylamine (1.45 mmol), in dichloromethane (5 ml) was added a sulfonyl chloride such as methylsulfonyl chloride (1.45 mmol). The reaction stirred for 3 hours at ambient temperature and then poured into water (10 ml) and extracted with ethyl acetate (3×20 ml). The combined organic layers were washed with brine, dried over sodium sulfate, filtered and concentrated to give the title compound (200 mg, 96%) as a white solid. MS(ES)+ m/e 384.9 [M+H]+.

The following compound was prepared following the procedures in Example 295 using the appropriate sulfonyl chloride:

| Example | Structure | MS(ES) [M + H]+ |
|---|---|---|
| 296 | 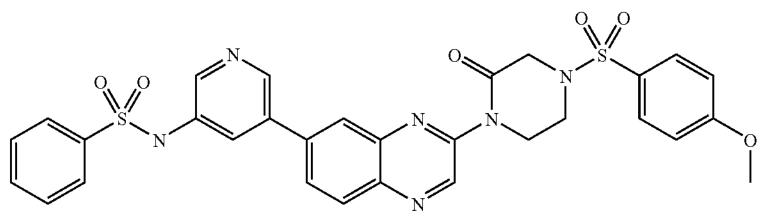 | 631 |

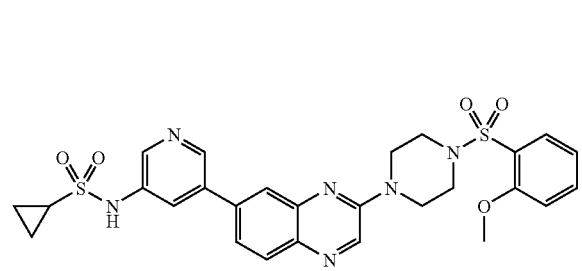

EXAMPLE 297

Preparation of N-{5-[3-(4-{[2-(methyloxy)phenyl]sulfonyl}-1-piperazinyl)-6-quinoxalinyl]-3-pyridinyl}cyclopropanesulfonamide a) 7-bromo-2-(4-{[2-(methyloxy)phenyl]sulfonyl}-1-piperazinyl)quinoxaline To a solution of 7-bromo-2-(1-piperazinyl)quinoxaline (3.41 mmol) in pyridine (20 ml) was added 2-(methyloxy)benzenesulfonyl chloride (10.23 mmol). The reaction stirred for 18 hours at 50° C. The reaction was cooled to ambient temperature and a yellow precipitate was filtered and triturated with methanol to afford the title compound (1.16 g, 73% yield) as a pale yellow solid. MS(ES)+ m/e 463.0 [M+H]+.

b) N-{5-[3-(4-{[2-(methyloxy)phenyl]sulfonyl}-1-piperazinyl)-6-quinoxalinyl]-3-pyridinyl}cyclopropanesulfonamide A slurry of 7-bromo-2-(4-{[2-(methyloxy)phenyl]sulfonyl}-1-piperazinyl)quinoxaline (0.96 mmol), bis(pinacolato)diboron (0.54 mmol), potassium acetate (1.16 mmol), and [1,1'-bis(diphenylphosphino)ferrocene]dichloropalladium (II) dichloromethane complex (1:1) (0.05 mmol) in 1,4-dioxane (4 ml) was heated at 100° C. After the reaction stirred for 1 hour, a bromide such as N-(5-bromo-3-pyridinyl)cyclopropanesulfonamide (0.54 mmol) and 2M solution potassium carbonate (4 ml) was added and continued to stir for 1 hour. The reaction was cooled to ambient temperature, separated the organic layer and purified directly on silica by column chromatography (80% ethyl acetate/hexanes). The desired fractions were combined and concentrated to give the title compound (44 mg, 14% yield) as a pale yellow solid. MS(ES)+ m/e 581.3 [M+H]+.

EXAMPLE 298

Preparation of N-{2-(methyloxy)-5-[3-(4-{[2-(methyloxy)phenyl]sulfonyl}-1-piperazinyl)-6-quinoxalinyl]-3-pyridinyl}cyclopropanesulfonamide

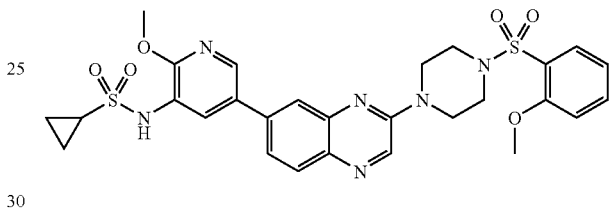

a) 7-bromo-2-(1-piperazinyl)quinoxaline

A solution of 7-bromo-2-chloroquinoxaline (20.5 mmol) and piperazine (61.6 mmol) in N,N-dimethylformamide (100 ml) was stirred at 100° C. for 18 hours. The reaction was poured into ice-water (200 ml) and extracted with ethyl acetate (3×100 ml). The combined organic layers were washed with brine, dried over sodium sulfate, filtered and concentrated in vacuo. The product was triturated, filtered, and dried to afford the title compound (3.5 g, 58%) as a yellow solid. MS(ES)+ m/e 292.9 [M+H]+.

b) 7-bromo-2-(4-{[2-(methyloxy)phenyl]sulfonyl}-1-piperazinyl)quinoxaline

To a solution of 7-bromo-2-(1-piperazinyl)quinoxaline (3.41 mmol) in pyridine (20 ml) was added 2-(methyloxy)benzenesulfonyl chloride (10.23 mmol). The reaction mixture was stirred for 18 hours at 50° C. As the reaction cooled to ambient temperature, a yellow precipitate formed which was filtered and the solid triturated with methanol. The precipitate was collected to afford the title compound (1.16 g, 73%) as a pale yellow solid. MS(ES)+ m/e 463.0 [M+H]+.

c) N-{2-(methyloxy)-5-[3-(4-{[2-(methyloxy)phenyl]sulfonyl}-1-piperazinyl)-6-quinoxalinyl]-3-pyridinyl}cyclopropanesulfonamide A slurry of 7-bromo-2-(4-{[2-(methyloxy)phenyl]sulfonyl}-1-piperazinyl)quinoxaline (0.54 mmol), bis(pinacolato)diboron (0.81 mmol), potassium acetate (2.15 mmol), and [1,1'-bis(diphenylphosphino)ferrocene]dichloropalladium (II) dichloromethane complex (1:1) (0.05 mmol) in 1,4-dioxane (4 ml) was heated at 100° C. After the reaction stirred for 1 hour, N-[5-bromo-2-(methyloxy)-3-pyridinyl]cyclopropanesulfonamide (0.81 mmol) and 2M solution potassium carbonate (2 ml) was added and continued to stir for 1 hour. The reaction was cooled to ambient temperature, separated the organic layer and purified directly on silica by column chromatography (30-100% ethyl acetate/hexanes). The desired fractions were combined and concentrated to give the title compound (125 mg, 38% yield) as a pale tan solid. MS(ES)+ m/e 611.2 [M+H]⁺.

The following compounds were or can be prepared following the procedures in Example 298 using the appropriate heteroaryl bromide coupling partner in step c:

| Example | Structure | MS(ES) [M + H]⁺ |
|---|---|---|
| 299 | 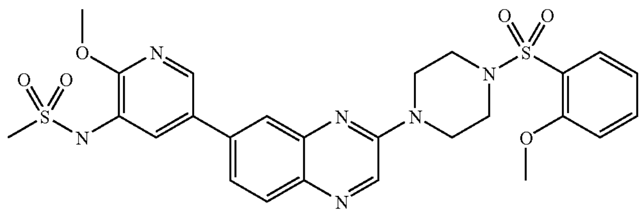 | 585 |
| 300 | 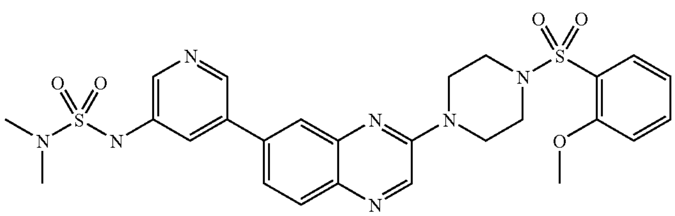 | 584 |

EXAMPLE 301

Preparation of N,N-dimethyl-1-(7-{5-[(phenylsulfonyl)amino]-3-pyridinyl}-2-quinoxalinyl)-4-piperidinesulfonamide

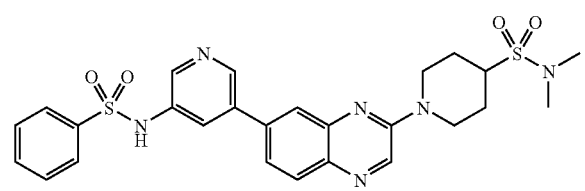

a) Phenylmethyl 4-[(dimethylamino)sulfonyl]-1-piperidinecarboxylate

A suspension of an amine such as dimethylamine (4.72 mmol) and sodium hydride (4.72 mmol) in N,N-dimethylformamide (10 ml) was stirred for five minutes at room temperature. Then phenylmethyl 4-(chlorosulfonyl)-1-piperidinecarboxylate (1.60 mmol) was added to the reaction mixture and stirred at 100° C. for 3 hours. The reaction mixture was poured into water (25 ml) and extracted with ethyl acetate (3×25 ml). The combined organic layers were washed with brine, dried over sodium sulfate, filtered, and concentrated to give the title compound (410 mg, 80% yield) as an off-white solid. MS(ES)+ m/e 327.1 [M+H]⁺.

b) N,N-dimethyl-4-piperidinesulfonamide

A solution of phenylmethyl 4-[(dimethylamino)sulfonyl]-1-piperidinecarboxylate (1.19 mmol) and 10% wt palladium/carbon (0.09 mmol) in methanol (10 ml) was vacuum pumped and back-filled with nitrogen three times. The nitrogen atmosphere was then replaced with hydrogen via a balloon and the reaction stirred for 1 hour at ambient temperature. The reaction was then filtered through a pad of celite and concentrated to give the title compound (200 mg, 87% yield), which was used directly in the next reaction without further purification. 1H NMR (400 MHz, DMSO-d₆) δ ppm 3.33 (bs, 1H) 3.30-3.22 (m, 1H) 2.96 (d, J=12.13, 2H) 2.84 (s, 6H) 2.46 (td, J=2.53, 12.38, 2H) 1.80 (d, J=12.13, 2H) 1.46 (qt, J=4.17, 12.34, 2H)

c) 1-(7-bromo-2-quinoxalinyl)-N,N-dimethyl-4-piperidinesulfonamide

A suspension of N,N-dimethyl-4-piperidinesulfonamide (1.03 mmol) and sodium hydride (1.03 mmol) in N,N-dimethylformamide (5 ml) stirred for five minutes at room temperature. Then 7-bromo-4-chloroquionoxaline (0.86 mmol) was added to the reaction mixture and stirred at 100° C. for 3 hours. The reaction was poured into water (30 ml) and extracted with ethyl acetate (3×25 ml). The combined organic layers were washed with brine, dried over sodium sulfate, filtered, concentrated, and purified on silica by column chromatography to give the title compound (170 mg, 50% yield) as yellow solid. MS(ES)+ m/e 399.0 [M+H]⁺.

d) N,N-dimethyl-1-(7-{5-[(phenylsulfonyl)amino]-3-pyridinyl}-2-quinoxalinyl)-4-piperidinesulfonamide A slurry of 1-(7-bromo-2-quinoxalinyl)-N,N-dimethyl-4-piperidinesulfonamide (0.43 mmol), N-[5-(4,4,5,5-tetramethyl-1,3,2-dioxaborolan-2-yl)-3-pyridinyl]benzenesulfonamide (0.47 mmol), and [1,1'-bis(diphenylphosphino)ferrocene]dichloropalladium(II) dichloromethane complex (1:1) (0.03 mmol) in 1,4-dioxane (4 ml) and 2M solution potassium carbonate (2 ml) was stirred at 100° C. for 18 hours. The reaction was cooled to ambient temperature, separated the organic layer and purified directly on silica by column chromatography (5% methanol/ethyl acetate). The desired fractions were combined and concentrated to give the title compound (102 mg, 43% yield) as a yellow solid. MS(ES)+ m/e 539.2 [M+H]⁺.

The following compounds were or can be prepared following the procedures in Example 301 using the appropriate amine:

| Example | Structure | MS(ES) [M + H]+ |
|---|---|---|
| 302 | 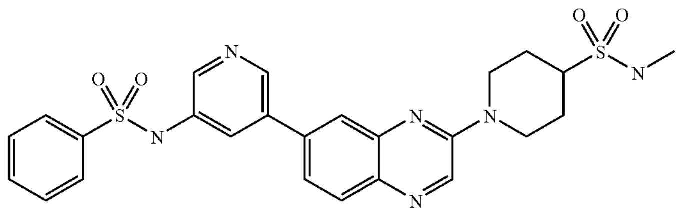 | 539.2 |
| 303 | 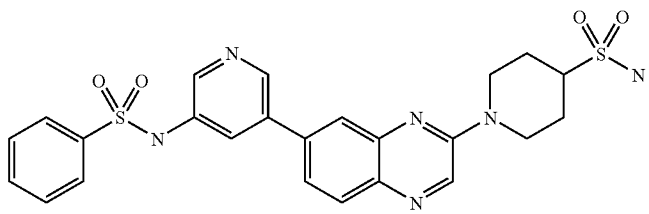 | 525.4 |
| 304 | 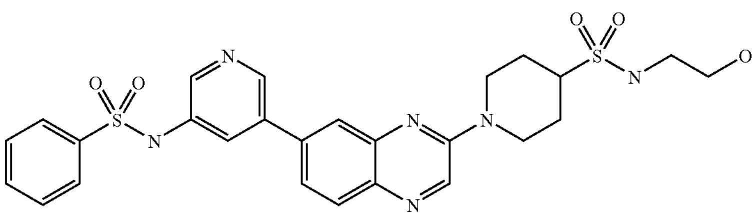 | 569.3 |

Intermediates:

Intermediate 1

Preparation of 5-bromo-1H-pyrazolo[3,4-b]pyridine

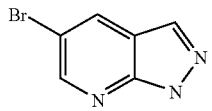

a) 5-bromo-2-fluoro-3-pyridinecarbaldehyde

Following the procedure described in WO2006015124 and trituration of the crude product in hexanes instead of crystallization from cyclohexane afforded the title compound as an off-white solid (68%). MS(ES)+ m/e 203.8, 205.7 [M+H]+.

b) 5-bromo-3-(4,4,5,5-tetramethyl-1,3-dioxolan-2-yl)-2(1H)-pyridinone hydrazone

Following the procedure described in WO2006015124 without the addition of hydrogen chloride provided the title compound as a yellow solid. MS(ES)+ m/e 317.9 [M+H]+. This crude material was used directly in the next step.

c) 5-bromo-1H-pyrazolo[3,4-b]pyridine

Following the procedure described in WO2006015124 provided the title compound as a yellow solid (94%, 2 steps). MS(ES)+ m/e 197.7, 199.7 [M+H]+.

Intermediate 2

Preparation of 2-amino-5-bromo-N,N-dimethyl-3-pyridine-sulfonamide

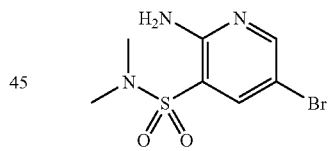

a) 2-amino-5-bromo-3-pyridinesulfonyl chloride

To a cooled (0° C.) solution of chlorosulfonic acid (58 mL) under vigorous stirring was added 5-bromo-2-pyridinamine (86.7 mmol) portionwise. The reaction mixture was then heated at reflux for 3 hrs. Upon cooling to room temperature, the reaction mixture was poured over ice (~100 g) with vigorous stirring. The resulting yellow precipitate was collected by suction filtration, washing with cold water and petroleum ether to provide the title compound as an orange-yellow solid (18.1 g, 77% yield). MS(ES)+ m/e 272.8 [M+H]+.

Other sulfonyl chlorides can be prepared using this procedure by varying the choice of substituted aryl or heteroaryl.

b) 2-amino-5-bromo-N,N-dimethyl-3-pyridinesulfonamide

To a cold (0 □C) suspension of 2-amino-5-bromo-3-pyridinesulfonyl chloride (92.1 mmol) in dry 1,4-dioxane (92 mL) was added pyridine (101.3 mmol) followed by a 2M solution of dimethylamine in THF (101.3 mmol). The reaction was allowed to warm to rt for 2 h, heated to 50 □C for 1 h, then cooled to rt. After standing for 2 h, the precipitate was collected by filtration and rinsed with a minimal amount of cold water. Drying the precipitate to constant weight under high vacuum provided 14.1 g (55%) of the title compound as a white solid. MS(ES)+ m/e 279.8, 282.0 [M+H]+.

Other sulfonamides were or can be prepared using this procedure by varying the choice of starting sulfonyl chloride and amine.

Intermediate 3

Preparation of 2-amino-N,N-dimethyl-5-(4,4,5,5-tetramethyl-1,3,2-dioxaborolan-2-yl)-3-pyridinesulfonamide

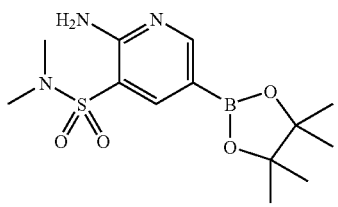

To a solution of 2-amino-5-bromo-N,N-dimethyl-3-pyridinesulfonamide (7.14 mmol) in 1,4-dioxane (35 mL) was added 4,4,4',4',5,5,5',5'-octamethyl-2,2'-bi-1,3,2-dioxaborolane (7.86 mmol), potassium acetate (28.56 mmol) and [1,1'-bis(diphenylphosphino)-ferrocene]dichloropalladium(II) dichloromethane complex (1:1) (0.571 mmol). The reaction mixture was stirred at 100° C. for 18 h. The reaction was concentrated in vacuo, re-dissolved in ethyl acetate (50 mL) and purified on silica using 60% ethyl acetate/hexanes to yield the title compound as a tan solid (86%). $^1$H NMR (400 MHz, DMSO-$d_6$) δ ppm 8.41 (d, 1H, J=1.52), 7.92 (d, 1H, J=1.77), 2.68 (s, 6H), 1.28 (s, 12H).

Other boronate or boronic acids can be prepared using this procedure by varying the choice of starting aryl or heteroaryl bromide.

Intermediate 4

Preparation of N-(5-bromo-2-chloro-3-pyridinyl)benzenesulfonamide

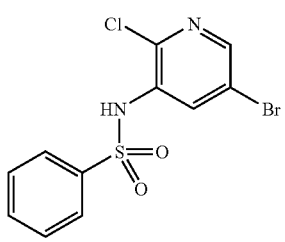

To a stirred solution of a pyridineamine such as 3-amino-5-bromo-2-chloropyridine (24 mmol) in dichloromethane (50 mL) was added pyridine (37 mmol) followed by benzenesulfonyl chloride (35 mmol) dropwise over 5 minutes. The reaction mixture was stirred at RT for 18 h and evaporated to dryness in vacuo. The residue was purified by flash chromatography on silica gel (15% hexanes in $CH_2Cl_2$ then 0 to 5% EtOAc in 15% hexanes in $CH_2Cl_2$). During evaporation of the solvents the product crashed out. The resultant slurry was diluted with hexanes, filtered and dried under vacuum to give the title compound (2.89 g, 34%) as a white solid. MS (ES) m/e 346.7 (M+H)+.

Other pyridinesulfonamides were or can be prepared using this procedure by varying the choice of starting pyridineamine and sulfonylchloride.

Intermediate 5

Preparation of N-[5-bromo-2-(methyloxy)-3-pyridinyl]-1-ethyl-1H-pyrazole-4-sulfonamide

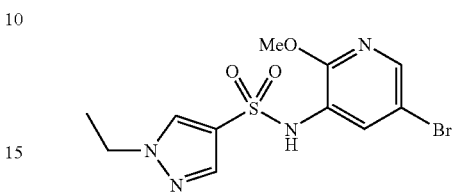

In an oven dried round bottom flask under a nitrogen atmosphere, a solution of 5-bromo-2-(methyloxy)-3-pyridinamine (268 mg, 1.320 mmol) in anhydrous pyridine (4 mL) was treated with 1-ethyl-1H-pyrazole-4-sulfonyl chloride (308 mg, 1.584 mmol) and the resultant reaction mixture stirred at room temperature for 90 min. The reaction mixture was concentrated in vacuo, diluted with ethyl acetate (100 mL) and water (30 mL), neutralized with saturated ammonium chloride (aq) and the product extracted into the organic layer. The aqueous layer was back-extracted with 40 mL ethyl acetate. The organic layers were combined, washed with brine (50 mL), dried over magnesium sulfate and concentrated in vacuo to give a yellow-brown solid. Purification by silica gel chromatography (0-50% ethyl acetate in hexanes) provided the title compound (368 mg, 77%) as a beige solid. MS(ES)+ m/e 361.0, 363.0 [M+H]+.

Related aryl-aminosulfonylpyridinyl bromides were or can be prepared using this procedure by varying the choice of starting pyridineamine and sulfonyl chloride.

Intermediate 6

Preparation of N-[5-bromo-2-(methyloxy)-3-pyridinyl]cyclopropanesulfonamide

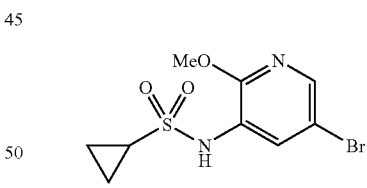

A solution of 5-bromo-2-(methyloxy)-3-pyridinamine (1.65 g, 8.13 mmol) in anhydrous pyridine (20 ml) was treated with neat cyclopropanesulfonyl chloride (1.371 g, 9.75 mmol) then stirred at room temperature for 20 h. The resulting slurry was concentrated under reduced pressure to a residue that was purified by column chromatography on silica, eluting with 30% hexanes in dichloromethane. The combined desired fractions were concentrated under reduced pressure to give the title compound (1.61 g, 60%) as an off white solid. MS(ES)+ m/e 306.9, 309.0 [M+H]+.

Related alkyl-aminosulfonylpyridinyl bromides were or can be prepared using this procedure by varying the choice of starting pyridineamine and sulfonyl chloride.

Intermediate 7

Preparation of N-(5-bromo-2-methyl-3-pyridinyl)cyclopropanesulfonamide a) 5-bromo-2-methyl-3-nitropyridine

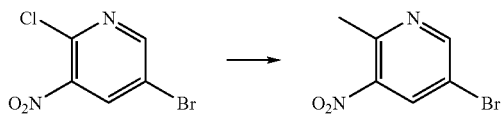

Sodium hydride (1.31 g, 54.8 mmol, 2.19 g of 60% in mineral oil) was suspended in dry THF (70 mL) and to this suspension was added 5-bromo-2-chloro-3-nitropyridine as a solid. An ambient water bath was placed under the reaction and a solution of diethyl malonate in dry THF (15 mL) was added carefully via addition funnel. Observed a vigorous evolution of gas. After 2 hours additional sodium hydride (0.202 g, 8.42 mmol, 0.337 g of 60% in mineral oil) was added and the reaction was stirred for 1.5 hours. The reaction was concentrated in vacuo, diluted with 6N HCl (100 ml), and refluxed overnight. The reaction was concentrated in vacuo and diluted with saturated sodium carbonate to pH 9. The basic aqueous mixture was diluted with dichloromethane and filtered through filter paper to remove an insoluble green solid. The filtrate was transferred to a separatory funnel and the layers were separated. The dichloromethane was washed with saturated sodium chloride (aq), dried over sodium sulfate, filtered and concentrated to give the title compound (5.79 g, 63.3%) as an orange oil. MS(ES)+ m/e 217 [M+H].

b) 5-bromo-2-methyl-3-pyridinamine

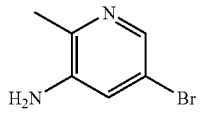

A mixture of 5-bromo-2-methyl-3-nitropyridine (5.68 g, 26.2 mmol) and tin (II) chloride dihydrate in ethyl acetate (200 mL) was refluxed for 2 hours and concentrated in vacuo. The residue was diluted with 6N NaOH (200 mL), water (100 mL), and dichloromethane (300 mL) and stirred at room temperature. The mixture was filtered through filter paper to remove small amounts of undissolved solid and the biphasic mixture was transferred to a separatory funnel. The layers were separated and the organic layer was washed with saturated NaCl, dried over Na$_2$SO$_4$, filtered and concentrated to give a gummy orange solid. The solid was triturated with warm hexanes, filtered, and dried in a Buchner funnel to give the title compound (3.03 g, 62%) as a tan solid. MS(ES)+ m/e 375 [2M+H].

c) N-(5-bromo-2-methyl-3-pyridinyl)cyclopropanesulfonamide

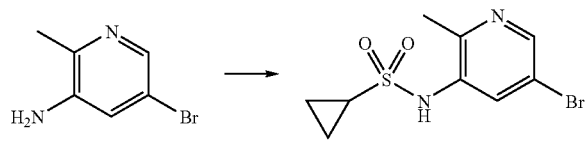

In an oven dried round bottom flask under nitrogen, a solution of 5-bromo-2-methyl-3-pyridinamine (150 mg, 0.802 mmol) in anhydrous pyridine (4 mL) was treated with cyclopropanesulfonyl chloride (0.098 mL, 0.962 mmol) and the resultant reaction mixture stirred at room temperature for 18.75 hours. The reaction mixture was concentrated in vacuo, diluted with ethyl acetate (100 mL) and water (30 mL), neutralized with saturated ammonium chloride (aq) and the product extracted into the organic layer. The aqueous layer was back-extracted with ethyl acetate (40 mL) and the combined organic layers washed with brine (50 mL), dried over magnesium sulfate, filtered and concentrated in vacuo to give a yellow-brown solid. Purification by silica gel chromatography (0-50% ethyl acetate in hexanes) provided the title compound (218 mg, 93%) as an off-white solid. MS(ES)+ m/e 290.9, 292.8 [M+H]+.

Related alkyl, aryl, or heteroaryl-aminosulfonylpyridinyl bromides can be prepared using this procedure by varying the choice of sulfonyl chloride.

Intermediate 8

Preparation of N-(5-bromo-3-pyridinyl)cyclopropanesulfonamide

In a 20 ml vial was combined 5-bromo-3-pyridinamine (7.5 g, 43.3 mmol) and cyclopropanesulfonyl chloride (9.14 g, 65.0 mmol), dioxane (6 mL) and pyridine (3 mL) to give a brown suspension. The reaction mixture was sealed and stirred at 50° C. for 24 h. LCMS showed product and 5% starting material. The reaction mixture was diluted with dichloromethane and washed with saturated sodium bicarbonate (aq). The organic layer was concentrated in vacuo and the residue was precipitated with water. Filtration and washing of the solid with water followed by hexanes provided the desired product as a brown solid (9.6 g, 80% yield). ESMS m/e: 276.8, 278.8 [M]+.

Related alkyl-aminosulfonylpyridinyl bromides were or can be prepared using this procedure by varying the choice of sulfonyl chloride.

Intermediate 9

Preparation of N-(5-bromo-3-pyridinyl)benzenesulfonamide

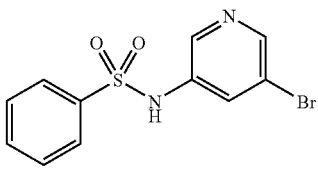

In a 500 mL round-bottomed flask was combined 5-bromo-3-pyridinamine (30 g, 173 mmol), triethylamine (53.2 mL, 381 mmol) and dichloromethane (150 mL). The reaction mixture was cooled to 0° C. and benzenesulfonyl chloride (48.9 mL, 381 mmol) was added slowly to give a brown solution. The reaction mixture was stirred for 1 h at room temperature, giving 77% bis-sulfonylated product, MW=454.8 and 17% desired mono-sulfonylated product, MW=312.9. The reaction mixture was concentrated in vacuo, the residue titrated with methanol and the solid filtered to yield a white solid.

This solid was suspended in a 1:1 methanol:6N sodium hydroxide (aq) solution and allowed to stir for 3 h at RT. LCMS showed 84% desired mono-sulfonylated product. The reaction mixture was concentrated in vacuo and neutralized with 6N HCl (aq). The precipitate that formed was filtered and dried to an off-white solid. The solid was titrated with MeOH, filtered, and dried to give clean desired product as an off-white solid (99% yield). ESMS m/e 315.0 [M+H]$^+$.

Related aryl- or heteroaryl-aminosulfonylpyridinyl bromides can be prepared using this procedure by varying the choice of sulfonyl chloride.

Intermediate 10

Preparation of N-(5-bromo-3-pyridinyl)-2,4-difluorobenzenesulfonamide

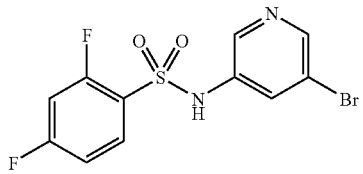

A solution of 5-bromo-3-pyridinamine (104 mmol) in dichloromethane (55 mL) was added dropwise over ~60 min to a stirred solution of triethylamine (230 mmol) and 2,4-difluorobenzenesulfonyl chloride (235 mmol) in dichloromethane (300 mL). After 1.5 h, additional 2,4-difluorobenzenesulfonyl chloride (53.4 mmol) was added, and after 2 days, more 2,4-difluorobenzenesulfonyl chloride (47.0 mmol) and triethylamine (108 mmol) were added. After 1 h, the resulting mixture of mono- and bis-sulfonylation products was concentrated in vacuo and the residue was suspended in methanol (500 mL) and then filtered to provide N-(5-bromo-3-pyridinyl)-N-[(2,4-difluorophenyl)sulfonyl]-2,4-difluorobenzenesulfonamide as a white solid (54.4 mmol, 52%).

A solution of the bis-sulfonylated intermediate (54.4 mmol) in 1,4-dioxane (300 mL) was heated to 80° C. A solution of potassium hydroxide (322 mmol) in water (133 mL) was added and the resultant reaction mixture was heated at reflux for 0.5 h. The dioxane was removed in vacuo and the resulting off-white suspension was acidified with concentrated HCl, causing the solids to dissolve and then a new off-white solid to emerge. The suspension was stirred for 30 min and then filtered, rinsing with water. The solid was dried in vacuo and then desiccated over P$_2$O$_5$ to afford the title product as an off-white solid (quantitative yield). ESMS m/e 347, 349 [M+H]$^+$.

Intermediate 11

Preparation of N-[5-(4,4,5,5-tetramethyl-1,32-dioxaborolan-2-yl)-3-pyridinyl]benzenesulfonamide

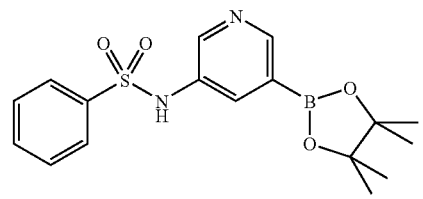

N-(5-bromo-3-pyridinyl)benzenesulfonamide (25 g, 80 mmol), 4,4,4',4',5,5,5',5'-octamethyl-2,2'-bi-1,3,2-dioxaborolane (24.33 g, 96 mmol), PdCl$_2$(dppf).CH$_2$Cl$_2$ (2.61 g, 3.19 mmol), and potassium acetate (31.3 g, 319 mmol) were added to a 500 mL round bottom flask equipped with an oven-dried stir bar and a reflux condensor under a nitrogen atmosphere. 1,4-Dioxane (400 ml) was added and the reaction mixture stirred at 100° C. for 18 h. LCMS showed complete conversion to desired product (89% boronic acid by LCMS, M+H=278.9). The reaction mixture was cooled to room temperature and then concentrated in vacuo to a black residue. The residue was suspended in water (250 mL) and extracted with ethyl acetate (4×150 mL). The combined black organic layers were dried over sodium sulfate and decolorizing carbon, filtered through a pad of celite and concentrated to yield an orange solid. The solid was titrated with dichloromethane, collected by suction filtration and dried in vacuo to yield a white solid (61% yield). ESMS m/e: 278.9 (boronic acid) [M+H]$^+$.

Related aryl- or heteroaryl-aminosulfonylpyridinyl boronate esters can be prepared using this procedure by varying the choice of starting aryl- or heteroaryl-aminosulfonylpyridinyl bromides.

Intermediate 12

Preparation of N'-(5-bromo-3-pyridinyl)-N,N-dimethylsulfamide

In an oven-dried flask under nitrogen, dimethylsulfamoyl chloride (0.310 mL, 2.89 mmol) was added by syringe to a solution of 3-amino-5-bromopyridine (500 mg, 2.89 mmol) and pyridine (0.467 mL, 5.78 mmol) in dichloromethane (10 mL) at room temperature. The reaction was stirred for 4 hours and then added additional dimethylsulfamoyl chloride (0.310 mL, 2.89 mmol) to the reaction and stirred overnight (20 hours). The reaction was concentrated in vacuo. The residue was taken up into 200 mL ethyl acetate and washed with saturated aqueous sodium bicarbonate solution (100 mL) followed by brine (100 mL). The organic layer was dried over magnesium sulfate and concentrated in vacuo to give the title compound (839 mg, 93%) as a brown solid. MS(ES)+ m/e 279.9, 282.0 [M+H]$^+$.

Related sulfamides can be prepared using this procedure by varying the choice of starting pyridineamine bromides and sulfamoyl chlorides.

Intermediate 13

Preparation of 7-bromo-2-(1H-pyrazol-4-yl)quinoxaline

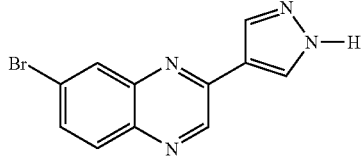

To a 100 mL high pressure vessel was added 1,1-dimethylethyl 4-(4,4,5,5-tetramethyl-1,3,2-dioxaborolan-2-yl)-1H-pyrazole-1-carboxylate (1.208 g, 4.11 mmol), 7-bromo-2-chloroquinoxaline (1 g, 4.11 mmol), $PdCl_2(dppf)\cdot CH_2Cl_2$ (0.168 g, 0.205 mmol), 1,4-dioxane (20.53 ml) and 2M aqueous potassium carbonate (10.27 ml, 20.53 mmol). The vessel was sealed and the reaction mixture heated at 100° C. overnight (21.5 hrs). LCMS showed 60% desired product (M+H=276.9) with no Boc group. The organic layer was separated and purified directly on a silica gel column, eluting with 50% ethyl acetate to 100% ethyl acetate in hexanes. The desired fractions were concentrated in vacuo to give a tan solid which was triturated with ethyl acetate, the insolubles collected by suction filtration and dried in vacuo to provide the title compound as a tan powder (508 mg, 45%). ESMS m/e 276.9 [M+H]+.

Intermediate 14

Preparation of 2-[4-(7-bromo-2-quinoxalinyl)-1H-pyrazol-1-yl]-N,N-dimethylethanamine

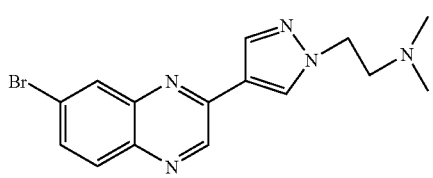

To a solution of 7-bromo-2-(1H-pyrazol-4-yl)quinoxaline (0.225 g, 0.808 mmol) in dry N,N-dimethylformamide (5 mL) under a nitrogen atmosphere was added 60 wt % sodium hydride (92 mg, 2.27 mmol) portionwise. After 5 minutes of stirring with purging, 2-dimethylaminoethylbromide (0.37 g, 0.908 mmol) was added and the reaction mixture stirred at rt for 30 min, concentrated in vacuo and taken into dichloromethane. The organic solution was washed with water (2×), dried ($Na_2SO_4$), filtered and concentrated in vacuo. The residue was purified by silica gel chromatography, eluting with 0-5% methanol in ethyl acetate to furnish the title compound (0.183 g, 66% yield). ESMS m/e: 345.9; 347.8 [M]+.

Related alkylated, acylated and sulfonylated pyrazoles were or can be prepared using this procedure by varying the choice of alkylbromide, acyl chloride or sulfonyl chloride.

Intermediate 15

Preparation of 7-bromo-2-(1-methyl-1H-pyrazol-4-yl)quinoxaline

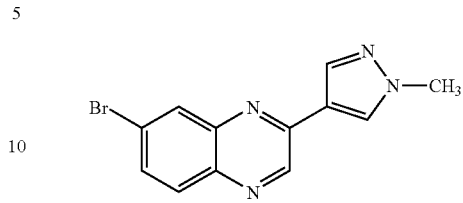

A slurry of 7-bromo-2-chloroquinoxaline (10.0 mmol), 1-methyl-4-(4,4,5,5-tetramethyl-1,3,2-dioxaborolan-2-yl)-1H-pyrazole (10.5 mmol), and [1,1'-bis(diphenylphosphino)ferrocene]dichloropalladium(II) dichloromethane complex (1:1) (0.3 mmol) in 2M aqueous potassium carbonate (15 mL) and 1,4-dioxane (40 mL) was heated at 100° C. for 4 h. The reaction mixture was cooled, poured into water (100 mL), and extracted with (3×100 mL) ethyl acetate. The combined organic layers were filtered through a pad of Celite while rinsing with water and ethyl acetate. The filtrate was separated and the organic layer was dried over sodium sulfate, filtered, and concentrated in vacuo. Purification of the residue by silica gel chromatography (40-70% ethyl acetate/hexanes) provided the title compound as a yellow solid (1.73 g, 57%). MS(ES)+ m/e 289, 291 [M+H]+.

Related aryl or heteroaryl substituted quinoxalines can be prepared using this procedure by varying the choice of aryl- or heteroaryl boronic acid or boronate ester.

Intermediate 16

Preparation of 2-(1-methyl-1H-pyrazol-4-yl)-7-(4,4,5,5-tetramethyl-1,32-dioxaborolan-2-yl)quinoxaline

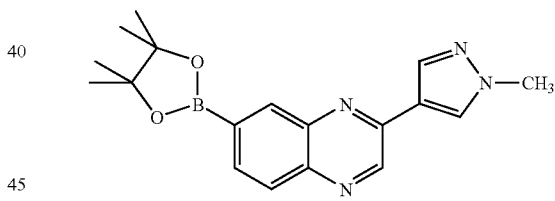

In a 100 mL round bottom flask, a mixture of 7-bromo-2-(1-methyl-1H-pyrazol-4-yl)quinoxaline (10.03 mmol), bis(pinacolato)diboron (12.21 mmol), potassium acetate (32.6 mmol), and [1,1'-bis(diphenylphosphino)ferrocene]dichloropalladium(II) dichloromethane complex (1:1) (0.465 mmol) in dioxane (68 mL) was stirred at 100° C. for 18 h.

The reaction mixture was filtered, washing with 100 mL ethyl acetate. The filtrate was concentrated in vacuo and the brown residue dissolved in hot ethyl acetate (~20 mL). The dark solution was filtered and the filtrate concentrated in vacuo. The residue was partitioned between ethyl acetate (100 mL) and water (70 mL) and the organic phase separated, dried over magnesium sulfate, filtered and concentrated to ~10 mL, then treated with portions of hexanes (~2 volumes). A fine, dark solid precipitate formed which was removed by filtration, and the filtrate was evaporated to an olive residue. The residue was triturated with 3:1 hexanes/ethyl acetate (40 mL) and the resulting light olive green solid collected and dried in vacuo to provide the title compound (2.2 g, 59%). MS(ES)+ m/e 337.2, 339.2 [M+H]+.

Intermediate 17

Preparation of N,N-dimethyl-4-piperidinesulfonamide a) phenylmethyl 4-[(dimethylamino)sulfonyl]-1-piperidinecarboxylate A suspension of an amine such as dimethylamine (4.72 mmol) and sodium hydride (4.72 mmol) in N,N-dimethylformamide (10 ml) was stirred for five minutes at room temperature. Then phenylmethyl 4-(chlorosulfonyl)-1-piperidinecarboxylate (1.60 mmol) was added to the reaction mixture and stirred at 100° C. for 3 hours. The reaction mixture was poured into water (25 ml) and extracted with ethyl acetate (3×25 ml). The combined organic layers were washed with brine, dried over sodium sulfate, filtered, and concentrated to give the title compound (410 mg, 80% yield) as an off-white solid. MS(ES)+ m/e 327.1 [M+H]$^+$.

b) N,N-dimethyl-4-piperidinesulfonamide

A solution of phenylmethyl 4-[(dimethylamino)sulfonyl]-1-piperidinecarboxylate (1.19 mmol) and 10% wt palladium/carbon (0.09 mmol) in methanol (10 ml) was vacuum pumped and back-filled with nitrogen three times. The nitrogen atmosphere was then replaced with hydrogen via a balloon and the reaction stirred for 1 hour at ambient temperature. The reaction was then filtered through a pad of celite and concentrated to give the title compound (200 mg, 87% yield), which was used directly in the next reaction without further purification. 1H NMR (400 MHz, DMSO-$d_6$) δ ppm 3.33 (bs, 1H) 3.30-3.22 (m, 1H) 2.96 (d, J=12.13, 2H) 2.84 (s, 6H) 2.46 (td, J=2.53, 12.38, 2H) 1.80 (d, J=12.13, 2H) 1.46 (qt, J=4.17, 12.34, 2H)

Related piperidinylsulfonamides can be prepared using this procedure by varying the choice of amine.

Other Intermediates can be Prepared Following the General Scheme Below:

Conditions: a) NaO(R1), (R1)OH, 0° C. to room temperature; b) SnCl$_2$•2H$_2$O, ethyl acetate, reflux; c) (R2)SO$_2$Cl, pyridine, 0° C. to room temperature.

Exemplary Capsule Composition

An oral dosage form for administering the present invention is produced by filing a standard two piece hard gelatin capsule with the ingredients in the proportions shown in Table II, below.

TABLE II

| INGREDIENTS | AMOUNTS |
| --- | --- |
| Compound of example 1 | 25 mg |
| Lactose | 55 mg |
| Talc | 16 mg |
| Magnesium Stearate | 4 mg |

Exemplary Injectable Parenteral Composition

An injectable form for administering the present invention is produced by stirring 1.5% by weight of compound of example 1 in 10% by volume propylene glycol in water.

Exemplary Tablet Composition

The sucrose, calcium sulfate dihydrate and an PI3K inhibitor as shown in Table III below, are mixed and granulated in the proportions shown with a 10% gelatin solution. The wet granules are screened, dried, mixed with the starch, talc and stearic acid, screened and compressed into a tablet.

TABLE III

| INGREDIENTS | AMOUNTS |
| --- | --- |
| Compound of example 1 | 20 mg |
| calcium sulfate dehydrate | 30 mg |
| Sucrose | 4 mg |
| Starch | 2 mg |
| Talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of Formula (I)(P):

(I)(P)

in which
R2 is optionally substituted 4-pyrazolyl;
each R5 is independently selected from: halogen, acyl, amino, C1-C6alkyl and alkoxy;
m is 0-1;
R6 is —NHSO$_2$R80, wherein R80 is aryl optionally substituted with one to five groups selected from the group consisting of: C1-C6alkyl, C3-C7cycloalkyl, halogen, amino, substituted amino, trifluoromethyl, cyano, hydroxyl, alkoxy and —(CH$_2$)$_n$COOH, in which n is 0-2;

or a pharmaceutically acceptable salt thereof.

2. The compound of claim 1, wherein R2 is 4-pyrazolyl optionally substituted with one to three groups selected from the group consisting of: C1-C6alkyl and substituted C1-C6alkyl; R80 is aryl optionally substituted with one to five groups selected from the group consisting of: C1-C6alkyl, halogen, cyano, ammo and alkoxy.

3. The compound of claim 1, wherein R2 is 4-pyrazolyl optionally substituted with one to three C1-C6alkyls; R80 is aryl optionally substituted with one to five groups selected from the group consisting of: C1-C6alkyl, halogen, cyano and alkoxy.

4. A pharmaceutical composition comprising a compound according to claim 1 and a pharmaceutically acceptable carrier.

5. A compound of claim 1, which is N-{2-(methyloxy)-5-[3-(1-methyl-1H-pyrazol-4-yl)-6-quinoxalinyl]-3-pyridinyl}benzenesulfonamide.

6. A compound of claim 1, which is 2,4-difluoro-N-{5-[3-(1-methyl-1H- pyrazol-4-yl)-6-quinoxalinyl]-3-pyridinyl}benzenesulfonamide.

7. A compound of claim 1, which is 2,6-difluoro-N-{5-[3-(1-methyl-1H- pyrazol-4-yl)-6-quinoxalinyl]-3-pyridinyl}benzenesulfonamide.

8. A compound of claim 1, which is 2,4-difluoro-N-{2-(methyloxy)-5-[3-(1- methyl-1H-pyrazol-4-yl)-6-quinoxalinyl]-3-pyridinyl}benzenesulfonamide.

9. A compound of claim 1, which is N-[5-(3-{1-[2-(dimethylamino)ethyl]-1H- pyrazol-4-yl}-6-quinoxalinyl)-3-pyridinyl]benzenesulfonamide.

10. A pharmaceutical composition comprising a compound according to claim 5 and a pharmaceutically acceptable carrier.

11. A pharmaceutical composition comprising a compound according to claim 6 and a pharmaceutically acceptable carrier.

12. A pharmaceutical composition comprising a compound according to claim 7 and a pharmaceutically acceptable carrier.

13. A pharmaceutical composition comprising a compound according to claim 8 and a pharmaceutically acceptable carrier.

14. A pharmaceutical composition comprising a compound according to claim 9 and a pharmaceutically acceptable carrier.

* * * * *